(12) United States Patent
Ravenscroft

(10) Patent No.: US 8,740,874 B2
(45) Date of Patent: Jun. 3, 2014

(54) CATHETER DEVICE

(75) Inventor: Adrian C. Ravenscroft, Cohasset, MA (US)

(73) Assignee: Phase One Medical, LLC, Hingham, MA (US)

( * ) Notice: Subject to any disclaimer, the term of this patent is extended or adjusted under 35 U.S.C. 154(b) by 0 days.

(21) Appl. No.: 13/218,266

(22) Filed: Aug. 25, 2011

(65) Prior Publication Data

US 2012/0053564 A1    Mar. 1, 2012

Related U.S. Application Data

(63) Continuation of application No. 12/181,965, filed on Jul. 29, 2008, now Pat. No. 8,007,488, which is a continuation-in-part of application No. 11/559,092, filed on Nov. 13, 2006, now Pat. No. 8,052,659.

(60) Provisional application No. 60/735,257, filed on Nov. 10, 2005.

(51) Int. Cl.
*A61M 25/00* (2006.01)

(52) U.S. Cl.
USPC .................. 604/523; 604/167.03; 604/167.04; 604/35; 604/36; 604/19; 604/99.02; 604/99.03; 604/99.04; 604/43

(58) Field of Classification Search
USPC .......... 604/43, 99.02–99.04, 167.03–167.04, 604/523.35, 36, 19
See application file for complete search history.

(56) References Cited

U.S. PATENT DOCUMENTS

| 396,754 A | 1/1889 | Mayfield |
| 4,137,906 A | 2/1979 | Akiyama et al. |
| 4,180,068 A | 12/1979 | Jacobsen et al. |
| 4,509,946 A | 4/1985 | McFarlane |
| 4,643,712 A | 2/1987 | Kulik et al. |

(Continued)

FOREIGN PATENT DOCUMENTS

| EP | 1374941 | 1/2004 |
| JP | 2001-137350 | 5/2001 |

(Continued)

OTHER PUBLICATIONS

Franco et al.; Effective central venous catheter hemodialysis with a novel needlefree connection device (TEGO}); Aug. 2004.

(Continued)

*Primary Examiner* — Edelmira Bosques
(74) *Attorney, Agent, or Firm* — Pandiscio & Pandiscio

(57) ABSTRACT

A catheter includes an elongate body having first and second chambers extending within the elongate body from a proximal end to an intermediate section, the first chamber having a first opening and the second chamber having a second opening at the intermediate section. The catheter also includes a valve structure that may have first and second barrier elements to open or close the first and second openings, respectively. The first and the second barrier elements may be coupled by a connecting structure moving within an opening in a guide structure. Alternatively, the first and the second barrier elements may be coupled in a U-shaped structure that moves over the guide structure. To permit flushing of the chambers when the first and second openings are closed, the first and second chambers may also be connected by a connecting channel defined by an opening in a wall of the elongate body.

12 Claims, 33 Drawing Sheets

(56) References Cited

U.S. PATENT DOCUMENTS

| | | |
|---|---|---|
| 4,693,257 A | 9/1987 | Markham |
| 4,727,873 A | 3/1988 | Mobin-Uddin |
| 5,030,210 A | 7/1991 | Alchas |
| 5,100,424 A | 3/1992 | Jang et al. |
| 5,112,301 A | 5/1992 | Fenton, Jr. et al. |
| 5,209,723 A | 5/1993 | Twardowski et al. |
| 5,224,938 A | 7/1993 | Fenton, Jr. |
| 5,250,034 A | 10/1993 | Appling et al. |
| 5,261,885 A | 11/1993 | Lui |
| 5,304,155 A | 4/1994 | Lui |
| 5,324,304 A | 6/1994 | Rasmussen |
| 5,360,403 A | 11/1994 | Mische |
| 5,405,320 A | 4/1995 | Twardowski et al. |
| 5,421,832 A | 6/1995 | Lefebvre |
| 5,484,384 A | 1/1996 | Fearnot |
| 5,509,897 A | 4/1996 | Twardowski et al. |
| 5,542,933 A | 8/1996 | Marks |
| 5,549,548 A * | 8/1996 | Larsson ............... 604/35 |
| 5,569,182 A | 10/1996 | Twardowski et al. |
| 5,578,010 A | 11/1996 | Ashby |
| 5,685,867 A | 11/1997 | Twardowski et al. |
| 5,730,717 A | 3/1998 | Gelbfish |
| 5,792,118 A * | 8/1998 | Kurth et al. ............... 604/246 |
| 5,807,329 A | 9/1998 | Gelman |
| 5,807,349 A | 9/1998 | Person et al. |
| 5,807,356 A | 9/1998 | Finch, Jr. et al. |
| 5,857,464 A | 1/1999 | Desai |
| 5,891,091 A | 4/1999 | Teirstein |
| 5,938,582 A | 8/1999 | Ciamacco, Jr. et al. |
| 5,961,486 A | 10/1999 | Twardowski et al. |
| 5,968,071 A | 10/1999 | Chevillon et al. |
| 5,989,213 A | 11/1999 | Maginot |
| 6,007,558 A | 12/1999 | Ravenscroft et al. |
| 6,027,514 A | 2/2000 | Stine et al. |
| 6,052,612 A | 4/2000 | Desai |
| 6,074,339 A | 6/2000 | Gambale et al. |
| 6,074,374 A | 6/2000 | Fulton |
| 6,099,518 A | 8/2000 | Adams et al. |
| 6,102,891 A | 8/2000 | Maria Van Erp |
| 6,149,607 A | 11/2000 | Simpson et al. |
| 6,183,438 B1 | 2/2001 | Berguer |
| 6,213,976 B1 | 4/2001 | Trerotola |
| 6,258,026 B1 | 7/2001 | Ravenscroft et al. |
| 6,267,775 B1 | 7/2001 | Clerc et al. |
| 6,325,778 B1 | 12/2001 | Zadno-Azizi et al. |
| 6,352,521 B1 | 3/2002 | Prosl |
| 6,355,014 B1 | 3/2002 | Zadno-Azizi et al. |
| 6,361,545 B1 | 3/2002 | Macoviak et al. |
| 6,364,867 B2 | 4/2002 | Wise et al. |
| 6,375,654 B1 | 4/2002 | McIntyre |
| 6,423,706 B2 * | 7/2002 | Sodemann ............... 514/222.5 |
| 6,514,191 B1 | 2/2003 | Popowski et al. |
| 6,579,302 B2 | 6/2003 | Duerig et al. |
| 6,592,544 B1 | 7/2003 | Mooney et al. |
| 6,638,233 B2 | 10/2003 | Corvi et al. |
| 6,645,160 B1 | 11/2003 | Heesch |
| 6,701,180 B1 | 3/2004 | Desai |
| 6,872,217 B2 | 3/2005 | Walak et al. |
| 6,881,218 B2 | 4/2005 | Beyer et al. |
| 6,923,822 B2 | 8/2005 | Crawford et al. |
| 6,932,829 B2 | 8/2005 | Majercak |
| 6,936,058 B2 | 8/2005 | Forde et al. |
| 7,282,041 B2 | 10/2007 | Igarashi et al. |
| 8,007,488 B2 | 8/2011 | Ravenscroft |
| 8,052,659 B2 | 11/2011 | Ravenscroft et al. |
| 2002/0026156 A1 | 2/2002 | Quinn |
| 2002/0038097 A1 | 3/2002 | Corvi et al. |
| 2003/0144623 A1 | 7/2003 | Heath et al. |
| 2003/0212431 A1 | 11/2003 | Brady et al. |
| 2004/0030319 A1 | 2/2004 | Korkor et al. |
| 2004/0034329 A1 | 2/2004 | Mankus et al. |
| 2004/0082909 A1 | 4/2004 | Shia et al. |
| 2004/0092890 A1 | 5/2004 | Ash |
| 2004/0181191 A1 | 9/2004 | Teitelbaum |
| 2004/0210180 A1 | 10/2004 | Altman |
| 2004/0210187 A1 | 10/2004 | Zawacki |
| 2005/0038413 A1 | 2/2005 | Sansoucy |
| 2005/0165419 A1 | 7/2005 | Sauer et al. |
| 2005/0228339 A1 | 10/2005 | Clark |
| 2005/0245900 A1 | 11/2005 | Ash |
| 2005/0256461 A1 | 11/2005 | DiFiore et al. |
| 2005/0288704 A1 | 12/2005 | Cartier et al. |
| 2006/0079928 A1 | 4/2006 | Cartier et al. |
| 2006/0253063 A1 | 11/2006 | Schweikert |
| 2007/0198050 A1 | 8/2007 | Ravenscroft et al. |
| 2007/0225661 A1 | 9/2007 | Ash et al. |
| 2007/0225682 A1 | 9/2007 | Ash et al. |
| 2007/0232981 A1 | 10/2007 | Ravenscroft et al. |

FOREIGN PATENT DOCUMENTS

| | | |
|---|---|---|
| WO | WO 01/15609 | 3/2001 |
| WO | WO 02/28286 | 4/2002 |
| WO | WO 2007/059018 | 5/2007 |

OTHER PUBLICATIONS

G2 Filter System (Information for Use); G2 Filter System Jugular/Subclavian Vein Approach; Bard Peripheral Vascular, Inc.; 2005.

G2 Filter System (Information for Use); G2 Filter System Femoral Vein Approach; Bard Peripheral Vascular, Inc.; 2005.

RecoveryCone® Removal System for use with the Recovery® Filter (Information for Use); Bard Peripheral Vascular, Inc.; 2005.

Int'l Search Report for PCT/US06/43961 [WO 2007/059018] which claims priority to U.S. Appl. No. 60/735,257 (Nov. 14, 2007).

* cited by examiner

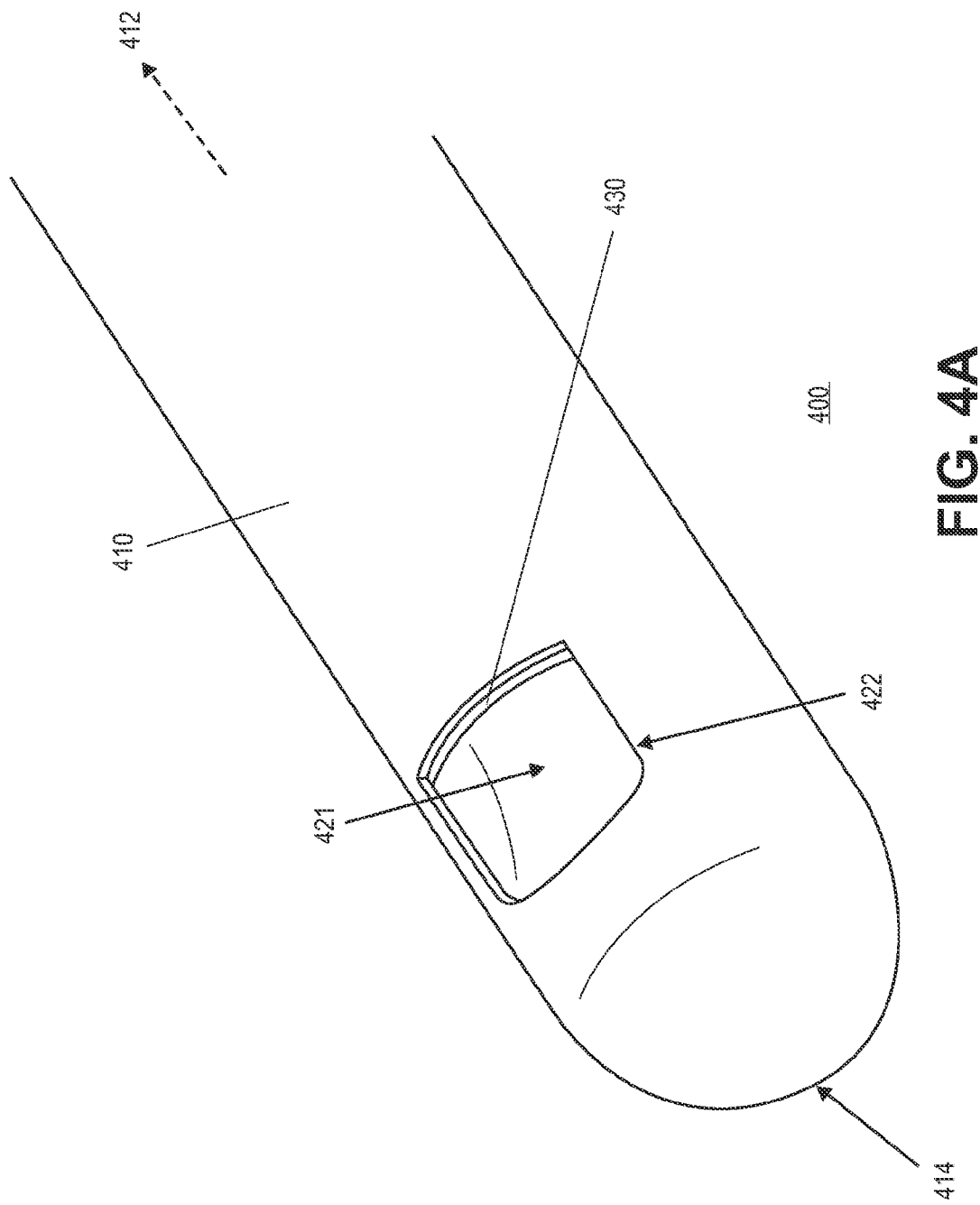

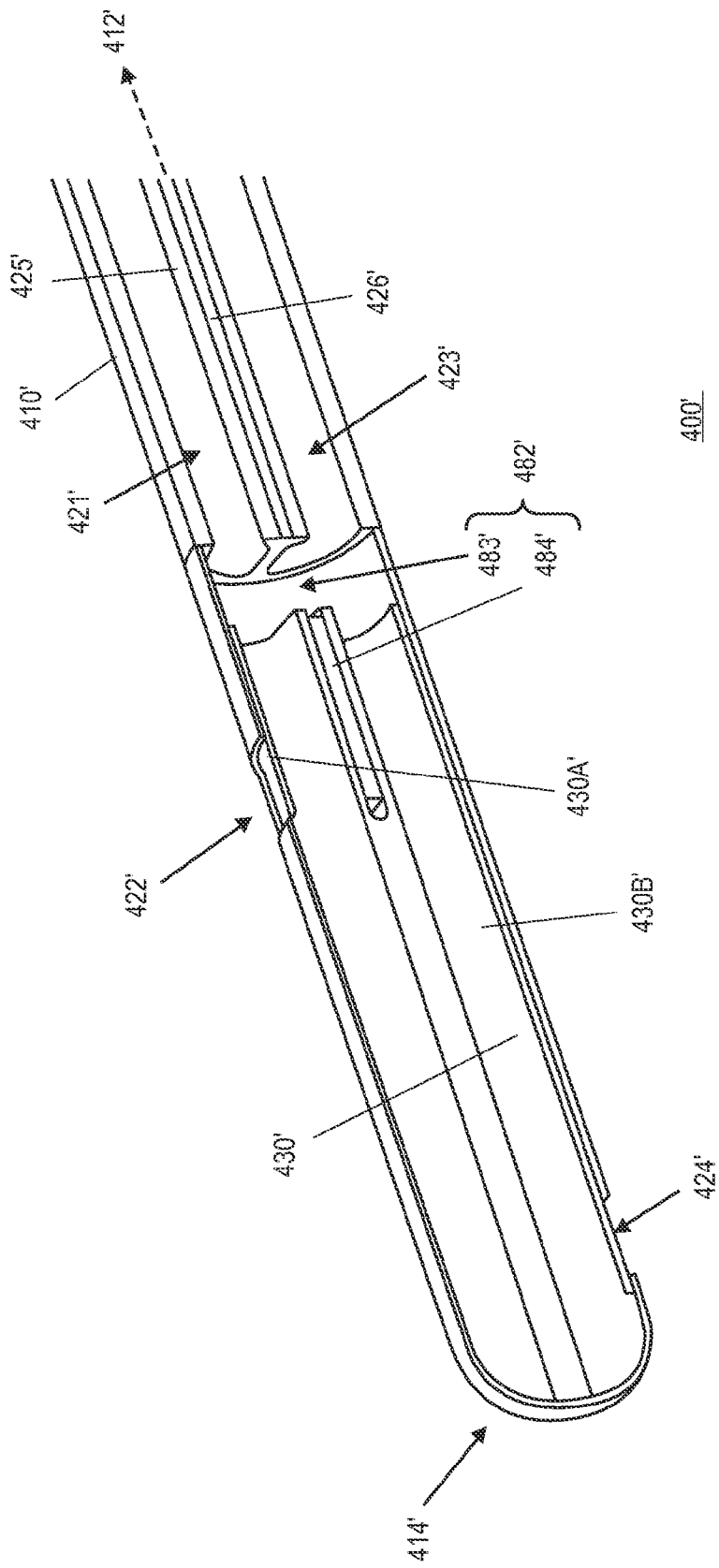

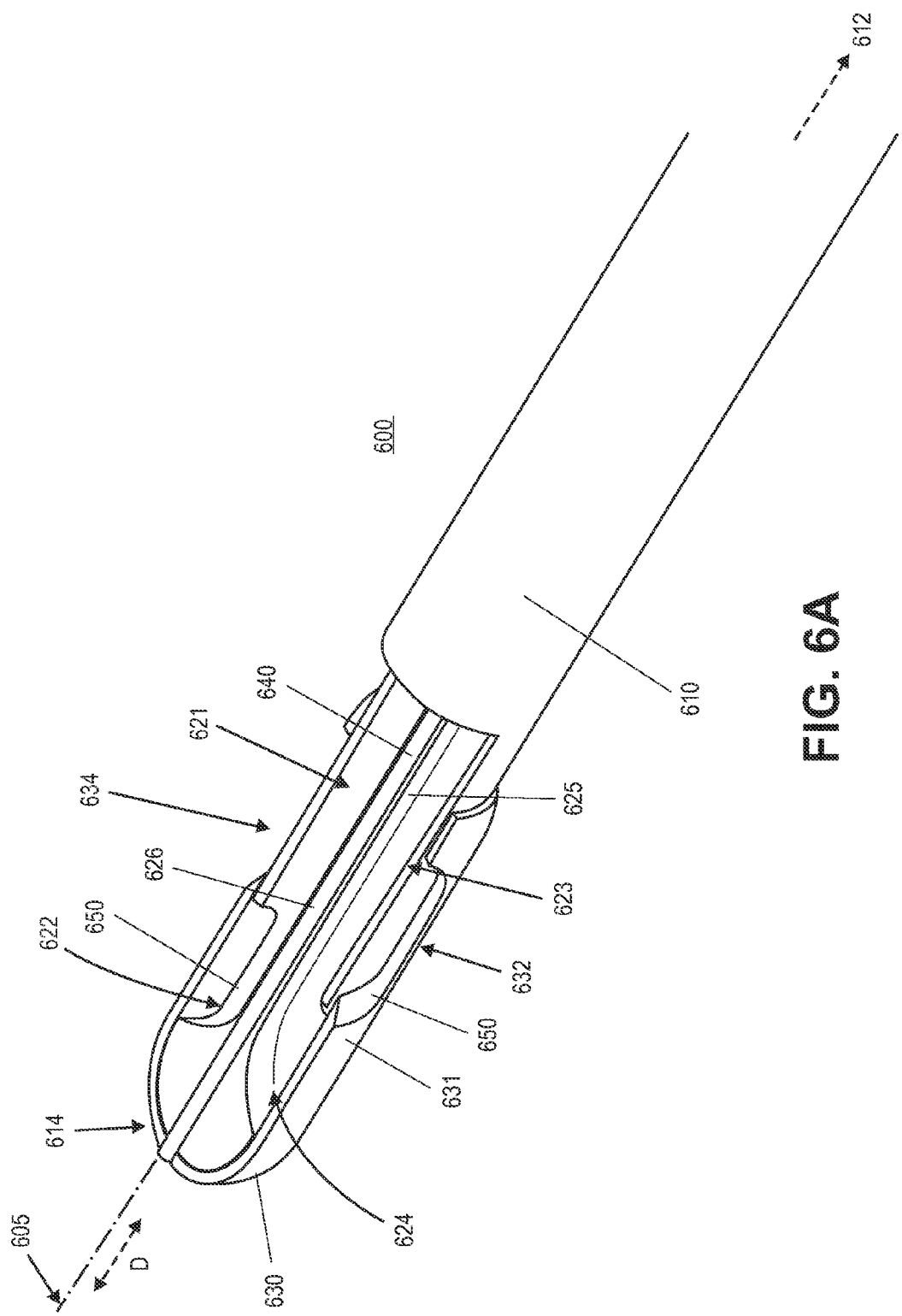

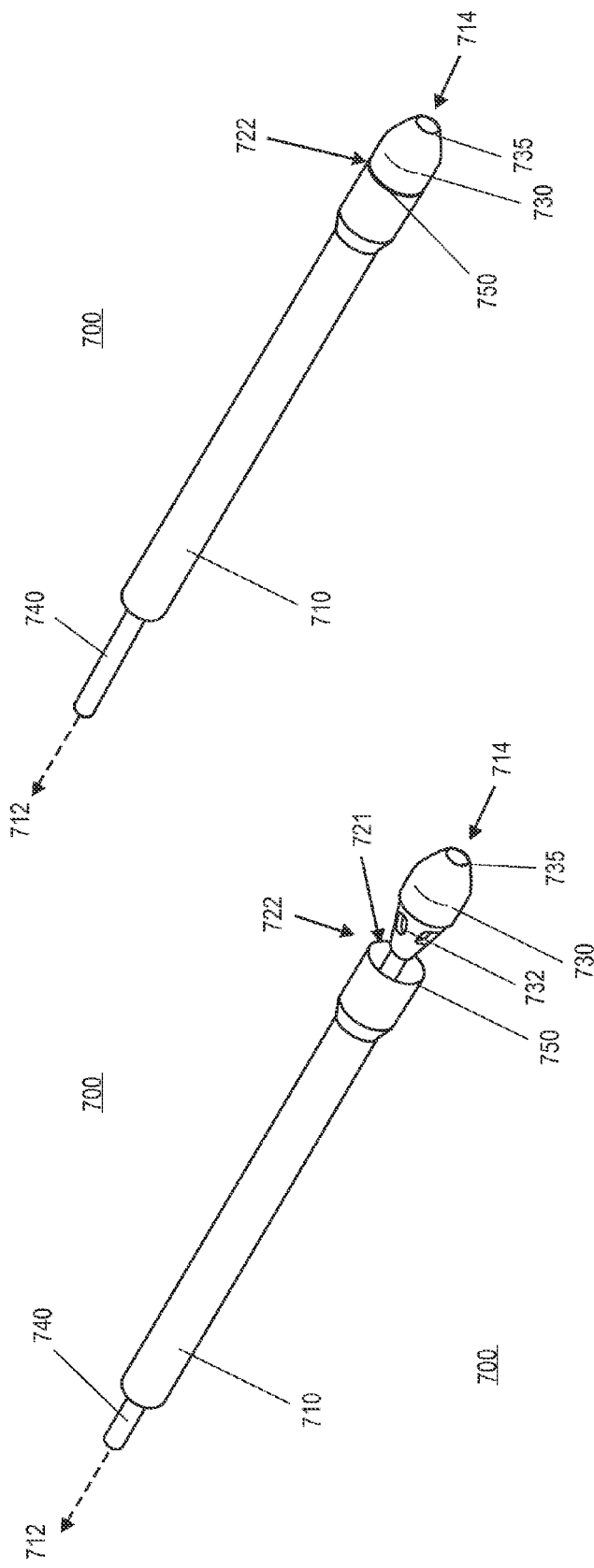

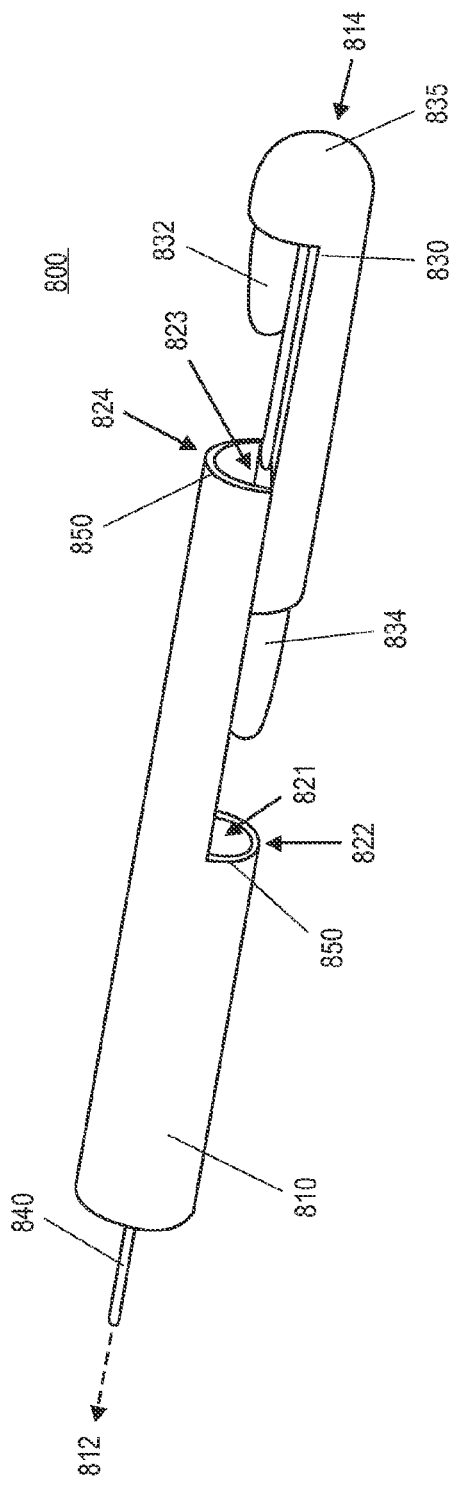
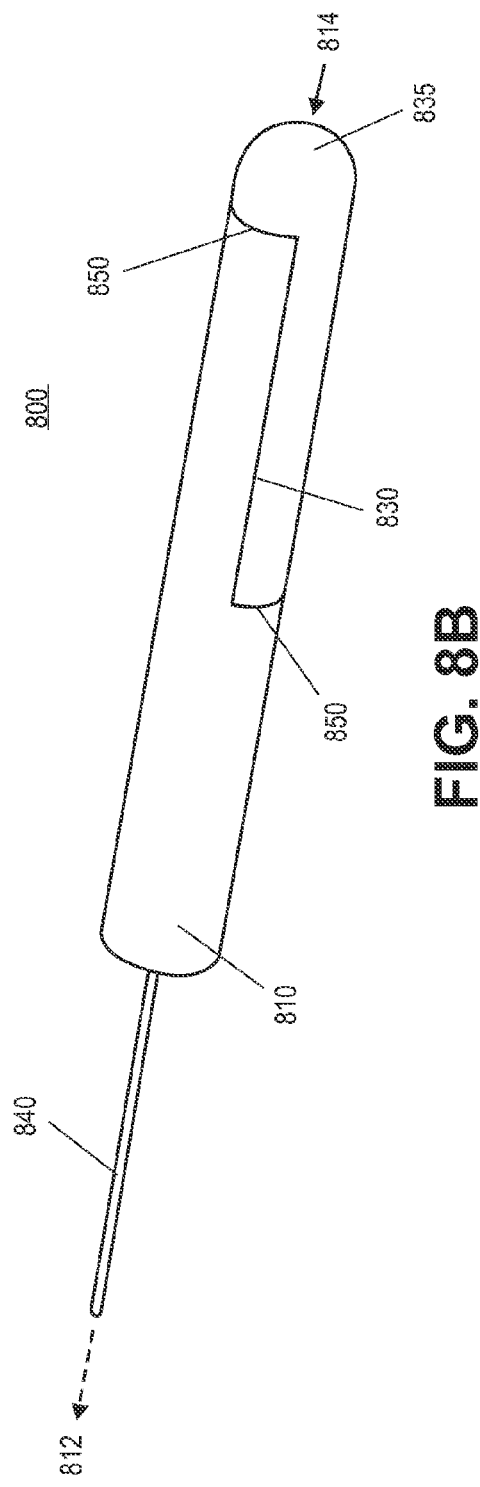
FIG. 8A
FIG. 8B

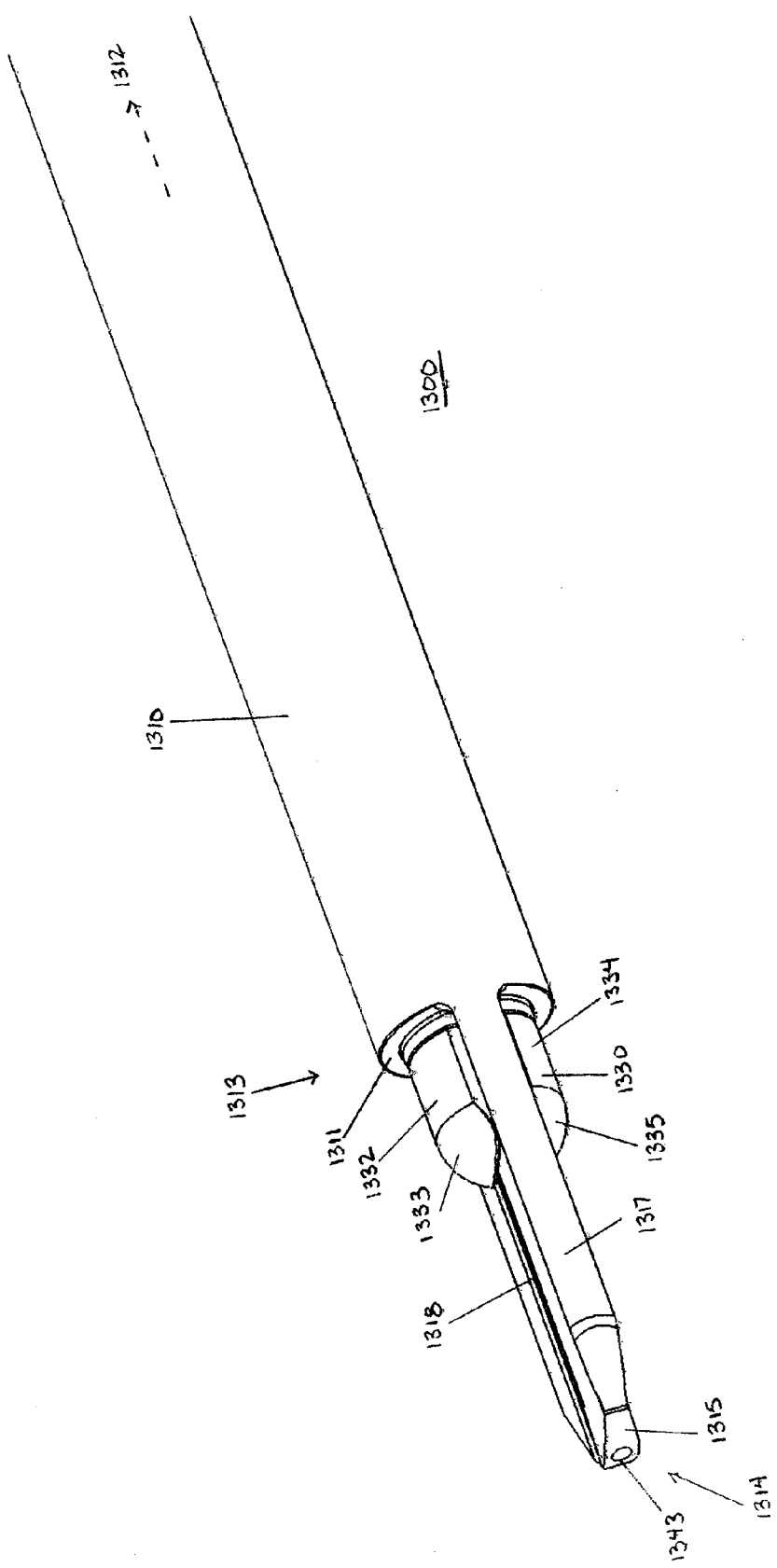

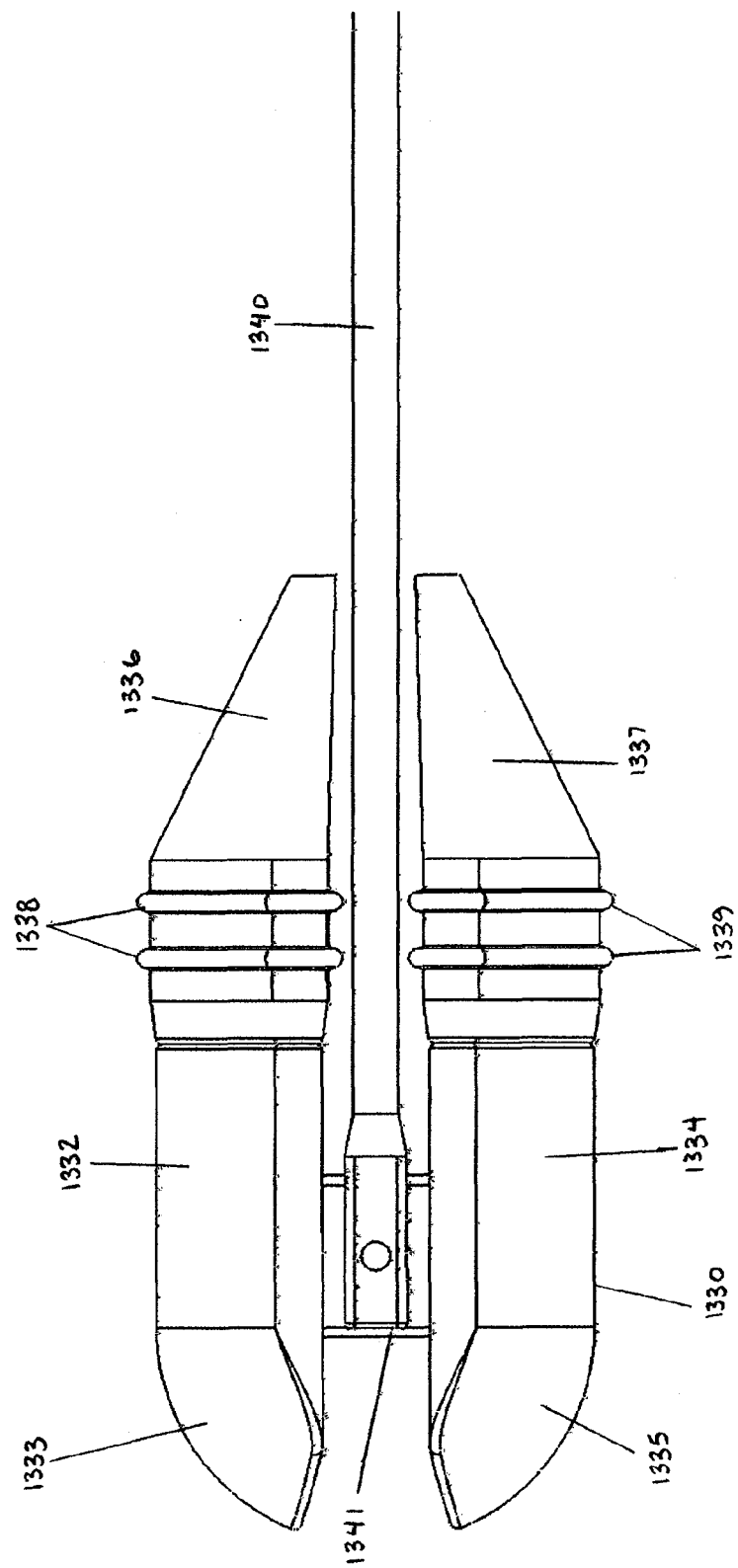

CATHETER DEVICE

CROSS REFERENCE TO RELATED APPLICATIONS

This application is a continuation of U.S. patent application Ser. No. 12/181,965, filed Jul. 29, 2008, titled "Catheter Device", which is a continuation-in-part of U.S. patent application Ser. No. 11/559,092, filed Nov. 13, 2006, titled "Catheter Device", which claims priority to U.S. Provisional Patent Application No. 60/735,257, filed Nov. 10, 2005, titled "Central Venous Catheter". Each of these patent applications is herein incorporated by reference in its entirety.

BACKGROUND OF THE INVENTION

1. Field of the Invention

This invention relates generally to catheters, and more particularly, to a venous catheter that includes a valve mechanism for controlling fluid flow through the catheter.

2. Description of Related Art

The use of cuffed tunneled central venous catheters has become widely accepted as a viable option for prolonged temporary vascular access as well as permanent vascular access for hemodialysis. It is estimated that 7 million central venous catheters (CVCS) will be inserted into patients annually in the United States. Unfortunately, the durability of central venous catheters is limited by catheter malfunction, primarily manifested by insufficient flow or total catheter lumina occlusion.

A variety of catheter designs exist on the market. Some catheter designs are simple in nature and have a single lumen that extends through an elongate body, while other designs employ two or three lumens. Each lumen has an opening at, or near, the distal tip of the catheter body. More recently, the focus of catheter design has focused on tip geometries that are supposed to provide lower occlusion rates and higher flow rates. Despite the various existing catheter designs, the primary patency rate has been reported to be a dismal 65% at 1 year and in some institutions as low as 45% at 1 year.

To help prevent occlusion, the current clinical practice is to "lock" catheters with Heparin (5000 U/mL). This practice attempts to create a highly anticoagulant environment within each catheter lumen. This practice has inherent risks of systemic anticoagulation since most catheters can hold at least 3 mL of Heparin resulting in a dosing potential of 15,000 U. Furthermore, despite the high concentration of anticoagulant, central venous catheters are still prone to partial or total occlusion leading to poor or failed dialysis.

Failure of hemodialysis catheter patency often results from the accumulation of obstructing thrombus or fibrin at the distal tip of the catheter. Fibrin accumulation may cause failure of smaller single-, double- and triple lumen central venous catheters, but the problem is more significant with hemodialysis catheters, because even partial encroachment of fibrin on the catheter lumen can prevent the high flow rates required for satisfactory hemodialysis. Instillation of Urokinase or tPA into each catheter lumen for thirty minutes in the hemodialysis unit may restore patency to the catheter by lysing thrombosis at the catheter tip, but the effect is often transient or ineffective. No current consensus exists as to what further method is optimal for maintaining catheter patency in patients with regard to catheter failure caused by fibrin sheath formation.

It is also believed that poor catheter position or catheter kinking may also be partially responsible for the low patency rates.

A serious complication that may arise with the use of catheters is infection caused by microbial colonization on the catheter. Even using the best available aseptic techniques during insertion and maintenance of the catheter, one out of every twenty CVCs inserted will be associated with at least one episode of blood stream infection. As a result, it is estimated that more than 300,000 episodes of CVC-related bloodstream infections (CRBSI) will occur annually in the United States. On average, each episode of CRBSI will cost almost $30,000 per survivor and result in an additional average stay of 6.5 days in the ICU.

For long-term catheters, the hub is believed to be a major source of microbial colonization for the catheter lumen, ultimately leading to bloodstream infections through luminal colonization of the intravascular segment.

The surfaces of indwelling medical devices act as a suitable substratum for microbial colonization leading to life threatening infections. Organisms that adhere to the catheter surface maintain themselves by producing a substance rich in exopolysaccharides, often referred to as a fibrous microbial biofilm. The organisms, i.e. bacteria, embed themselves in the biofilm layer, becoming more resistant to the antimicrobial activity of glycopeptide antibiotics. Following catheter insertion, a thrombin sheath rich in host proteins covers the internal and external surface of the catheter. The proteins in the thrombin sheath—such as fibrin, fibrinogen, fibronectin, laminin, thrombospondin, and collagen—act as adhesions. Organisms, such as staphylococci, bind to fibronectin. Staphylococcus aureus binds strongly to both fibronectin and fibrinogen, while Candida albicans binds well to fibrin. This process observed at the molecular level, is translated into a correlation at the clinical level between thrombogenesis and infection.

In one study, it was determined that catheter related bacteraemia (CRB) is the most significant complication of hemodialysis catheters occurring in 5-18% of catheters or in 3.9-8.6 episodes/1000 catheter days. It is also reported that the cumulative hazard of developing CRB revealed a roughly linear increase in cumulative hazard, suggesting that the risk of developing CRB is constant over time (catheterization days). This suggests that infection is random, there is no threshold effect, and the chance of infection is not related to how long the catheter has been implanted.

Accordingly, it is evident that central venous catheters are plagued with a variety of complications and no existing design has successfully addressed all clinical issues. The most prevalent mechanical complication is occlusion of the distal tip followed by catheter fracture. Although catheter occlusion is not as serious as CRB since it rarely causes death, it does lead to additional non-elective therapies such as tPA instillation and catheter exchange (.about.10%). It is evident that the current catheter designs do not provide a reliable means to prevent distal tip thrombosis. In addition, distal tip fouling caused by catheter misplacement, transmural tip incorporation, and external fibrin sheath formation negatively influences catheter performance. Furthermore, microbial colonization on the catheter presents the risk of life-threatening infection.

SUMMARY OF THE INVENTION

In view of the problems described previously, the present invention provides a catheter design that attempts to address the complications associated with central venous catheters.

Accordingly, a catheter according to aspects of the present invention includes an elongate body with a distal end, a proximal end, and an intermediate section disposed between the distal end and the proximal end. The elongate body includes a first chamber and a second chamber extending within the elongate body from the proximal end to the intermediate section, the first chamber having a first chamber opening at the intermediate section, and the second chamber having a second chamber opening at the intermediate section. The elongate body also includes a guide structure extending from the intermediate section to the distal end. The catheter also includes a valve structure movable along the guide structure between a covered position and an uncovered position, the valve structure covering the first chamber opening and the second chamber opening when the valve structure is in the covered position, and the valve structure uncovering the first chamber opening and the second chamber opening when the valve structure is in the uncovered position. The catheter may include a wall dividing the first chamber and the second chamber and extending past the first chamber opening and the second chamber opening to define the guide structure. The valve structure may include a first barrier element and a second barrier element, the first barrier element covering the first chamber opening and the second barrier element covering the second chamber opening when the valve structure is in the covered position, and the first barrier element uncovering the first chamber opening and the second barrier element uncovering the second chamber opening when the valve structure is in the covered position. The first barrier element and the second barrier element may include a corresponding tapered structure that extends into the first chamber and the second chamber, respectively, when the valve structure is in the covered position. The first barrier element and the second barrier element may include a corresponding partially domed structure extending from the tapered structure toward the distal end, the partially domed structure being disposed outside the corresponding first chamber or second chamber when the valve structure is in the covered position. The valve structure may also include a connecting structure connecting the first barrier element and the second barrier element and passing through an opening extending along the guide structure, the connecting structure moving along the opening when the valve structure moves between the covered position and the uncovered position. A control wire coupled to the connecting structure, the control wire being movable to control movement of the connecting structure along the opening and corresponding movement of the valve structure between the covered position and the uncovered position.

Another catheter according to aspects of the present invention includes an elongate body with a distal end, a proximal end, and an intermediate section disposed between the distal end and the proximal end. The elongate body includes a first chamber and a second chamber extending within the elongate body from the proximal end to the intermediate section, the first chamber having a first chamber opening at the intermediate section, and the second chamber having a second chamber opening at the intermediate section. The elongate body also includes a guide structure extending from the intermediate section toward the distal end. The catheter also includes a valve structure positioned at the distal end and movable along the guide structure between a covered position and an uncovered position, the valve structure covering the first chamber opening and the second chamber opening when the valve structure is in the covered position, and the valve structure uncovering the first chamber opening and the second chamber opening when the valve structure is in the uncovered position. The valve structure of the catheter may include a first barrier element and a second barrier element, the first barrier element covering the first chamber opening and the second barrier element covering the second chamber opening when the valve structure is in the covered position, and the first barrier element uncovering the first chamber opening and the second barrier element uncovering the second chamber opening when the valve structure is in the covered position. The second barrier element may include a corresponding tapered structure that extends into the first chamber and the second chamber, respectively, when the valve structure is in the covered position. The valve structure may be a U-shaped structure disposed over the guide structure, the first barrier element and the second barrier element being positioned on opposing sides of the guide structure and extending to an end structure that defines the distal end and connects the first barrier element and the second barrier element. The end structure may be a substantially domed structure. The catheter may further include a control wire coupled to the end structure, the control wire being movable to control movement of the end structure to and from the guide structure and corresponding movement of the valve structure between the covered position and the uncovered position.

The catheters described herein may further comprise a fluid source coupled to the first chamber at the proximal end and a vacuum source coupled to the second chamber at the proximal end, the fluid source causing an outflow from the first chamber through the first chamber opening, and the vacuum source causing an inflow into the second chamber through the second chamber opening. The guide structure of the catheters may substantially separate the inflow into the second chamber from the outflow from the first chamber. The first chamber opening and the second chamber opening of the catheters may also be positioned according to a configuration that substantially separates the inflow into the second chamber from the outflow from the first chamber.

Yet another catheter according to aspects of the present invention includes an elongate body including an outer wall ending from a proximal end to a distal end, a first chamber and a second chamber extending within the outer wall, the first chamber having a first chamber and the second chamber having a second chamber opening, the first chamber and the second chamber being connected by a connecting channel in the outer wall. The elongate body includes a valve structure movable between a covered position and an uncovered position, the valve structure covering the first chamber opening and the second chamber opening when the valve structure is in the covered position, and the valve structure uncovering the first chamber opening and the second chamber opening when the valve structure is in the uncovered position. Fluid flows between the first chamber and the second chamber through the connecting channel when the valve structure is in the covered position. The connecting channel may be disposed along a plane that is substantially perpendicular to the longitudinal direction. The connecting channel may also extend along a periphery of the outer wall. In addition, an outer cover sealing the connecting channel along an outer surface of the outer wall. In one embodiment, the elongate body may include a dividing wall extending along a longitudinal direction and dividing the first chamber and the second chamber, and the connecting channel may extend inwardly from an outer surface of the outer wall into a part of the dividing wall and extend across opposing sides of the dividing wall, the opposing sides corresponding to the first chamber and the second chamber, respectively. In another embodiment, the connecting channel may include a groove that extends inwardly from an outer surface of the outer wall and partially through the outer wall; at least one first aperture connecting the groove to the first chamber; and at least one second aperture connecting the groove to the second chamber.

A method for operating a catheter in a body passageway according to aspects of the present invention includes guiding a catheter through a body passageway, the catheter including an elongate body with a distal end, a proximal end, and an intermediate section disposed between the distal end and the proximal end. The elongate body includes a first chamber and a second chamber extending within the elongate body from the proximal end to the intermediate section, the first chamber and the second chamber having a first chamber opening and a second chamber opening at the intermediate section, respectively. The elongate body also includes a guide structure extending from the intermediate section to the distal end. The method further includes moving a valve structure along the guide structure between a covered position and an uncovered position, the valve structure covering the first chamber opening and the second chamber opening when the valve structure is in the covered position, and the valve structure uncovering the first chamber opening and the second chamber opening when the valve structure is in the uncovered position.

Another method for operating a catheter in a body passageway according to aspects of the present invention includes guiding a catheter through a body passageway, the catheter including an elongate body with a distal end, a proximal end, and an intermediate section disposed between the distal end and the proximal end. The elongate body includes a first chamber and a second chamber extending within the elongate body from the proximal end to the intermediate section, the first chamber having a first chamber opening at the intermediate section, and the second chamber having a second chamber opening at the intermediate section. The elongate body also includes a guide structure extending from the intermediate section toward the distal end. The method further includes moving a U-shaped valve structure positioned at the distal end along the guide structure between a covered position and an uncovered position, the valve structure covering the first chamber opening and the second chamber opening when the valve structure is in the covered position, and the valve structure uncovering the first chamber opening and the second chamber opening when the valve structure is in the uncovered position. The valve structure may include a first barrier element and a second barrier element, the first barrier element covering the first chamber opening and the second barrier element covering the second chamber opening when the valve structure is in the covered position, the first barrier element uncovering the first chamber opening and the second barrier element uncovering the second chamber opening when the valve structure is in the covered position, and the first barrier element and the second barrier element being positioned on opposing sides of the guide structure and extending to a substantially domed structure that defines the distal end and connects the first barrier element and the second barrier element Methods for operating a catheter in a body passageway according to aspects of the present invention may also include coupling a fluid source to the first chamber at the proximal end, coupling a vacuum source to the second chamber at the proximal end, and when the valve structure is in the uncovered position, generating, with the fluid source, an outflow from the first chamber through the first chamber opening, and generating, with the vacuum source, an inflow into the second chamber through the second chamber opening.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 4A illustrates a distal end of an exemplary embodiment with a gate in an open valve position.

FIG. 4D illustrates a cross-sectional view of an exemplary embodiment with two interior chambers and two respective gates each in a closed valve position.

FIG. 6A illustrates a sectional view of a distal end of an exemplary embodiment with an axially translating cap-shaped valve in an open valve position.

FIG. 7A illustrates the distal end of an exemplary embodiment with a single interior chamber and a valve plug in an open valve position.

FIG. 7B illustrates the distal end of the exemplary embodiment of FIG. 7A with the valve plug in a closed valve position.

FIG. 8A illustrates the distal end of an exemplary embodiment with two interior chambers and a valve plug in an open valve position.

FIG. 8B illustrates the distal end of the exemplary embodiment of FIG. 8A with the valve plug in a closed valve position.

FIG. 13A illustrates an exemplary embodiment in a closed valve position.

FIG. 13D illustrates the valve mechanism of the exemplary embodiment of FIG. 13A.

DETAILED DESCRIPTION

Figure 1:
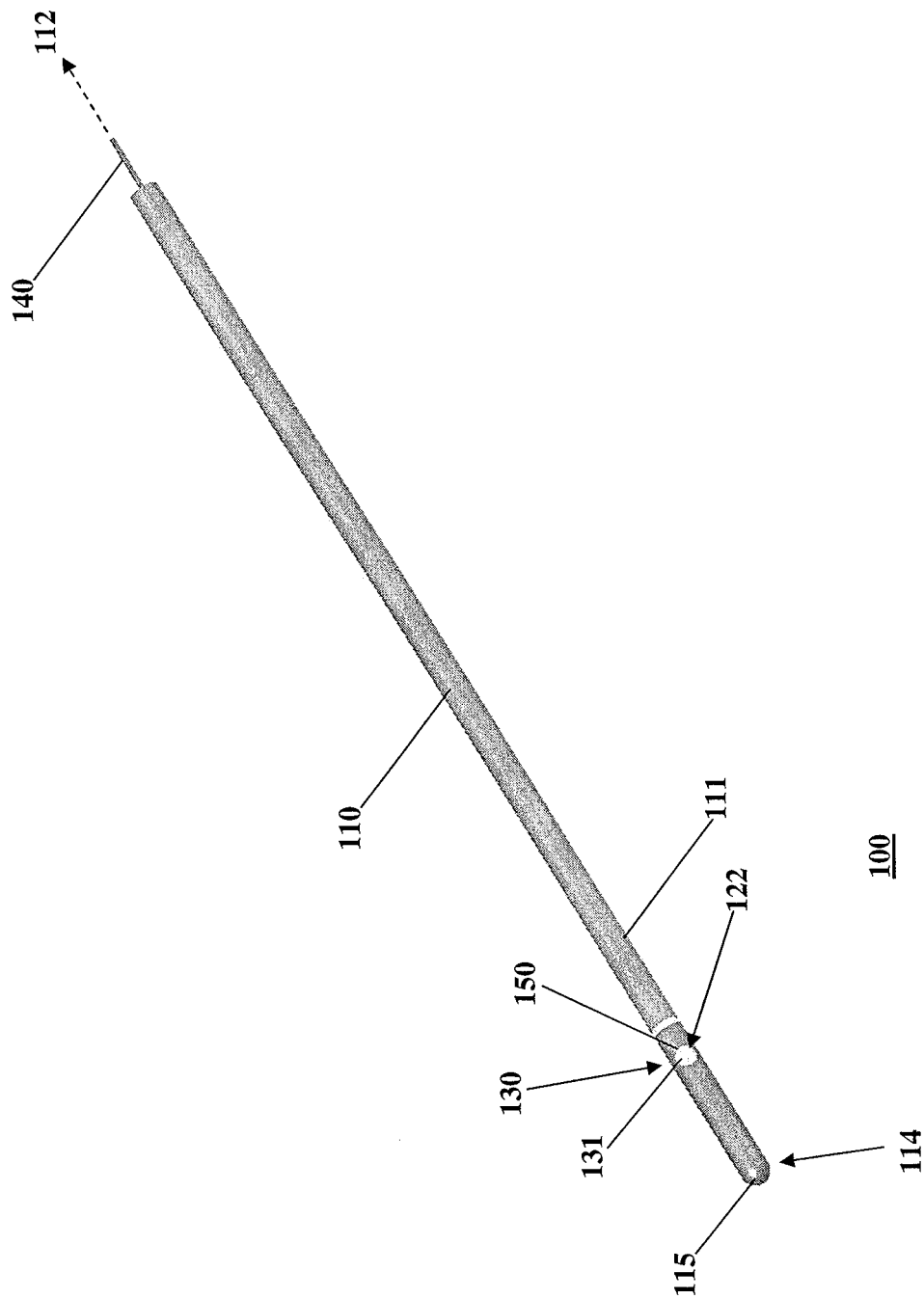
FIG. 1 illustrates a distal end of an exemplary embodiment.

Referring to FIG. 1, an exemplary embodiment of the present invention is generally illustrated as a catheter 100. In particular, as described further below, the catheter 100 may be employed as a central venous catheter for hemodialysis. The catheter 100 has an elongate catheter body 110 which extends from a proximal end 112 to a distal end 114. The catheter 100 is generally flexible to permit positioning within a body passageway, such as a blood vessel. Flexibility, for instance, may be enhanced by incorporating multiple durometer elastomers or polymers within the parts of the catheter 100.

The catheter 100 has a lumen, or interior chamber, within the elongate catheter body 110. The interior chamber (not shown) acts to channel fluid between the proximal end 112 and the distal end 114. The interior chamber has a port, or chamber opening, 122 that passes through a body wall 111 of the catheter body 110. The chamber opening 122 allows the interior chamber to communicate with an area in the body passageway, outside the catheter body 110. The catheter 100 may be operated from the proximal end 112 to guide the distal end 114 to a position in a body passageway. The catheter 100 may deliver fluid to the position in the body passageway through the chamber opening 122. Alternatively, the catheter 100 may draw fluid from the body passageway through the chamber opening 122.

The catheter 100 employs a valve mechanism 130 to control the flow of fluid through the chamber opening 122. As illustrated in FIG. 1, the valve mechanism 130 has a valve wall 131 that acts as a barrier to the flow of fluid into, or from, the catheter 100 when the valve wall 131 is aligned over the chamber opening 122 in a closed valve position. In the closed valve position, the valve mechanism 130 substantially prevents or minimizes the loss of fluid that is intended to be "locked" in the chamber opening 122, an occurrence also known as "lock drop." However, when the valve mechanism 130 is in an open valve position, the valve wall 131 no longer blocks the flow of fluid through the chamber opening 122, and fluid flows between the interior chamber and the area in the passageway outside the catheter 100.

In general, when the valve mechanism 130 is in the closed valve position, a barrier, e.g. the valve wall 131, is in a covered position over the chamber opening 122. On the other hand, when the valve mechanism 130 is in the open valve position, the barrier is in an uncovered position. As used herein, the term barrier refers to a structure, such as the valve wall 131, that substantially prevents or minimizes the flow of fluid.

The distal end 114 of the body 110 forms rounded end, or nose, 115 for the catheter 100. Advantageously, the rounded end 115 reduces blood flow turbulence. Moreover, the shape minimizes contact of the most distal segment, e.g. 10-15 centimeters, of the catheter with native tissue in the body passageway when the catheter is in place.

Figures 2A, 2B:
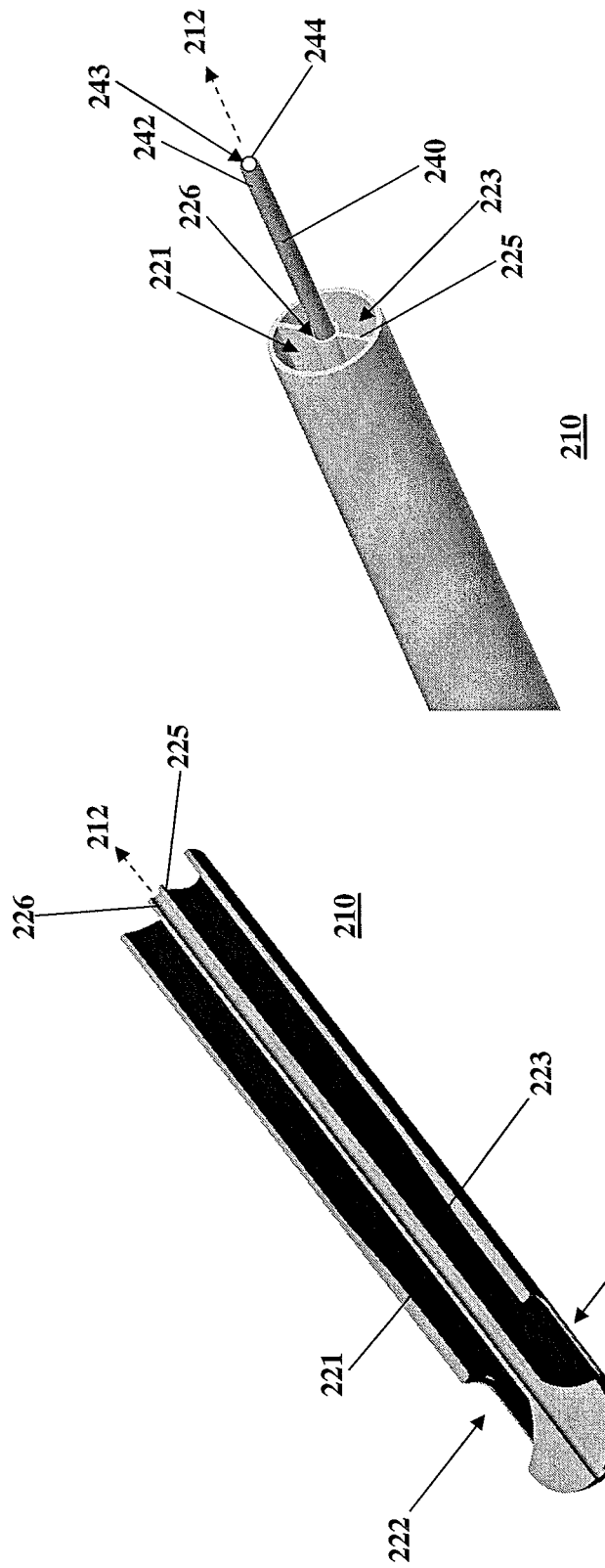
FIG. 2A illustrates a cross-sectional view of a distal end of a catheter body with two interior chambers.
FIG. 2B illustrates a sectional view of a control wire of an exemplary embodiment.

Although the embodiment of FIG. 1 is described in terms of a single interior chamber with chamber opening 122, the cross-sectional view of FIG. 2A demonstrates that other embodiments may employ more than one interior chamber. Accordingly, the elongate catheter body 210 shown in FIG. 2A has two interior chambers 221 and 223. The dividing wall 225 extends longitudinally along the catheter body 210 to separate two halves of the catheter body 210 to define the two interior chambers 221 and 223. The interior chambers 221 and 223 respectively have ports, or chamber openings, 222 and 224. The chamber openings 222 and 223 are near, but spaced from, the distal end 214 of the catheter body 210. It is understood that although the interior chambers 221 and 223 illustrated in FIG. 2A are side-by-side in separate halves of the catheter body 210, other embodiments are not limited to this particular configuration. For instance, an embodiment may employ two lumens that are co-axially arranged.

Although a catheter according to the present invention may use a single interior chamber, the use of the two separate interior chambers 221 and 223 within the elongate body 210, as illustrated in FIG. 2A, is advantageous for applications, such as hemodialysis. In such applications, a first interior chamber is employed for drawing blood to be filtered from the area around the distal end 214 to a dialysis system connected at the proximal end 212. Meanwhile, a second interior chamber is employed for directing filtered blood from the dialysis system to the area around the distal end 214.

Figure 3:
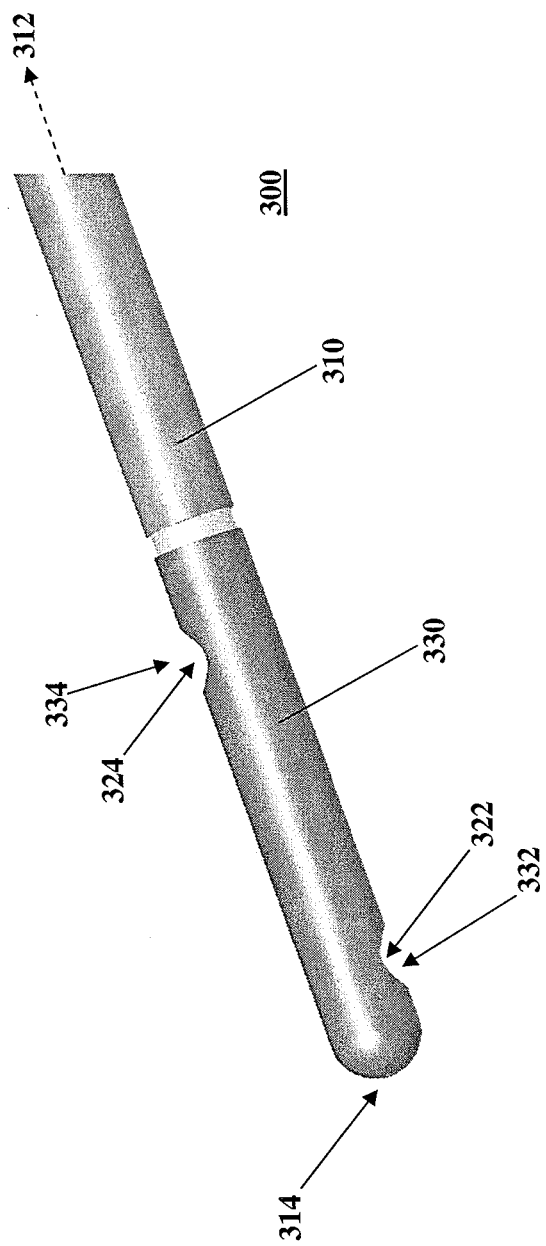
FIG. 3 illustrates a distal end of an exemplary embodiment with chamber openings spaced from the distal end of the catheter body at different distances.

Furthermore, although FIG. 2A illustrates the chamber openings 222 and 224 positioned a similar distance from the distal end 214, other embodiments of the present invention may have chamber openings positioned along the catheter body at different distances from the distal end. For instance, FIG. 3 shows a catheter 300 with chamber openings 322 and 324 for two interior chambers (not shown) that are positioned on the catheter body 310 at two different distances from the distal end 314. Advantageously, the configuration of catheter 300 makes applications, such as hemodialysis, more efficient by permitting blood to be drawn from one section of the blood vessel, and filtered blood to be delivered to a separate section of the blood vessel. In this way, the amount of mixing between filtered blood and non-filtered blood is reduced.

Referring again to FIG. 1, the valve mechanism 130 may include various forms of valve closure members which are operated by a control wire 140 which is attached to the valve mechanism 130 and extends through the elongate body 110 to the proximal end 112. The control wire 140 may be attached by techniques, which include, but are not limited to, welding, overmolding, adhesive bonding, or various types of mechanical interlocking. In addition, spading of the end of the control wire 140 may be employed to create a flatter surface on the control wire 140 to facilitate attachment of the control wire 140 to the valve mechanism 130.

According to an aspect of the present invention, the valve mechanism 130 has a cutting edge 150 that may be employed to cut away a fibrin sheath around the opening 122. The cutting edge 150 may be a thin, smooth sharpened edge. Alternatively, the edge may be textured or serrated to enable the fibrin sheath to be cut or separated into pieces. Moreover, the edge may be straight, curved, or shaped in other ways to promote cutting contact with the fibrin sheath. FIGS. 4A-8B illustrate various embodiments of the valve mechanism in accordance with the present invention.

Figure 4B:
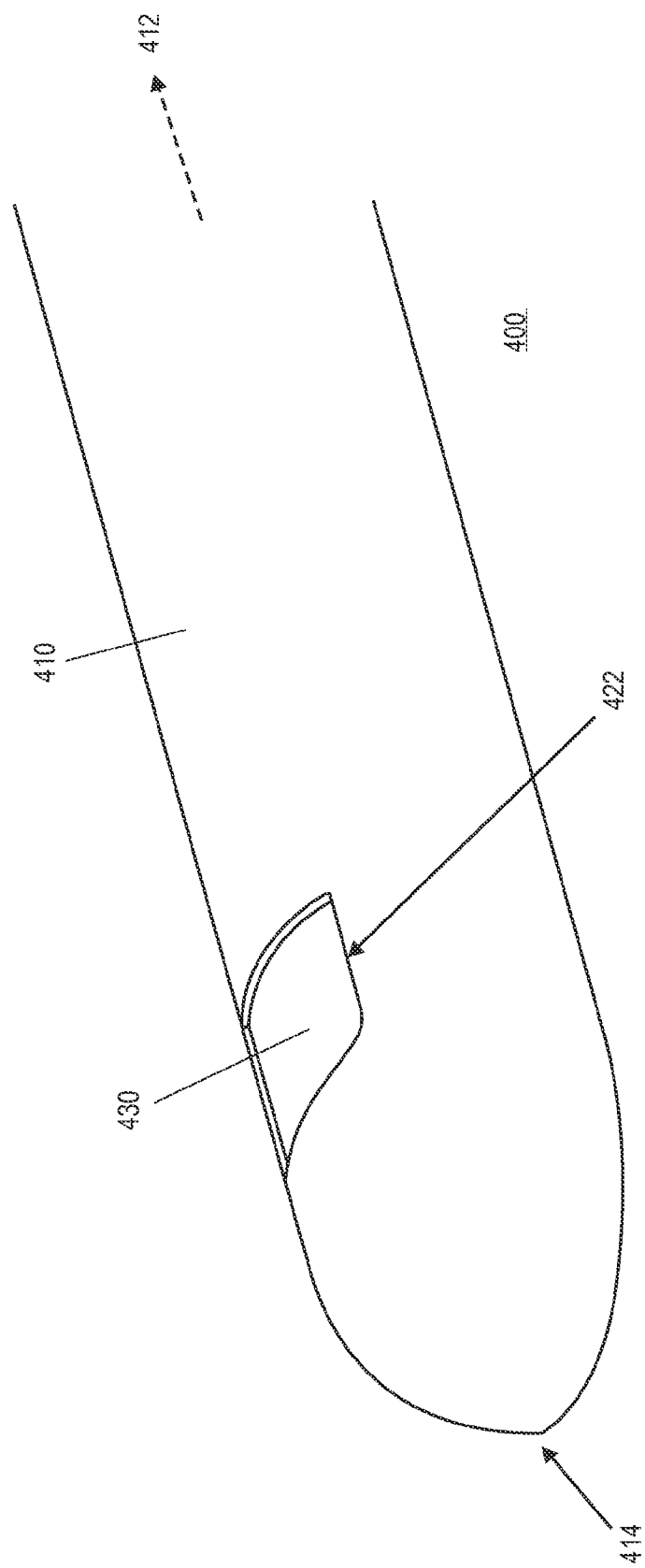
FIG. 4B illustrates the distal end of the exemplary embodiment of FIG. 4A with the gate in a closed valve position.
Figure 4C:
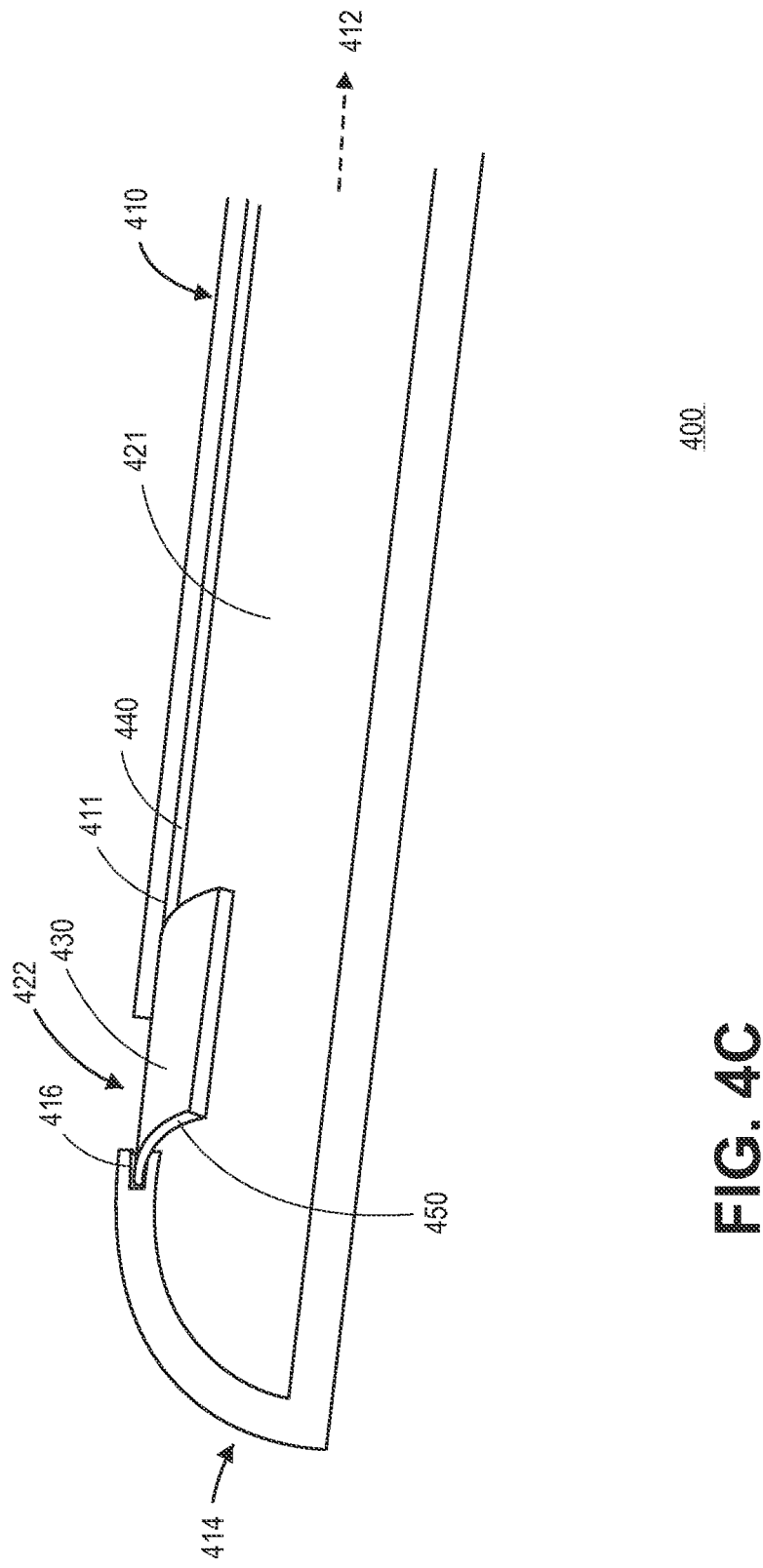
FIG. 4C illustrates a sectional view of the distal end of the exemplary embodiment of FIG. 4A with the gate in a closed valve position.

Referring to FIGS. 4A-C, a catheter 400 has an elongate catheter body 410 with a proximal end 412 and a distal end 414. The catheter 400 has an interior chamber 421 with a chamber opening 422 positioned near the distal end 414.

For a valve mechanism, the catheter 400 employs a gate 430 to control the flow rate of fluid into, or out of, the chamber opening 422. The gate 430 is shown in an open valve position in FIG. 4A. In the open valve position, fluid is permitted to flow between the interior chamber 421 and the area outside the catheter body 410 near the chamber opening 422.

On the other hand, FIG. 4B illustrates the gate 430 in a closed valve position. In the closed valve position, the gate 430 creates a barrier positioned to cover the chamber opening 422, so that flow is substantially prevented between the interior chamber 421 and the area outside the catheter body 410 near the chamber opening 422.

The operation of the gate 430 is described with reference to the sectional view FIG. 4C. The gate 430 is positioned at the chamber opening 422. In addition, the gate 430 is positioned within the interior chamber 421, against the inner surface of the catheter body wall 411. The gate 430 is operated by a control wire 440 which is connected to the gate 430 and extends through the elongate body 410 to the proximal end 412. The control wire 440 is selectively operated to move the gate 430 between the open valve position and the closed valve position. Operation of the control wire 440 moves or slides the gate 430 along the inner surface of the catheter body wall 411 in the direction shown by arrows A along the axial direction of the catheter 400. In particular, because the control wire 440 is attached to the gate 430, the control wire 440 transmits a force to the gate 430 in the axial direction. Referring to FIG. 4C, when the control wire 440 is drawn axially toward the proximal end 412, the control wire 440 draws the gate 430 toward the proximal end 412 to uncover the chamber opening 422. On the other hand, when the control wire 440 is pushed toward the distal end 414, the control wire 440 pushes the gate 430 toward the distal end 414 to cover the chamber opening 422. To ensure that the gate 430 creates a sufficient seal, the leading edge of the gate 430 enters a slot 416 positioned against the inner surface of the body wall 411, as shown in FIG. 4C.

As discussed previously, failure of hemodialysis catheter patency is frequently caused by the accumulation of obstructing thrombus or fibrin at the distal tip of the catheter, particularly after the catheter has been in place for a period of time. Movement of the gate 430 can be employed to achieve disruption and removal of any thrombus or fibrin which has accumulated over the chamber opening 422. However, axial movement of the gate 430 alone may not be sufficient to remove a fibrin sheath which is blocking or restricting flow through the chamber opening 422. As a result, the gate 430 also includes a cutting edge 450 positioned on a side of the gate 430. The cutting edge 450 may be formed by the sharpening of the gate 430 to a thin edge.

In operation, the gate 430 is moved axially to the open valve position so that the gate 430 does not cover with the chamber opening 422. Thus, any fibrin in the area outside the chamber opening 422 is accessible from the interior chamber 421. Using a syringe or other suitable device, a slight vacuum is created in the interior chamber 421 to draw the fibrin sheath through the chamber opening 422. With the fibrin sheath lying in the opening 422, the gate 430 is moved to the closed valve position where the gate 430 covers the chamber opening 422. As the gate 430 moves relative to the chamber opening 422, the cutting edge 450 positioned on the side of the gate 430 passes over the chamber opening 422 and cuts off the fibrin sheath that has been drawn through the opening 422. In particular, the cutting edge 450 acts as a leading edge and contacts the fibrin sheath within the chamber opening 422 as the gate 430 moves toward the distal end 414 into the closed valve position. The cut portions of the fibrin sheath, which now no longer inhibit flow through the opening 422, end up in the interior chamber 421 and may then be removed or flushed from the interior chamber 421 with a syringe or other suitable device.

Although the cutting edge 450 shown in FIG. 4C is positioned on the gate, alternative embodiments may employ a cutting edge positioned on the body wall 411 of the catheter 400 by the chamber opening 422. In such alternative embodiments, the cutting edge on the body wall 411 meets the leading edge of the gate when the gate is in the closed valve position. As the gate moves into the closed valve position, the gate contacts the fibrin sheath in the chamber opening 422 with the leading edge of the gate and pushes the fibrin sheath against the cutting edge on the body wall 411 causing the fibrin sheath to be cut. Accordingly, in general the cutting edges of the valve mechanisms in embodiments of the present invention may be positioned by, or adjacent to, the chamber opening. As such, the cutting edges may be on the catheter body and/or the valve body, such as a gate.

Figure 4E:
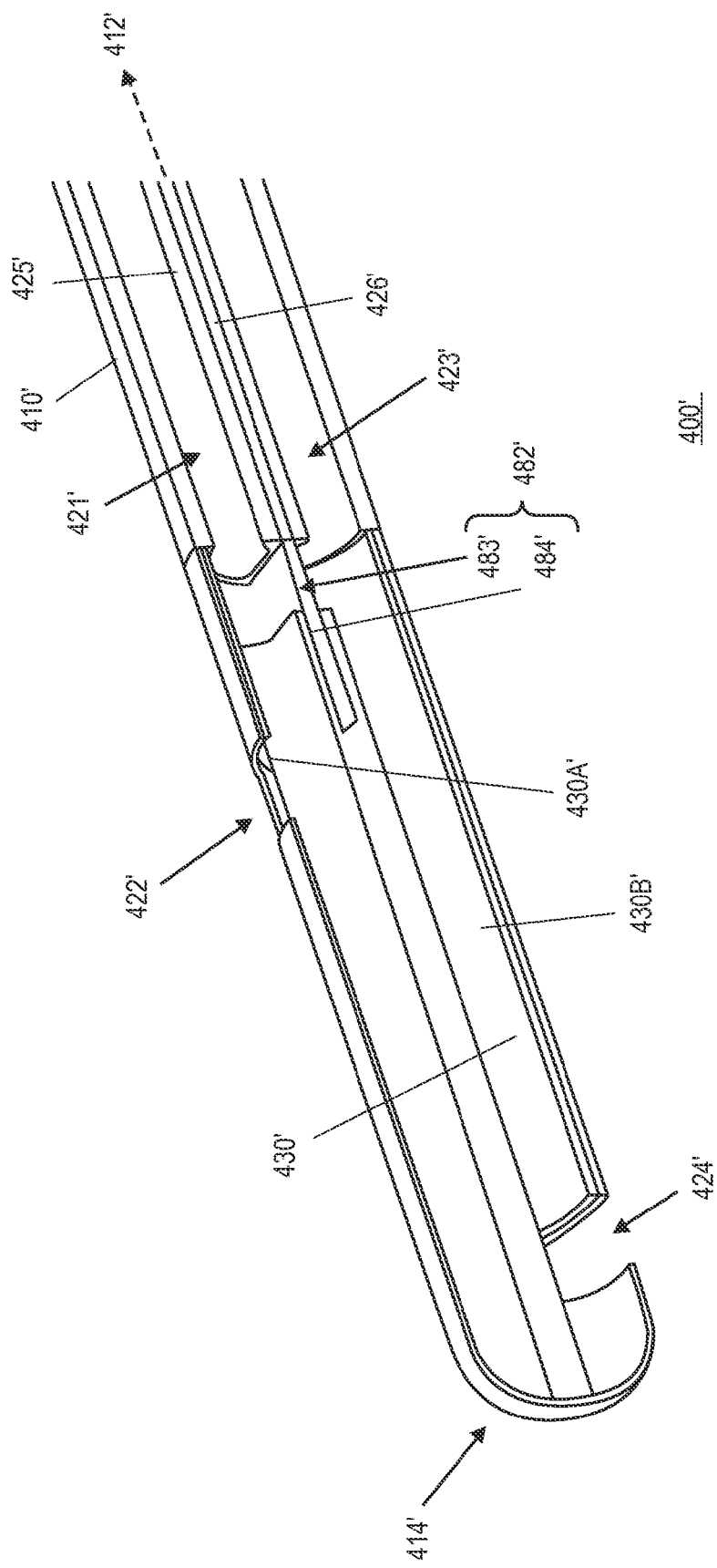
FIG. 4E illustrates a cross-sectional view of the exemplary embodiment of FIG. 4E with the gates each in an open valve position.
Figure 4F:
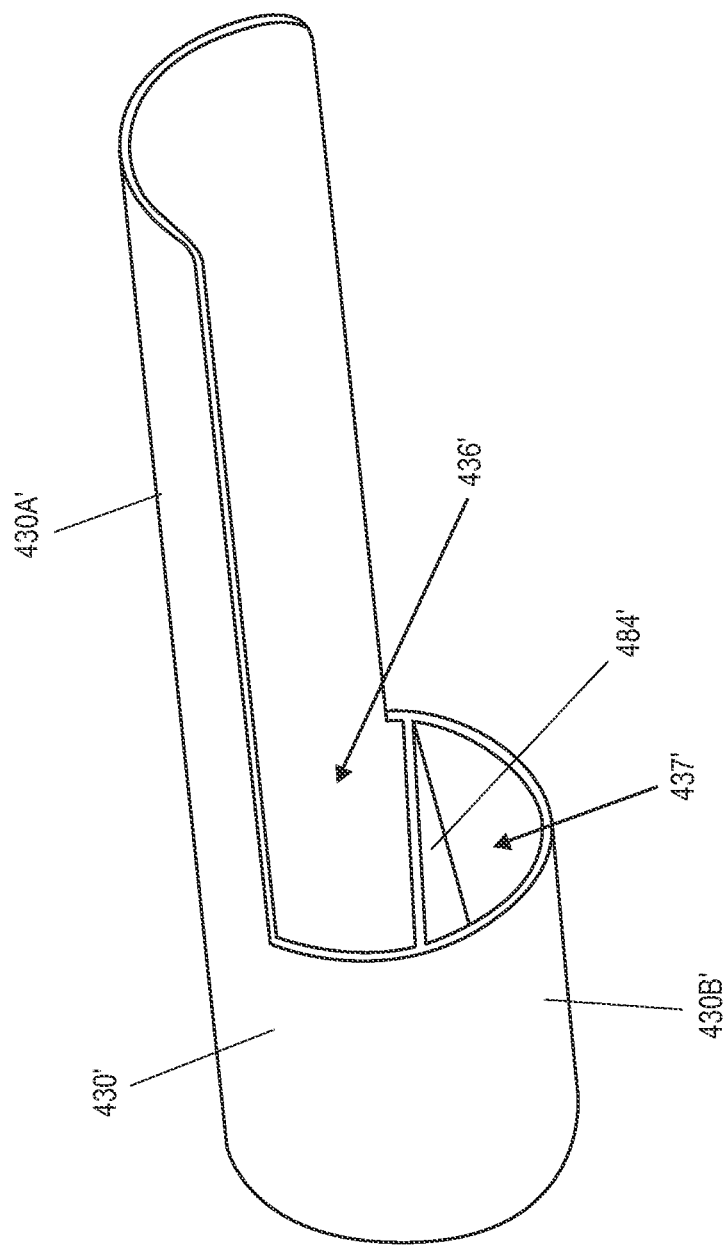
FIG. 4F illustrates an exemplary embodiment of a gate for use with a connecting valve connecting two interior chambers of a catheter body.

While the catheter 400 illustrated in FIGS. 4A-C may have one interior chamber 421 with a single gate 430, the alternative embodiment shown in FIGS. 4D-F illustrates a catheter 400' that has two interior chambers 421' and 423' and two gates 430A' and 430B' to control the flow of fluid through the chamber openings 422' and 424'. The interior chambers 421' and 423' extend from a proximal end 412' to a distal end 414'. In addition, the interior chambers 421' and 423' have the chamber openings 422' and 424', respectively, positioned near the distal end 414'. However, the chamber openings 422' and 424' are positioned at different distances from the distal end 414'. FIG. 4D shows the gates 430A' and 430B' each in a closed valve position. On the other hand, FIG. 4E shows the gates 430A' and 430B' each in an open valve position. As more clearly shown in FIG. 4F, the gates 430A' and 430B' may be part of the same body 430'. As such, gates 430A' and 430B' move together with operation of body 430'. In particular, in the present embodiment, the gates 430A' and 430B' move together from the closed valve positions, shown in FIG. 4D, to the open valve positions, shown in FIG. 4E, when the body 430' is drawn longitudinally by corresponding movement of the control wire (not shown) toward the proximal end 412'. Conversely, the gates 430A' and 430B' move together from the open valve positions to the closed valve positions when the body 430' is driven longitudinally by corresponding movement of the control wire in the reverse direction toward the distal end 414'. Further details regarding body 430' are provided hereinbelow. Although the embodiments shown in FIGS. 4A-F have gates that move longitudinally, it is understood that the gate in alternative embodiments may move in another direction, e.g. along a plane substantially transverse to a longitudinal line of the catheter body.

Figure 5A:
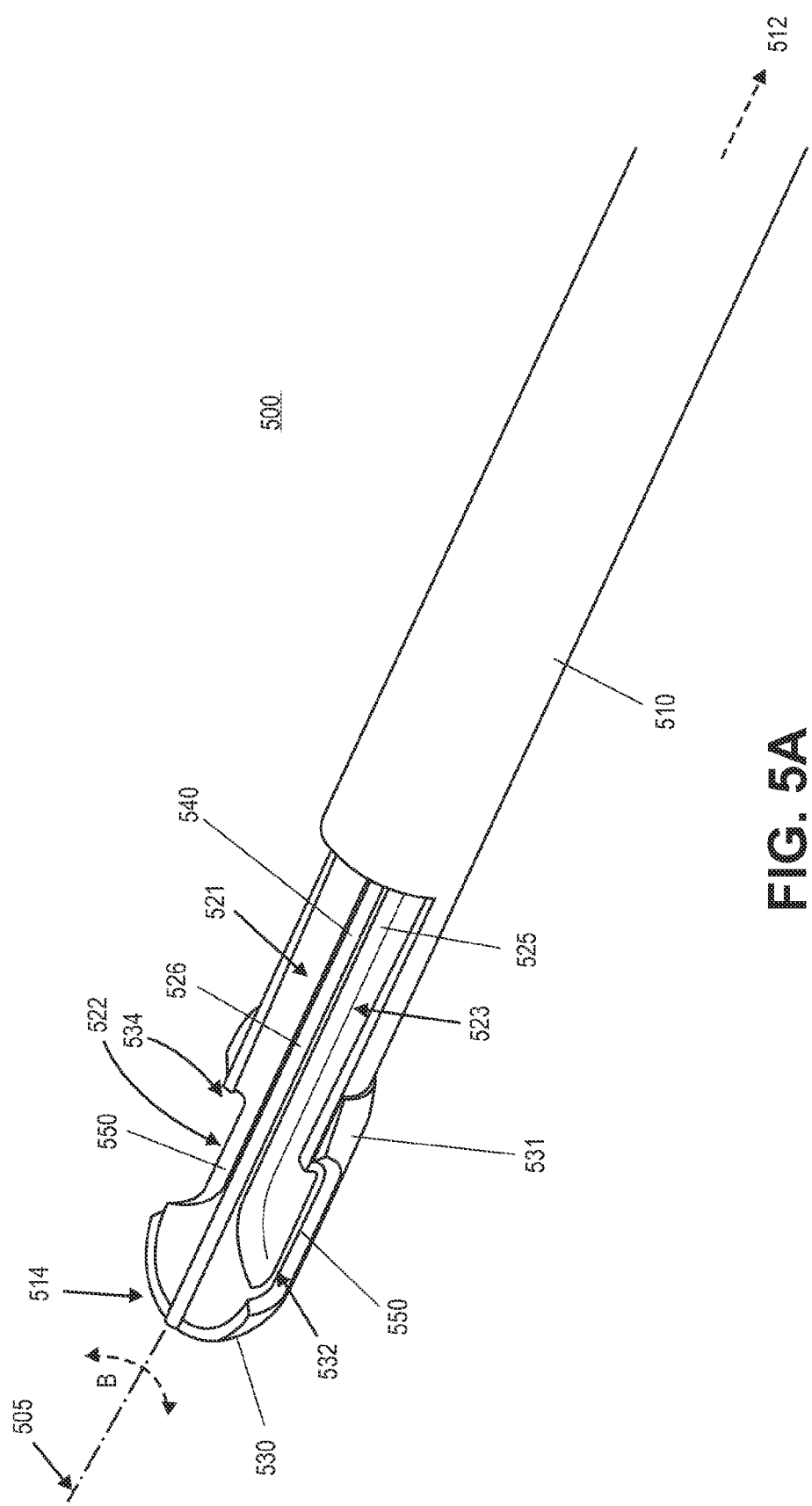
FIG. 5A illustrates a sectional view of a distal end of an exemplary embodiment with a rotating cap-shaped valve in an open valve position.
Figure 5B:
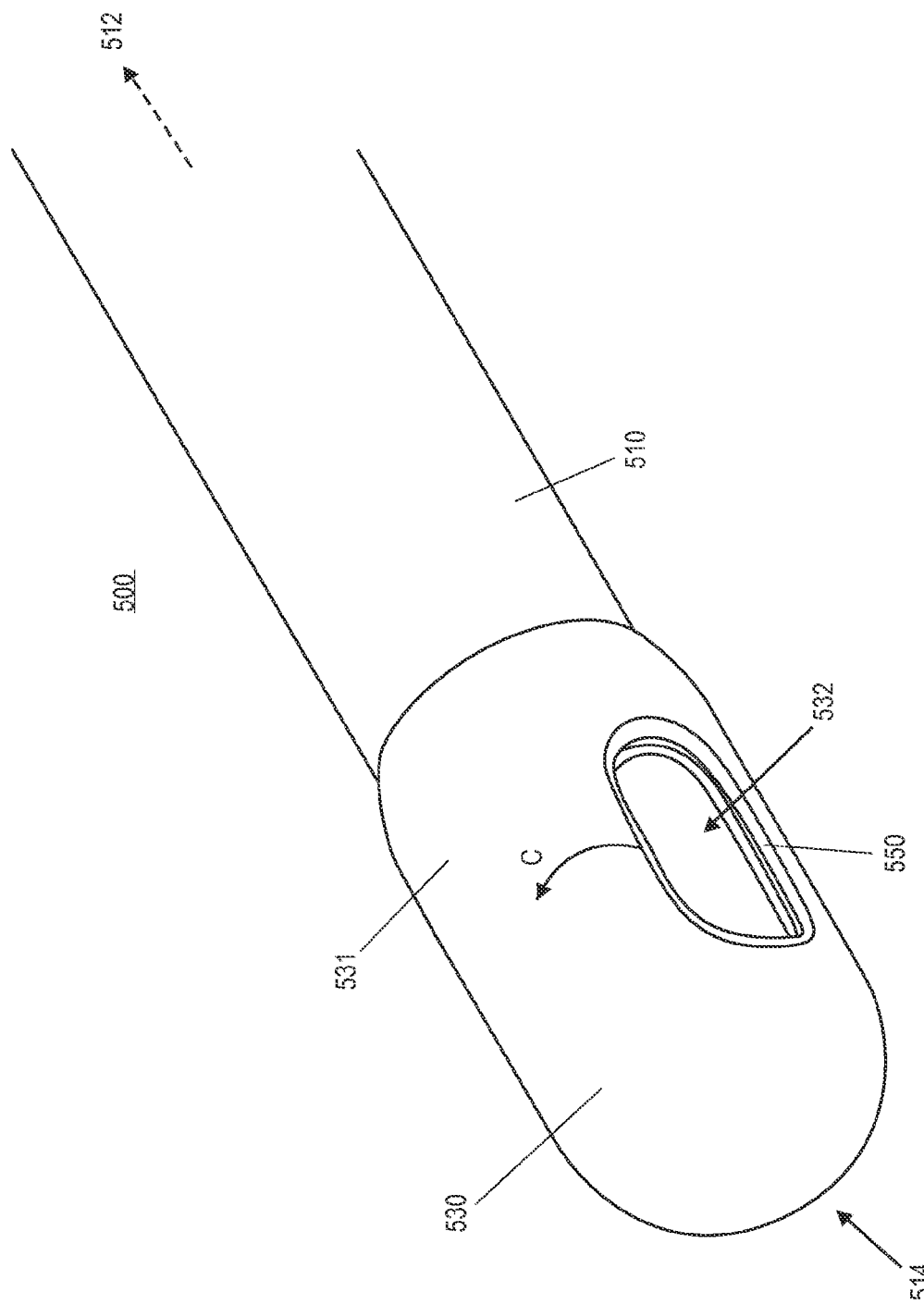
FIG. 5B illustrates the distal end of the exemplary embodiment of FIG. 5A with the cap-shaped valve in a closed valve position.

FIGS. 5A-B illustrate an alternative to the gate 430 described previously. The exemplary embodiment of FIGS. 5A-B employs a cap-shaped valve 530. Referring to FIG. 5A, a catheter 500 has a cap 530 at the distal end 514 of an elongate catheter body 510. The catheter body 510 has two interior chambers 521 and 523. A dividing wall 525 extends longitudinally along the catheter body 510 to separate two halves of the catheter body 520 and define the two interior chambers 521 and 523. The interior chamber 521 has a chamber opening 522 near the distal end 514, and similarly, the interior chamber 523 has a chamber opening 524 near the distal end 514. As illustrated in FIG. 5A, the cap 530 has two cap openings 532 and 534, which are defined by a cap wall 531 and which are aligned with the chamber openings 522 and 524, respectively. With the open valve position of the cap 530 shown in FIG. 5A, the chamber opening 522 and the cap opening 532 open the interior chamber 521 to the area outside the cap opening 532, and fluid is able to flow between the interior chamber 521 and the area outside the cap opening 532. Similarly, the chamber opening 524 and the cap opening 534 open the interior chamber 523 to the area outside the cap opening 534, and fluid is also able to flow between the interior chamber 523 the area outside the cap opening 534.

The cap 530 moves from the open valve position to a closed valve position by rotating relative to the catheter body 510 about a longitudinal line 505. The rotation may occur in one of the directions depicted by the arrows B in FIG. 5A. The cap openings 532 and 534 are defined by a cap wall 531. When the cap openings 532 and 534 are not aligned with the chamber openings 522 and 524, respectively, portions of the cap wall 531 act as barriers positioned to cover the chamber openings 522 and 524. When the cap openings 532 and 534 and the chamber openings 522 and 524 are completely misaligned, the chamber openings 522 and 524 are completely covered. With the chamber openings 522 and 524 blocked by the cap wall 531, fluid flow is substantially prevented between the interior chambers 521 and 523 and the passageway outside the catheter 500.

FIG. 5A also illustrates a control wire 540 that is connected to an inner portion of the cap 530 at the distal end 514. The control wire extends from the distal end 514 to the proximal end 512. The control wire 540 is operated to move the cap 530 between the open valve position and the closed valve position. In particular, the rotation of the control wire 540 transmits a rotational force to the cap 530 to open or close the chamber openings 522 and 524 by virtue of the control wire 540 being attached, preferably to the center of the cap 530.

As further illustrated in FIG. 5A, the control wire 540 is positioned in a control wire channel 526, which extends from the proximal end 512 to the distal end 514 within the dividing wall 525. The control wire channel 526 is dimensioned to permit rotation of the control wire 540, and may accommodate the use of a lubricant to facilitate motion of the control wire while substantially preventing any escape of the lubricant from the channel 526.

Referring again to FIG. 2A, a further example of a control wire channel is illustrated. In particular, the control wire channel 226 is positioned within a longitudinal dividing wall 225 of the catheter body 210. FIG. 2B shows a sectional view of the catheter body 210, where the dividing wall 225 divides the catheter body into two halves to define the interior chambers 221 and 223. The control wire 240 passes through the control wire channel 226 formed within the dividing wall 225. As shown further in FIG. 2B, the control wire 240 may have a tube-shaped body 242 with a septum valve (not shown) at both proximal and distal ends. A guide wire channel 243 is formed in the tube-shaped body 242. As such, in order to facilitate catheter positioning, the implanting physician extends a guide wire 244 to a location in a body passageway. The guide wire 244 is then positioned within the guide wire channel 243 through the center of the tube body 242, and the catheter body 210 is guided along the guide wire 244 to the location in the body passageway. Once the catheter body 210 is positioned in the body passageway, the guide wire 244 can be extracted. Upon guide wire removal, a permanent plug may be inserted into the proximal end of the tube body 242 to close the guide wire channel 243 and prevent air embolism and/or blood loss. To further facilitate proper positioning of the catheter body 210 within the body passageway, the guide wire 244 may include, near the distal end of the guide wire 244, a centering mechanism, such as a plurality of elongate legs defining an expanding centering basket.

As discussed previously, failure of hemodialysis catheter patency is frequently caused by the accumulation of obstructing thrombus or fibrin at the distal tip of the catheter, particularly after the catheter has been in place for a period of time.

In some instances, mere rotation of the cap 530 can be employed to achieve disruption and removal of any thrombus or fibrin which has accumulated over the cap 530. However, merely rotating the cap 530 may not be sufficient to remove a fibrin sheath which is blocking or restricting flow through the chamber openings 522 and 524. As a result, the cap 530 also includes cutting edges 550 positioned on the inner edge of the cap openings 532 and 534. For example, a cutting edge 550 on the cap opening 532 is shown in closer detail in FIG. 5B. The cutting edge 550 may be formed by the sharpening of the cap wall 531 of the cap 530 to a thinner edge at the cap opening 532.

In operation, the cap 530 is rotated to the open valve position in order to bring the cap openings 532 and 534 into alignment with the chamber openings 522 and 524, respectively. Thus, any fibrin in the area outside the cap openings 532 and 534 is accessible from the interior chambers 521 and 523. Using a syringe or other suitable device, a slight vacuum is created in the chambers 521 and 523 to draw the fibrin sheath through the cap openings 532 and 534 and the chamber openings 522 and 524, respectively. With the fibrin sheath lying in these openings, the cap 530 is rotated to the covered position to move the cap openings 532 and 534 out of alignment with the chamber openings 522 and 524. As the openings 532 and 534 rotate relative to the chamber openings 522 and 524, the cutting edges 550 positioned on the inner edge of the cap openings 532 and 534 pass over the chamber openings 522 and 524 and cut off the fibrin sheath that has been drawn through these openings. For example, as shown in FIG. 5B, the cutting edge 550 acts as a leading edge as the cap 530 moves in the direction of arrow C into the closed valve position. In this way, the sharpened part is guided into contact with the fibrin sheath. The cut portions of the fibrin sheath, which now no longer inhibit flow through the openings, end up in the interior chambers 521 and 523 and may then be removed or flushed from the interior chambers 521 and 523 with a syringe or other suitable device.

Figure 6B:
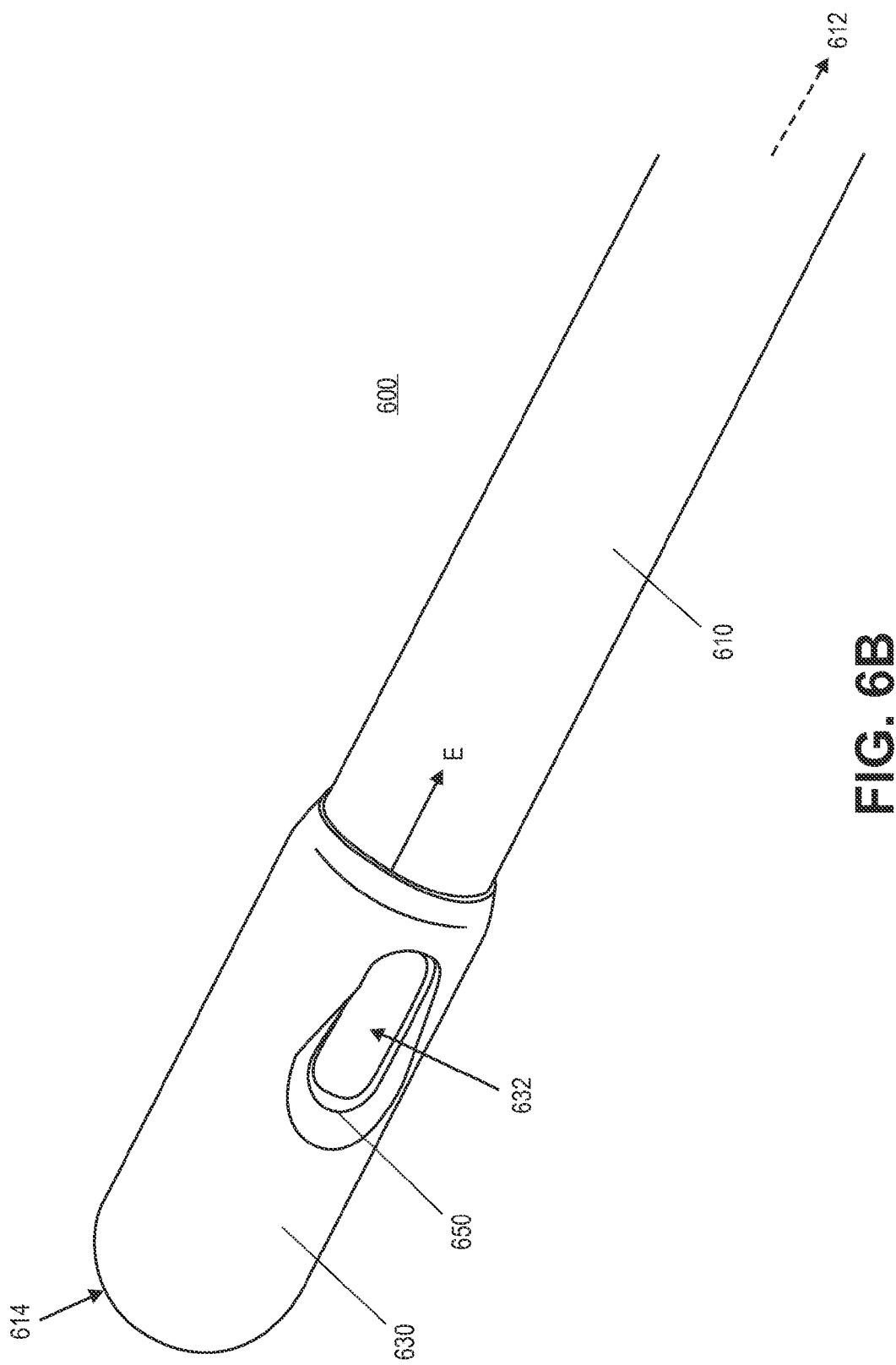
FIG. 6B illustrates the distal end of the exemplary embodiment of FIG. 6A with the cap-shaped valve in a closed valve position.

A further embodiment of a valve mechanism is illustrated in FIGS. 6A-B. The embodiment provides a catheter 600 which employs the cap 630 to act as the valve mechanism to control the flow of fluid during operation of the catheter 600. The cap 630 is mounted on the distal end 614 of an elongate catheter body 610. An interior dividing wall 625 extending longitudinally along the catheter body 610 defines two interior chambers 621 and 623. The interior chamber 621 has a chamber opening 622 near the distal end 614, and similarly, the interior chamber 623 has a chamber opening 624 near the distal end 614. The cap 630 has two cap openings 632 and 634 which are defined by cap wall 631. As illustrated in FIG. 6A, the cap openings 632 and 634 are not aligned with the chamber openings 622 and 624, so that the portions of the cap wall 631 act as barriers to cover the chamber openings 622 and 624. The orientation of the cap 630 shown in FIG. 6A corresponds with a closed valve position.

Although the catheter 600 uses a cap as a valve mechanism, the catheter 600 differs from the catheter 500 described above. When the cap 630 moves between the open and closed valve positions, it moves, or translates, axially along the longitudinal axis 605, instead of rotating like the cap 530. In other words, the cap 630 moves in the direction of the arrows D shown in FIG. 6A.

Accordingly, in order to move from the closed valve position to the open position, the cap 630 moves relative to the elongate catheter body 610 in the axial direction toward the distal end 614 until the cap openings 632 and 634 align with the chamber openings 622 and 624, respectively. In this open valve position, fluid is able to flow between the interior chamber 621 and the area outside the cap opening 632. Similarly, fluid is able to flow between the interior chamber 623 and the area outside the cap opening 634. To achieve the closed valve position again, the cap 630 is moved in the axial direction toward the proximal end 612 until the cap openings 632 and 634 are no longer aligned with the chamber openings 622 and 624, respectively.

The cap 630 is controlled by a control wire 640 that is connected to an inner portion of the cap 630 at the distal end 614. The control wire 640 is positioned within a control wire channel 626 in the dividing wall 625 and extends from the distal end 614 to the proximal end 612. The control wire 640 is operated to move the cap 630 between the open valve position and the closed valve position. In particular, the control wire 640 transmits an axial force to the cap 630 to open or close the chamber openings 622 and 624.

Axial movement of the cap 630 can be employed to achieve disruption and removal of any thrombus or fibrin which has accumulated over the cap 630. However, if this axial movement of the cap 630 alone is not be sufficient to remove a fibrin sheath, cutting edges 650 positioned on the inner edge of the cap openings 632 and 634 may be employed. For example, a cutting edge 650 on the cap opening 632 is shown in closer detail in FIG. 6B. The cutting edge 650 is formed by the sharpening of the cap wall 631 of the cap 630 to a thinner edge at the cap opening 632.

In operation, the cap 630 is moved axially to the open valve position in order to bring the cap openings 632 and 634 into alignment with the chamber openings 622 and 624, respectively. Using a syringe or other suitable device, a slight vacuum is created in the chambers 621 and 623 to draw the fibrin sheath through the cap openings 632 and 634 and the chamber openings 622 and 624, respectively. With the fibrin sheath lying in these openings, the cap 630 is moved axially to the closed valve position to move the cap openings 632 and 634 out of alignment with the chamber openings 622 and 624. As the openings 632 and 634 rotate relative to the chamber openings 622 and 624, the cutting edges 650 positioned on the inner edge of the cap openings 632 and 634 pass over the chamber openings 622 and 624 and cut off the fibrin sheath that has been drawn through these openings. For example, as shown in FIG. 6B, the cutting edge 650 acts as a leading edge as the cap 630 moves in the direction of arrow E into the closed valve position. In this way, the sharpened part is guided into contact with the fibrin sheath. The cut portions of the fibrin sheath, which now no longer inhibit flow through the openings, end up in the interior chambers 621 and 623 and may then be removed or flushed from the interior chambers 621 and 623 with a syringe or other suitable device.

In the manner previously noted, the cap may be implemented with chamber openings that are positioned at different distances from the distal end. In this regard, the embodiment of FIG. 3 provides a catheter 300 with chamber openings 322 and 324 for two interior chambers, the openings being positioned at two different distances from the distal end 314. The cap 330 may either rotate or move axially to move between the closed valve position and the open valve position.

In addition to the gate valve and the cap-shaped valves described above, other valve mechanisms may be employed with the present invention. For instance, FIGS. 7A-B illustrate a catheter body 700 that has a single interior chamber 721 that has an enlarged chamber opening 722 at the distal end 714 of the catheter body 710. Of course, the catheter body 700 may alternatively be implemented to have multiple co-axial chambers sharing the same opening 722 in other embodiments. The chamber opening 722 is selectively opened or closed by the axial movement of a valve plug 730 connected to a control wire 740. The control wire 740 may be operated from a proximal end 712, as described further below. FIG. 7A shows the catheter 700 with the valve plug 730 in an open valve position, while FIG. 7B shows the catheter 700 in a closed valve position. The valve plug 730 is formed with a rear section 732 that tapers to a smaller dimension at the rear. The rear section 732 fits into and closes the chamber opening 722. A rounded forward section 735 forms a bullet shaped nose for the catheter body 710. Advantageously, the rounded section 735 reduces blood flow turbulence. Moreover, the shape minimizes contact of the most distal segment of the catheter with native tissue when the catheter is in place.

The valve plug 730 may be moved back and forth relative to the chamber opening 722 to disrupt any thrombus or fibrin which has accumulated over the distal end 714 of the catheter body 710. A cutting edge 750 is employed along the edge of the chamber opening 722 to cut the fibrin sheath. To cut the fibrin sheath, the valve plug 730 is moved into the closed valve position after the fibrin sheath has been drawn into the interior chamber 721 with a slight vacuum.

The catheter 800 of FIGS. 8A-B is similar to catheter 700 because it also employs a valve plug 830. However, the catheter 800 has two side-by-side interior chambers 821 and 823 with chamber openings 822 and 824, respectively. As such, the valve plug 830 has two rear sections 832 and 834 that taper to a smaller dimension at the rear. The rear sections 832 and 834 fit into and close the chamber openings 822 and 824, respectively. As illustrated in FIG. 8A, the chamber openings 822 and 824 are positioned at different distances from the distal end 814 of the catheter 800. Therefore, the valve plug 830 is shaped accordingly so that the tapered rear surface 834 extends farther from the distal end 814 than the tapered rear surface 832. However, the valve plug 830 maintains a rounded front section 835 which advantageously forms a bullet shaped nose for the catheter body 810.

The chamber openings 822 and 824 are selectively opened or closed by the axial movement of a valve plug 830 connected to a control wire 840. The control wire 840 may be operated from a proximal end 812, as described further below. FIG. 8A shows the valve plug 830 in the open valve position, while FIG. 8B shows the valve plug 830 in the closed valve position. The valve plug 830 may be moved back and forth relative to the chamber openings 822 and 824 to disrupt any thrombus or fibrin which has accumulated in the area of the chamber openings 822 and 824. Moreover, cutting edges 850 may be employed along the edges of the chamber openings 822 and 824 to cut the fibrin sheath. To cut the fibrin sheath, the valve plug 830 is moved into the closed valve position after the fibrin sheath has been drawn into the interior chambers 821 and 823 with a slight vacuum.

Figure 9A:
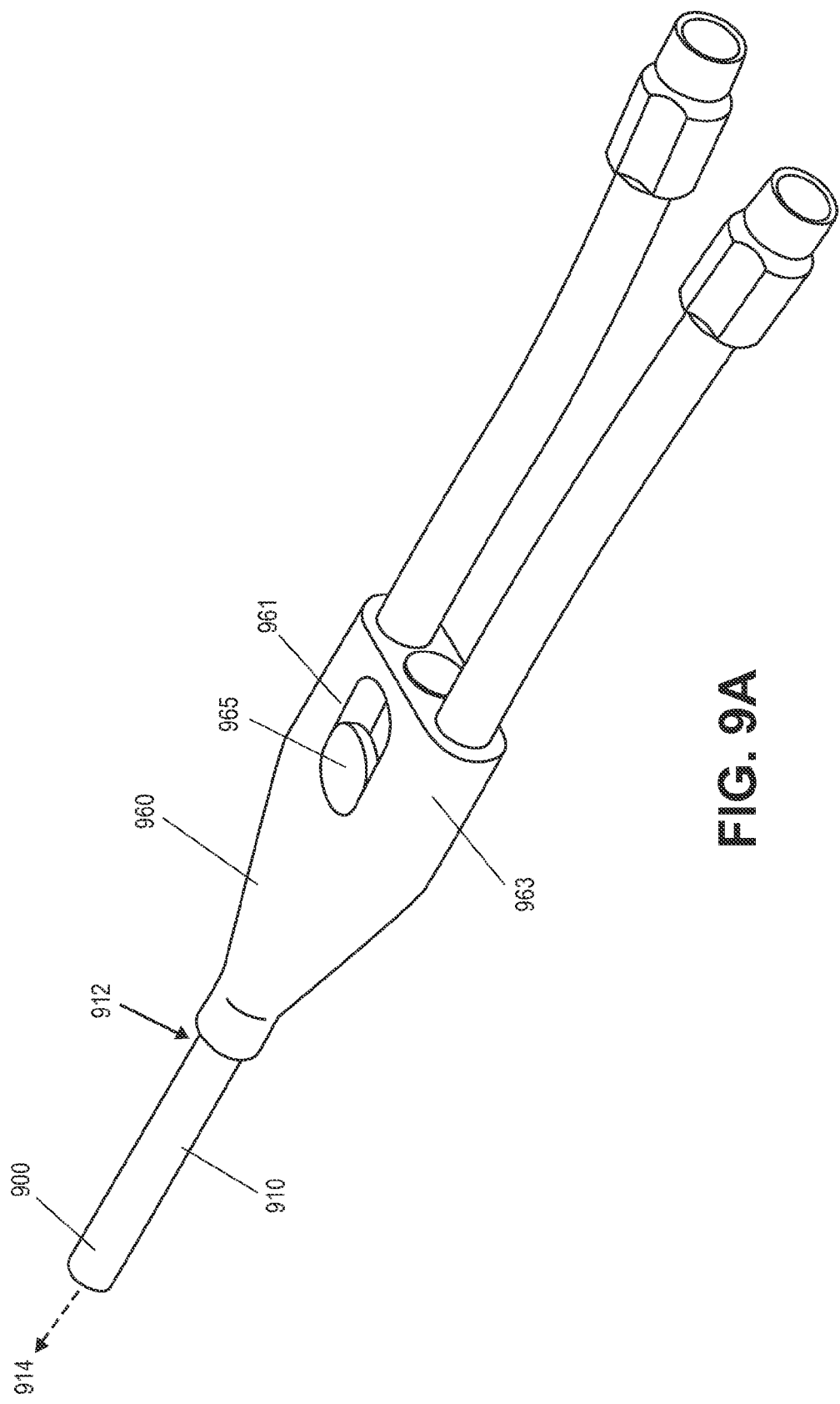
FIG. 9A illustrates an exemplary embodiment with a hub at the proximal end.
Figure 9B:
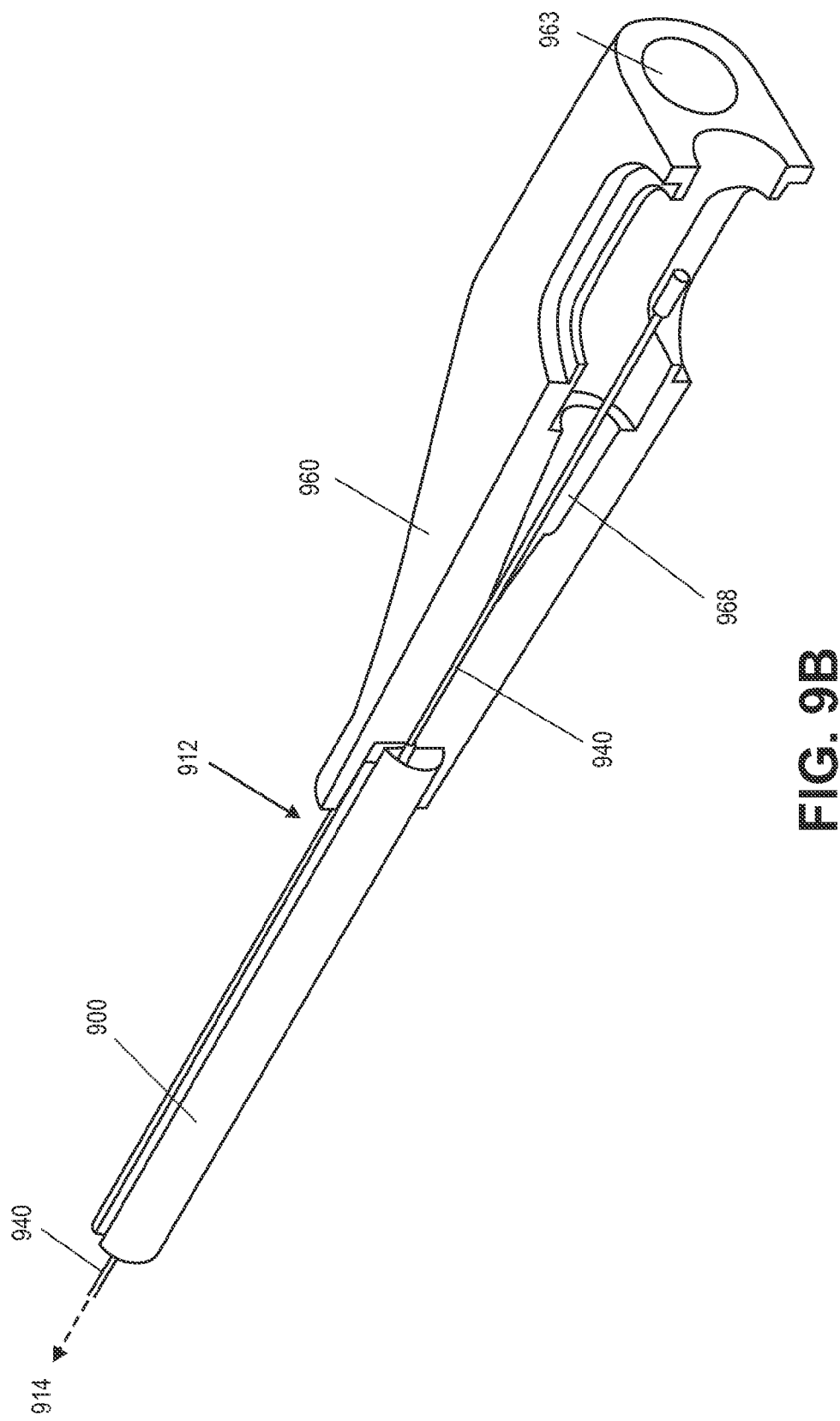
FIG. 9B illustrates a sectional view of the exemplary embodiment of FIG. 9A.

As described previously, each of the valve mechanisms of the exemplary embodiments above may be selectively actuated by a control wire that extends from the valve mechanism at the distal end to the proximal end of the catheter. The control wire may be operated by the operator from the proximal end of the catheter. Accordingly, FIGS. 9A-B illustrate a proximal hub 960 which is secured to the proximal end 912 of a catheter 900. The catheter 900 has two interior chambers (not shown) extending from the distal end 914 to the proximal end 912 of the catheter 900. The proximal hub 960 includes a fluid port 961 in communication with one interior chamber and a fluid port 963 in communication with the other interior chamber. From the interior chambers, the fluid ports 961 and 963 may lead to a supply of fluid to be introduced into the interior chambers, or may lead to a receiving system to deposit fluid drawn from the body passageway.

Moreover, the proximal hub 960 has a control mechanism 965, such as a button, that is connected to, and operates, the control wire 940, as shown in FIG. 9B. The operator moves the control button 965 to cause corresponding movement of the control wire 940. To maintain a sufficient seal between the control wire 940 and the hub 960, the control wire 940 and hub 960 are attached to a rolling membrane 968. The rolling membrane 968 acts as an inverting bellow which allows the control wire 940 to move, particularly in the axial direction, while maintaining a seal between the control wire 940 and the hub 960. The rolling membrane may be formed from a flexible material, such as silicone, polyurethane, or other elastomer.

Figure 10:
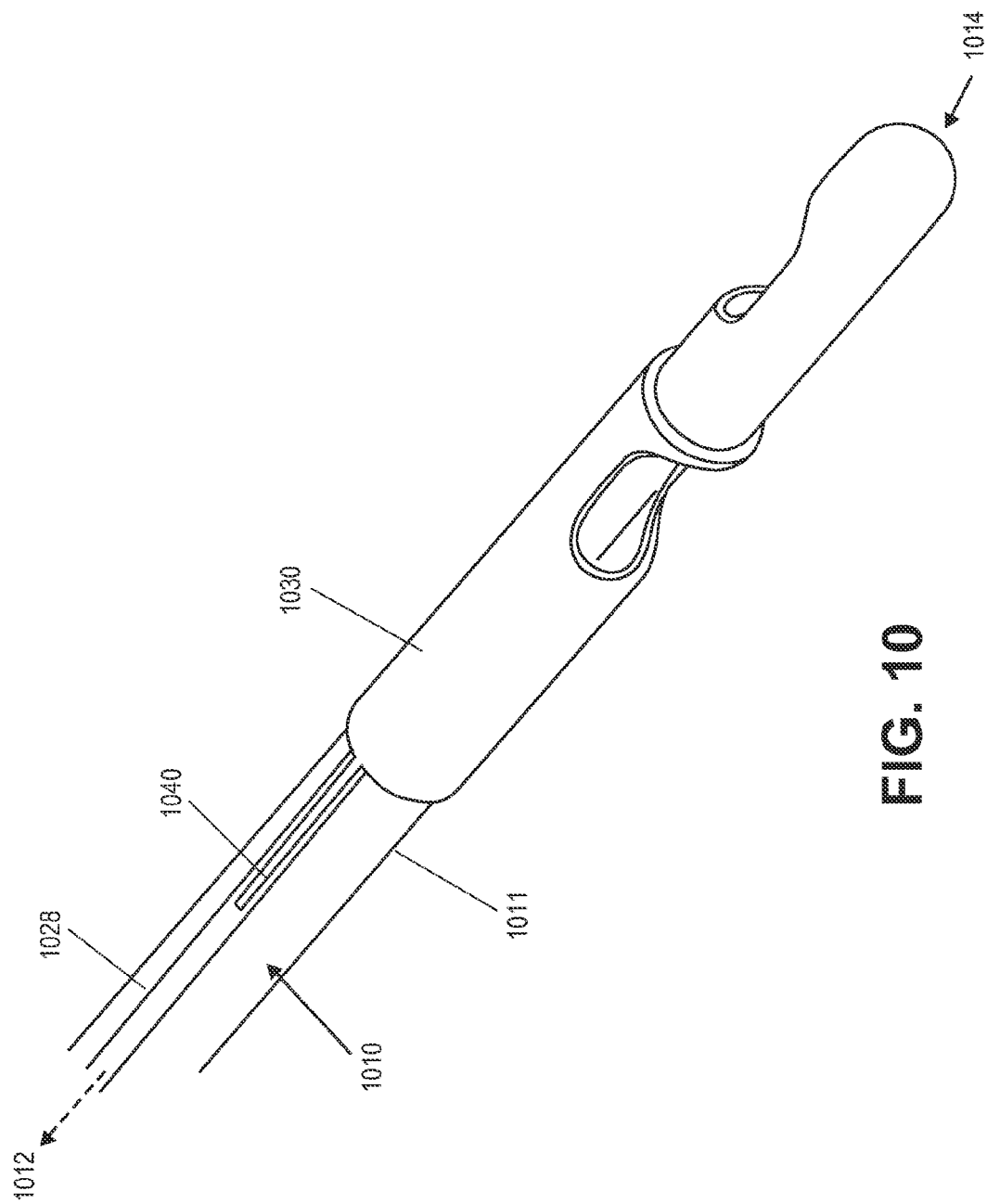
FIG. 10 illustrates an exemplary embodiment with an external control wire.

The embodiments described above employ a control wire that extends through the interior of the catheter body. However, as shown in FIG. 10, an embodiment of the present invention may employ a control wire 1040 that is positioned in a control wire channel 1028 that is not located within an interior dividing wall. The control wire channel 1028 in FIG. 10 is connected to a valve mechanism 1030 at the distal end 1014 and extends along the body wall 1011 of the catheter body 1010 to the proximal end 1012.

Figure 11A:
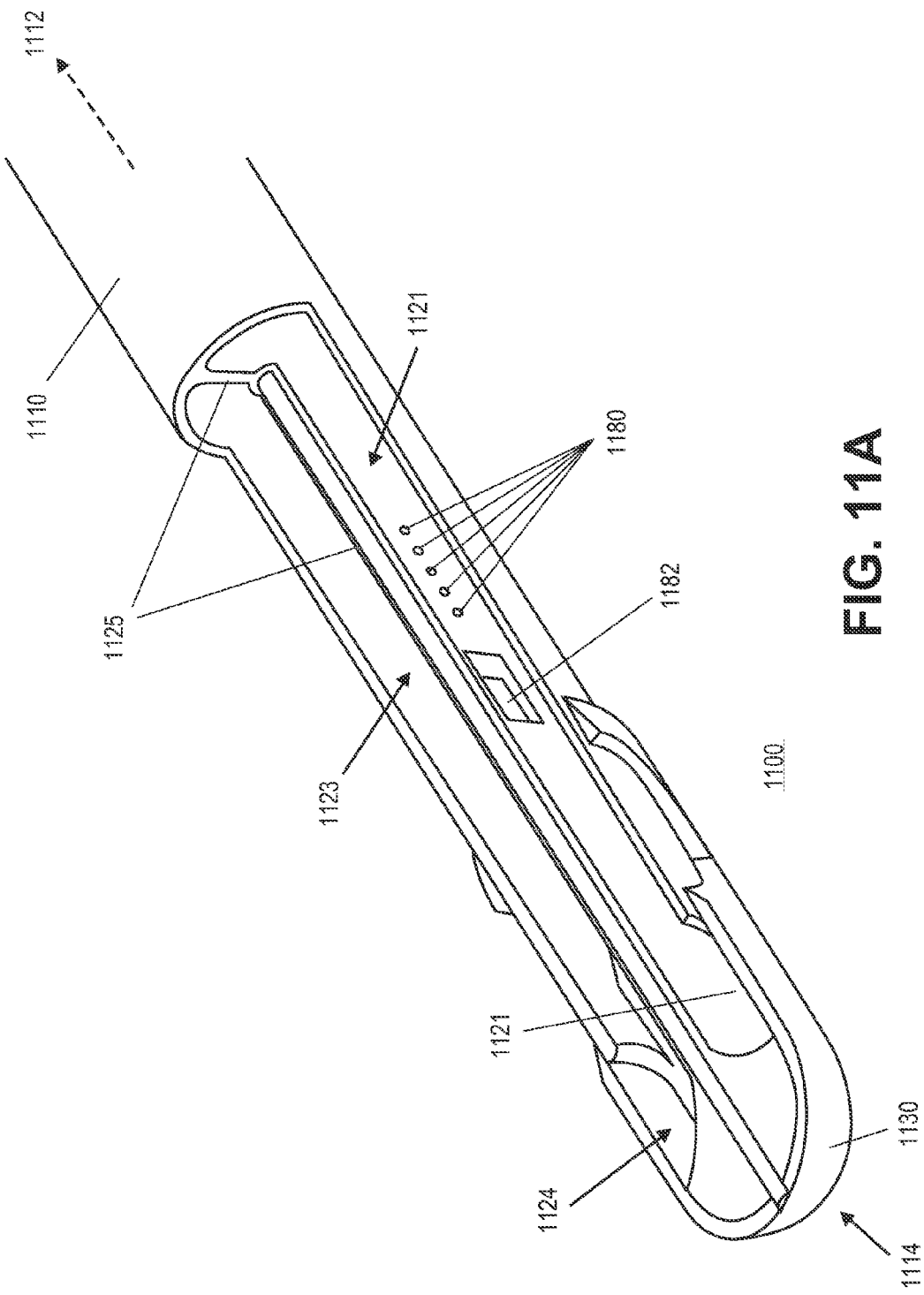
FIG. 11A illustrates an exemplary embodiment with micro-holes and a connecting valve connecting two interior chambers.

As described previously, a dangerous catheter complication is infection caused by microbial colonization on the catheter. As a result, it may be advantageous to provide a continuous flush through the interior chamber(s) of the catheter. In particular, the interior chambers may be flushed with an anti-microbial fluid. A catheter 1100 with two interior chambers 1121 and 1123 is shown in FIG. 11A. The catheter 1100 employs micro-holes 1180 that extend through the dividing wall 1125 defining the interior chambers 1121 and 1123. The micro-holes 1180, for example, may have a diameter in the range of approximately 0.015 to 0.050 inches. Although FIG. 11A illustrates the micro-holes 1180, other embodiments may employ other types of fluidic connecting channels between the two interior chambers 1121 and 1123. For instance, an embodiment may employ a slit-shaped opening defined by a longitudinal cut through the dividing wall 1125.

Furthermore, other embodiments may employ at least one connecting valve 1182 that also extends through the dividing wall 1125. The connecting valve 1182 may be selectively operated from the proximal end with an auxiliary control wire (not shown) to open a connecting valve wall (not shown) and fluidically connect the interior chambers 1121 and 1123 together.

As shown in FIG. 11A, the connecting valve 1182 may be used in combination with the micro-holes 1180. The micro-holes 1180 and the connecting valve 1182, therefore, fluidically connect the two interior chambers 1121 and 1123. When the valve mechanism 1130 moves into the closed valve position and blocks flow through the chamber openings 1122 and 1124, the introduction of a flushing fluid into the interior chambers 1121 and 1123 results in micro-distal tip communication. In other words, fluid passes through the micro-holes 1180 and/or the connecting valve 1182, causing fluid circulation through the interior chambers 1121 and 1123 without systemic spillage. As described previously, the valve mechanism in the present invention, in the closed valve position, substantially prevents or minimizes the loss of fluid from interior chambers of the catheter. Thus, when a continuous flush is introduced through catheter 1100, the valve mechanism 1130 substantially prevents the flushing fluid in the interior chambers 1121 and 1123 from entering the body passageway, or fluid from the body passageway, such as blood, from entering the interior chambers 1121 and 1123. Without the barrier created by the valve mechanism 1130, any density gradient between fluid in the passageway and fluid in the interior chambers 1121 and 1123 would cause unwanted exchange of fluid between the passageway and the interior chambers 1121 and 1123. Furthermore, the valve mechanism 1130 substantially prevents vacuum loss by the entrance of fluid from the passageway and permits a sufficient vacuum to be created within the interior chambers to initiate flushing through the interior chambers 1121 and 1123.

In addition to permitting aggressive catheter flushing, the micro-holes 1180 or the connecting valve 1182 facilitate the removal of fluid from the catheter 1100 when the chamber openings 1122 and 1124 are closed by the valve mechanism 1130. The fluidic communication between the interior chambers 1121 and 1123 enabled by the micro-holes 1180 and/or the connecting valve 1182 helps to prevent a vacuum from forming within any one of the interior chambers 1121 and 1123 when the fluid is withdrawn from the chamber, for example, with a syringe at the proximal end 1112 of the catheter. Fluid or air in one chamber is drawn through the micro-holes 1180 and/or the connecting valve 1182 into the second chamber to help prevent a vacuum from forming in the second chamber. A formation of a vacuum within the interior chamber would otherwise resist the withdrawal of fluid from the interior chamber.

An embodiment of a connecting valve is illustrated with the catheter 400' in FIGS. 4D-F. The catheter 400' has a connecting valve 482' that fluidically connects the interior chambers 421' and 423' with a closable interior valve opening 483' in the dividing wall 425'. The valve opening 483' is opened and closed by operation of the interior gate 484'. As shown in FIG. 4F, the interior gate 484' may be formed with the body 430'. The body 430' also includes the gates 430A' and 430B' which close the chamber openings 422' and 424', respectively. The interior gate 484' is generally aligned with the dividing wall 425'. As a result, the interior gate 484' divides the interior of the body 430' into two separate chambers 436' and 437' which align with the interior chambers 421' and 423'.

As further illustrated in FIG. 4D, the interior gate 484' opens the interior valve opening 483' when the gates 430A' and 430B' are in the closed valve position. In this way, the interior valve opening 483' interconnects the interior chambers 421' and 422' while the chamber openings 422' and 424' are covered, thus allowing the interior chambers 421' and 422' to be flushed in the manner described previously. On the other hand, as illustrated in FIG. 4E, the interior gate 484' closes the interior valve opening 483' when the gates 430A' and 430B' are in the open valve position. With the interior valve opening 483' closed, the interior chambers 421' and 423' are not interconnected and each can be used for a different function, e.g. drawing blood or delivering blood during hemodialysis.

A control wire (not shown) is positioned in a control wire chamber 426' extending along the dividing wall 425'. The control wire is connected to the interior gate 484' and is operated from the proximal end to exert a longitudinal force on the body 430' in both axial directions. Because the interior gate 484' is formed with the body 430', movement of the interior gate 484' is coupled to, and coordinated with, the movement of gates 430A' and 430B'.

When the body 430' as shown in FIG. 4D is moved longitudinally toward the proximal end 412', the interior gate 484' and gates 430A' and 430B' all move together toward the proximal end 412' until they reach the positions shown in FIG. 4E. In FIG. 4D, the interior valve opening 483' is closer to the proximal end 412' than the interior gate 484', while the gates 430A' and 430B' are aligned over the chamber openings 422' and 424'. Therefore, when the body 430' moves toward the proximal end 412', the gates 430A' and 430B' become misaligned with the chamber openings 422' and 424', and at the same time, the interior gate 484' moves or slides longitudinally into alignment to cover the interior valve opening 483'.

In contrast, when the body 430' as shown in FIG. 4E is moved longitudinally toward the distal end 414', the interior gate 484' and gates 430A' and 430B' all move together toward the distal end 412' until they reach the positions shown in FIG. 4D. In FIG. 4E, the interior gate 484' is aligned with the interior valve opening 483', while the chamber openings 422' and 424' are closer to the distal end 414' than the gates 430A' and 430B'. Therefore, when the body 430' moves toward the distal end 414', the gates 430A' and 430B' move back into alignment with the chamber openings 422' and 424', and at the same time, the interior gate 484' becomes misaligned with the interior valve opening 483'.

Figure 11B:
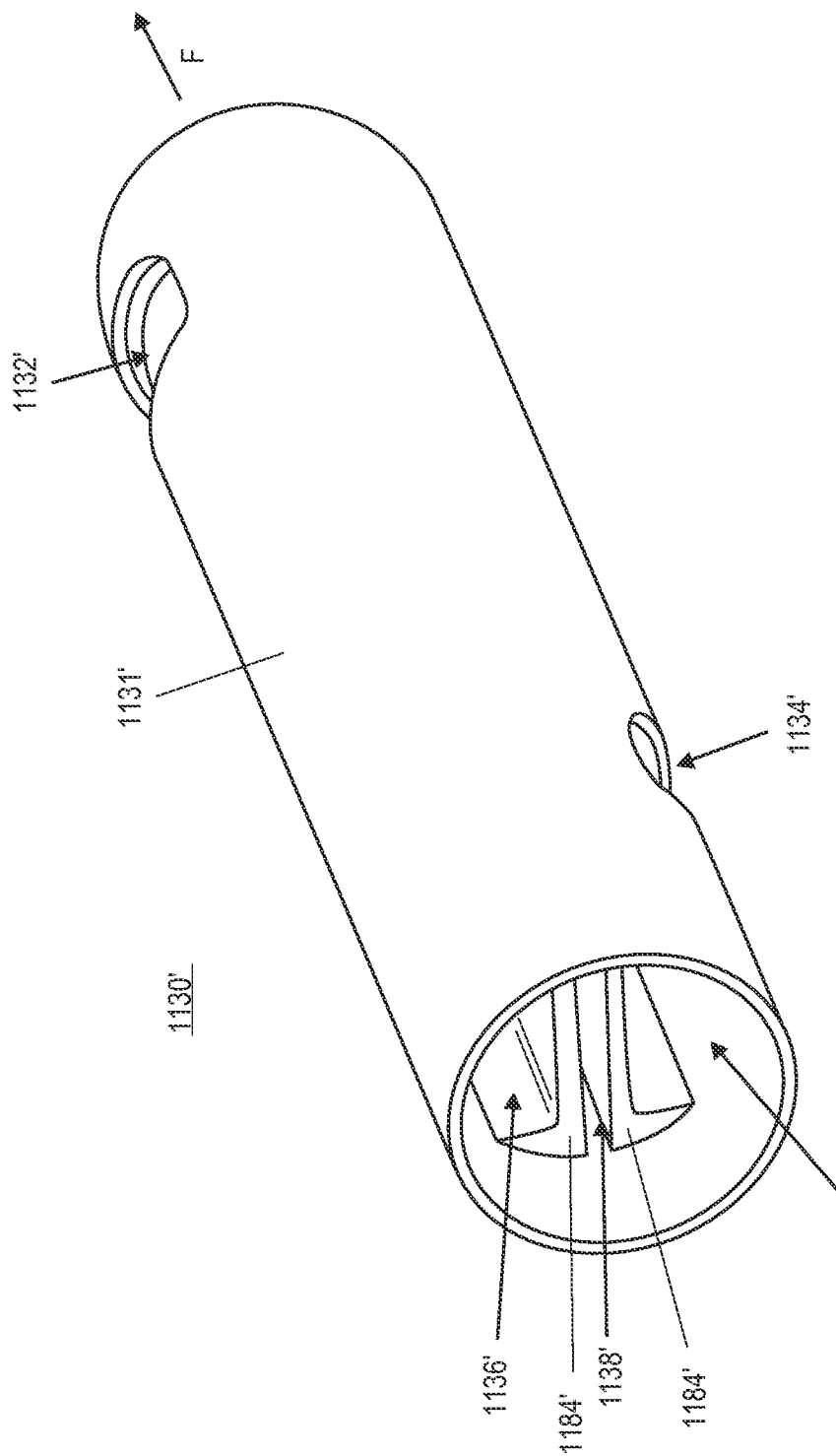
FIG. 11B illustrates an exemplary embodiment of an axially translating cap-shaped valve for use with a connecting valve connecting two interior chambers of a catheter body.

FIG. 11B illustrates a cap 1130' which is employed by an axially translating cap-shaped valve mechanism as described previously. (The cap 1130', however, is adapted to accommodate a catheter with two chamber openings that are spaced from the distal end of the catheter body by different distances.) The cap 1130' has an interior gate 1184' that controls the flow of fluid through a connecting valve that connects two interior chambers of a catheter. Like the body 430' described previously, the cap 1130' couples operation of the interior gate 1184' with the opening and closing of the chamber openings of the interior chambers in a catheter body (not shown). As the cap 1130' moves longitudinally with respect to the catheter body, the cap openings 1132' and 1134' move in and out of alignment with the chamber openings of the catheter body. When the cap openings 1132' and 1134' are aligned over the chamber openings, fluid is permitted to flow in and out of the interior chambers through the openings. With the cap openings 1132' and 1134' aligned over the chamber openings, the interior walls 1184' close the interior valve opening to substantially prevent fluidic communication between the interior chambers. When the cap 1130' is moved in the direction of arrow F shown in FIG. 11B (generally away from the proximal end of the catheter), the openings 1132' and 1134' are moved out of alignment with the chamber openings, and the wall 1131' of the cap 1130' creates barriers to the flow of fluid in and out of the interior chambers. With movement in the direction F, the interior gate 1184' opens the interior valve opening to enable fluidic communication between the interior chambers and permits the interior chambers to be flushed in the manner described above. Moving the cap 1130' opposite to the direction F blocks flow between the interior chambers again while permitting flow between the body passageway and the interior chambers.

As shown in FIG. 11B, the interior gate 1184' divides the interior of the cap 1130' into two sections 1136' and 1137' which correspond with the interior chambers of the catheter body. Moreover, a channel 1138' runs through the interior gate 1184' to allow a control wire to be extend to the tip of the cap 1130'. Operation of the control wire selectively moves the cap 1130' longitudinally.

Referring to FIGS. 13A-D, a catheter 1300, which may be employed as a central venous catheter for hemodialysis, is illustrated. The catheter 1300 extends longitudinally from a proximal end 1312 to a distal end 1314. Similar to other embodiments described herein, the catheter 1300 is generally flexible to permit positioning within a body passageway, such as a blood vessel. For example, aspects of the catheter 1300 may be formed of an elastomer with a durometer (Shore) A hardness of 30-80. In general, the catheter material is generally soft, kink-resistant, biocompatible, and compatible with alcohol, iodine, and most antiseptic solutions.

Figure 13B:
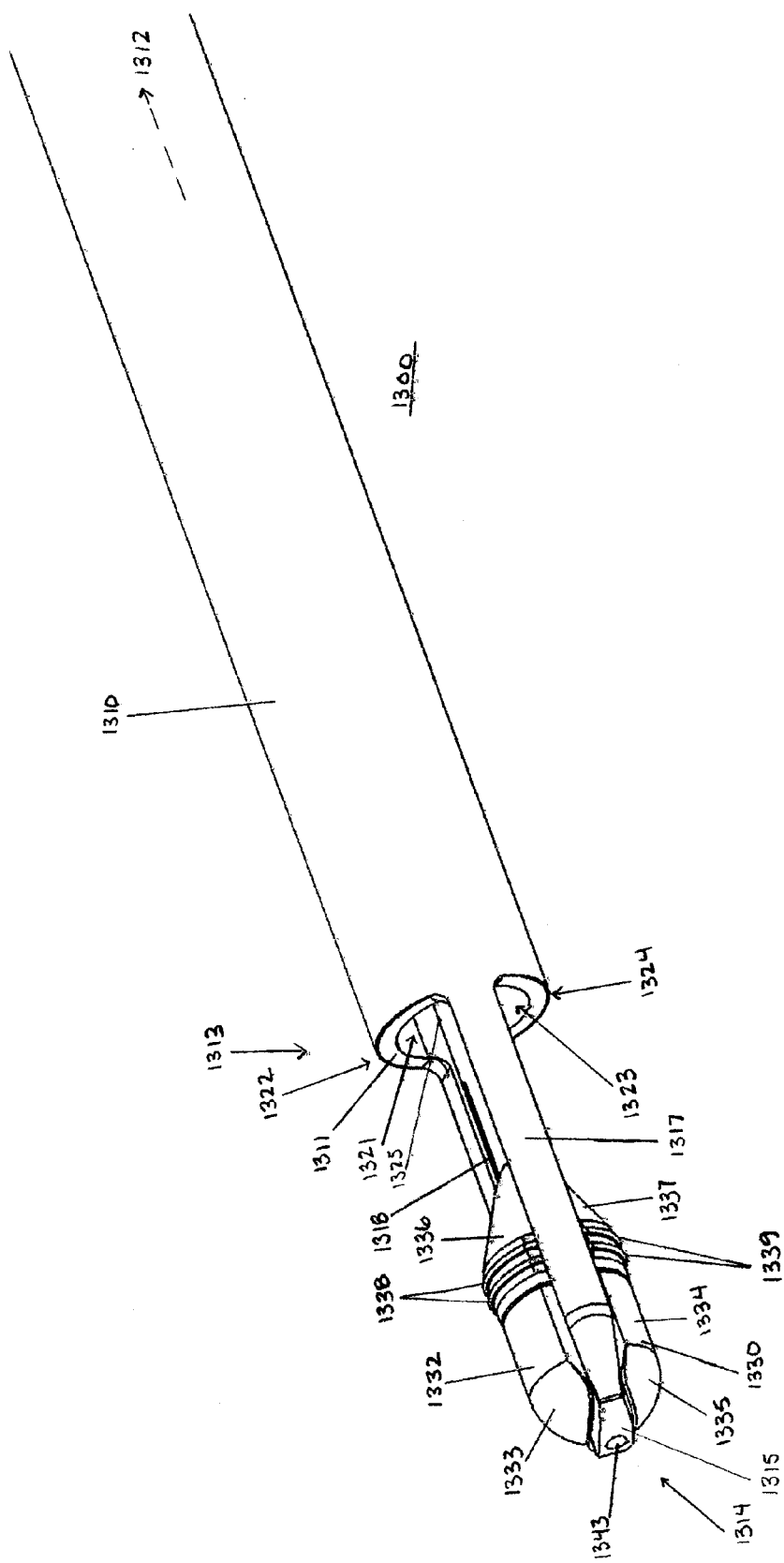
FIG. 13B illustrates the exemplary embodiment of FIG. 13A in an open valve position.
Figure 13C:
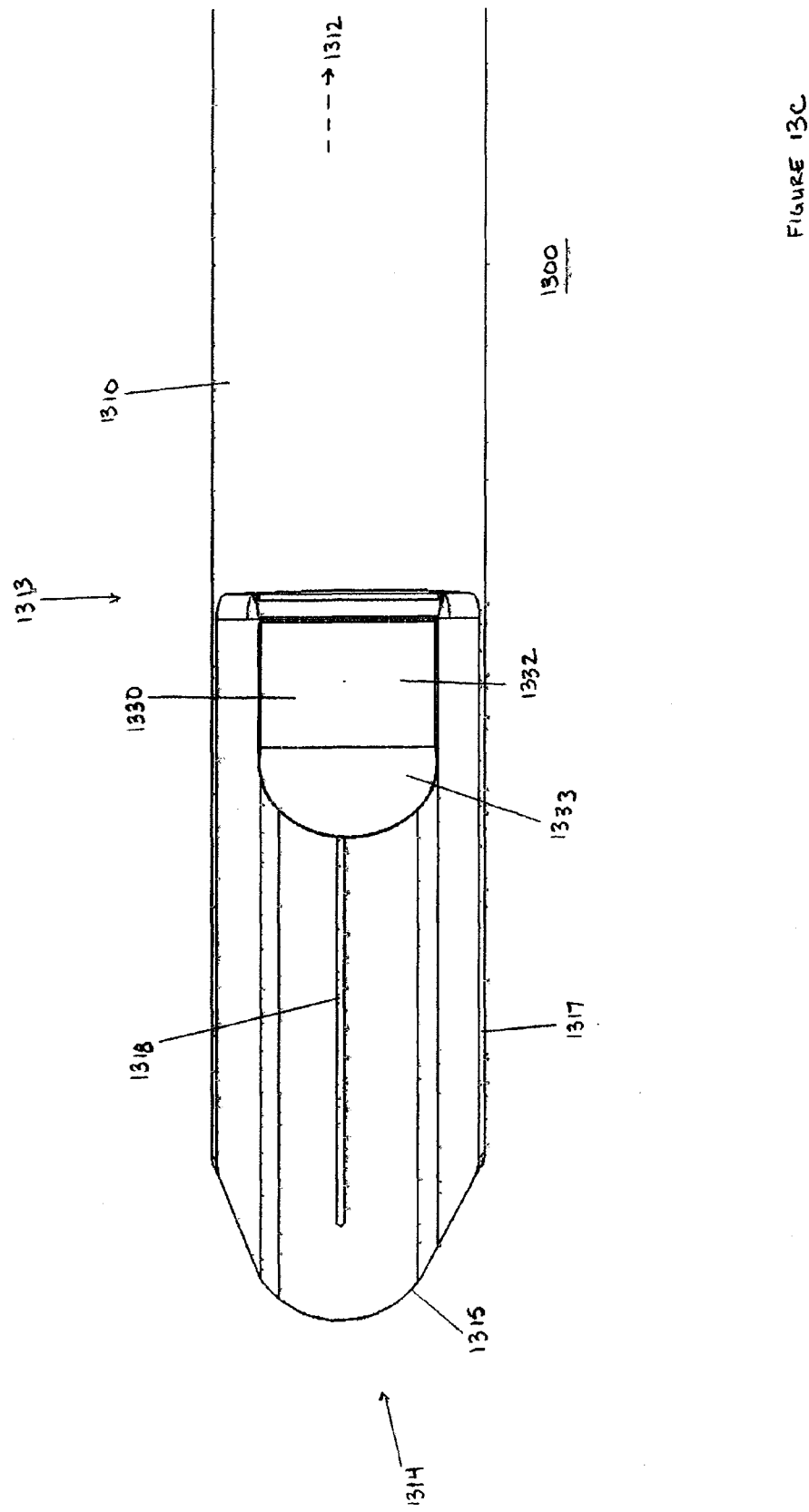
FIG. 13C illustrates the guide structure of the exemplary embodiment of FIG. 13A in the closed valve position.

The catheter 1300 may be operated from the proximal end 1312 to guide the distal end 1314 to a position in a body passageway to conduct a hemodialysis procedure. The catheter includes an elongate catheter body 1310. The elongate catheter body 1310 is defined in part by a wall 1311 which extends from the proximal end 1312 to an intermediate section 1313 disposed between the proximal end 1312 and the distal end 1314. As shown more clearly in FIG. 13B, the elongate catheter body 1310 has two interior chambers 1321 and 1323 that act to channel fluid between the proximal end 1312 and the intermediate section 1313. A dividing wall 1325 extends longitudinally within the catheter body 1310 to define the two interior chambers 1321 and 1323. The interior chambers 1321 and 1323 respectively have chamber openings, or ports, 1322 and 1324 positioned at the intermediate section 1313. The chamber openings 1322 and 1324 allow the interior chambers 1321 and 1323 to communicate with areas in the body passageway, outside the catheter body 1310. Although FIGS. 13A-B show that the chamber openings 1322 and 1324 may be positioned at substantially the same distance from the distal end 1314, other embodiments may have chamber openings positioned along the catheter body at different distances from the distal end. In other words, the chamber openings may be offset with respect to one another along the longitudinal direction.

As described previously, the use of the two separate interior chambers 1321 and 1323 within the elongate body 1310 is advantageous for applications such as hemodialysis. In such applications, a first interior chamber acts as an arterial lumen that draws blood to be filtered from the area around the intermediate section 1313 to a dialysis system connected at the proximal end 1312. Meanwhile, a second interior chamber acts as a venus lumen that directs filtered blood from the dialysis system to the area around the intermediate section 1313.

As illustrated in FIGS. 13A-B, the catheter 1300 also includes a guide structure 1317 that extends from the intermediate section 1313 to the distal end 1314. Like other aspects of the catheter 1300, the guide structure 1317 may be formed from a flexible material, such as an elastomer, to facilitate deployment of the catheter 1300 within the body passageway. On one end, the guide structure 1317 extends from the catheter body 1310. Meanwhile, on the other end, the guide structure 1317 may include a rounded end structure 1315 that forms the distal end 1314 of the catheter 1300. The round shape of the end structure 1315 minimizes trauma when the catheter is deployed within the body passageway.

As shown further in FIGS. 13A-B, the chamber openings 1322 and 1324 are disposed on opposite sides of the guide structure 1317. In particular, FIG. 13B shows that the guide structure 1317 may be an extension of the dividing wall 1325 in the elongate body 1310. In some embodiments, the guide structure 1317 may be integrally formed with the dividing wall 1325, while in other embodiments, the guide structure 1317 may be an element that is separately attached to the dividing wall 1325.

The guide structure 1317 separates fluid flowing into or out of the respective interior chambers 1321 and 1323. As a result, when employed for hemodialysis, the configuration of the catheter 1300 provides an efficient technique for drawing blood from one section of the blood vessel and delivering filtered blood to a separate section of the blood vessel. In other words, the amount of mixing, or recirculation, between the outflow of filtered blood and inflow non-filtered blood is minimized. It has been determined, for example, that when deploying the catheter 1300 in the superior vena cava proximate to the right atrium for hemodialysis, a longitudinal length of approximately ½-inch for the guide structure 1317 is sufficient to substantially prevent mixing of filtered and non-filtered blood, where the flow within the superior vena cava is approximately 2000 ml/min and the flow rate within the interior chambers 1321 and 1323 is approximately 450 ml/min.

As further illustrated in FIGS. 13A-D, a valve mechanism 1330 may be employed to control the flow of fluid through the chamber openings 1322 and 1324. In particular, the valve mechanism 1330 includes two barrier elements 1332 and 1334 corresponding to the chamber openings 1322 and 1324, respectively. The barrier elements 1332 and 1334 act as barriers to the flow of fluid into, or from, the respective chamber openings 1322 and 1324 when the valve mechanism 1330 is positioned in a closed valve position, as shown in FIG. 13A. However, when the valve mechanism 1330 is in an open valve position as shown in FIG. 13B, the barrier elements 1332 and 1334 no longer block the flow of fluid through the respective chamber openings 1322 and 1324, and fluid flows between the interior chambers 1321 and 1323 and areas in the body passageway outside the catheter 1300. In addition, operation of the valve mechanism 1330 may also be employed to achieve disruption and removal of any thrombus or fibrin which has accumulated over the catheter 1300 at or near the intermediate section 1313.

As shown in FIGS. 13A-B, the valve mechanism 1330 moves longitudinally along the guide structure 1317 when it moves between the open valve position and the closed valve position. Because the chamber openings 1322 and 1324 are disposed on opposite sides of the guide structure 1317, the barrier elements 1332 and 1334 are also disposed on opposite sides of the guide structure 1317. Each barrier element 1332 and 1334 includes a substantially planar surface that moves correspondingly along a substantially planar surface of the guide structure 1317.

As illustrated in FIG. 13D, partially domed structures 1333 and 1335 define one end of the barrier elements 1332 and 1334, respectively. The partially domed structures 1333 and 1335 are shaped to minimize trauma particularly during positioning of the catheter 1300 within the body passageway or during movement of the valve mechanism 1330 between open and closed valve positions. However, it is understood that different contoured structures may be employed for the barrier elements 1332 and 1334 to minimize trauma.

Meanwhile, tapered structures 1336 and 1337 define the other end of the barrier elements 1332 and 1334, respectively. When the valve mechanism 1330 is in the closed valve position as shown in FIG. 13A, the tapered structures 1336 and 1337 are inserted into the interior chambers 1321 and 1323 through the chamber openings 1322 and 1324, respectively. The tapered structures 1336 and 1337 act as barriers to the flow of fluid into, or from, the respective chamber openings 1322 and 1324. The shape of the tapered structures 1336 and 1337 facilitates the movement of the valve mechanism 1330 into the closed valve position, especially against the pressure of any outflow of fluid through the chamber opening 1322 or 1324.

The tapered structures 1336 and 1337 may be formed from a soft elastomer, while the remaining portions of the barrier elements 1332 and 1334, including the partially domed structures 1333 and 1335, may be formed from a hard plastic. The soft elastomer may be silicone, polyurethane, or the like, while the hard plastic may be PEEK, nylon, polyester, Teflon®, or the like. The soft elastomer of the tapered structures 1336 and 1337 are securely attached to the hard plastic, so that the tapered structures 1336 and 1337 do not become detached from the rest of the barrier elements 1332 and 1334 within the body passageway during operation of the valve mechanism 1330. In particular, the technique for attaching the tapered structures 1336 and 1337 must be sufficient to withstand the tension that the barrier elements 1332 and 1334 may experience when the tapered structures 1336 and 1337 are moved from the closed valve position to the open valve position against the seal formed with the interior chambers 1321 and 1323. Techniques for attaching the tapered structures 1336 and 1337 may include, but are not limited to, any combination of adhesive bonding, press fit, snap-fit, other types of mechanical interlocking, use of fasteners, or the like.

The soft elastomer may facilitate positioning of the tapered structures 1336 and 1337 within corresponding chamber openings 1322 and 1324. In addition, the soft elastomer may permit a snug fit between the tapered structures 1336 and 1337 and the corresponding inner walls of the interior chambers 1321 and 1323. To minimize the likelihood that gaps will exist between the tapered structures 1336 and 1337 and the inner walls of the chamber openings 1322 and 1324, the tapered structures 1336 and 1337 may include one or more sealing structures 1338 and 1339, respectively. In particular, the sealing structures 1338 and 1339 extend transversely outward from the periphery of the tapered structures 1336 and 1337 to provide sealing engagement with the inner walls of the interior chambers 1321 and 1323. The sealing structures 1338 and 1339 may be integrally formed with the tapered structures 1336 and 1337 from the same soft elastomer. In other embodiments, however, the sealing structures 1338 and 1339 may be formed from different materials and/or attached as separate components, for example with an adhesive or a mechanical fit, to the tapered structures 1336 and 1337.

It is understood that the materials used to form the catheter 1300 are not limited to the configurations described previously. For example, the partially domed structures 1333 and 1335 may also be formed from an elastomer instead of a hard plastic. As such, the partially domed structures 1333 and 1335 in this alternative embodiment may be integrally molded with the tapered structures 1336 and 1337.

FIG. 13D also shows a connecting structure 1341 that extends between the barrier elements 1332 and 1334. The connecting structure 1341 may be a thin metallic strip, for example. The connecting structure 1341 couples movement of the barrier elements 1332 and 1334. Because each barrier element 1332 and 1334 appears to form one-half of a plug, coupled movement of the barrier elements 1332 and 1334 appears as a single longitudinally translating plug. The connecting structure 1341 is securely attached to each of the barrier elements 1332 and 1334, so that the barrier elements 1332 do not become detached within the body passageway during operation of the valve mechanism 1330. Techniques for attaching the barrier elements 1332 and 1334 may include, but are not limited to, any combination of adhesive bonding, press fit, snap-fit, other types of mechanical interlocking, use of fasteners, or the like.

As described previously, the barrier elements 1332 and 1334 are disposed on opposite sides of the guide structure 1317. As such, the connecting structure 1341 passes through the guide structure 1317 to maintain the coupling between the barrier elements 1332 and 1334. As shown more clearly in FIG. 13C, the guide structure 1317 includes an opening 1318 to allow passage of the connecting structure 1341. In particular, if the connecting structure 1341 is a metallic strip, the opening 1318 may be a thin slit dimensioned to correspond with the thickness of the metallic strip. Operation of the valve mechanism 1330 causes the barrier elements 1332 and 1334 to move along the guide structure 1317. Thus, the opening 1318 extends along the guide structure 1317 to permit the connecting structure 1341 to move correspondingly along the guide structure 1317.

The valve mechanism 1330 may be installed on the guide structure 1317 by assembling the barrier elements 1332 and 1334 together via the connecting structure 1341 while the guide structure 1317 is disposed between them and the connecting structure 1341 is disposed in the opening 1318. Alternatively, the barrier elements 1332 and 1334 may be assembled together before the valve mechanism 1330 is installed on the guide structure 1317. For example, the barrier elements 1332 and 1334 may be molded over the connecting structure 1341, and the assembled valve mechanism 1330 may subsequently be passed through the opening 1318. As the guide structure 1317 may be formed from a flexible material, such as an elastomer, the opening 1318 may be temporarily deformed and enlarged to allow one of the barrier elements 1332 and 1334 to pass through the opening 1318 so that the barrier elements 1332 and 1334 are positioned on opposing sides of the guide structure 1317.

As further shown in FIG. 13B, when the valve mechanism 1330 is moved along the guide structure 1317 to a fully open valve position, the partially domed structures 1333 and 1335 of the barrier elements 1332 and 1334, respectively, do not extend beyond the end structure 1315 of the guide structure 1317. As described previously, the end structure 1315 of the guide structure 1317 defines the distal end 1314 of the catheter 1300. Thus, once the catheter 1300 is positioned within a body passageway, the guide structure 1317 determines the farthest the catheter 1300 must extend into the body passageway, and operation of the valve mechanism 1330 does not require the catheter 1300 to extend any further into the body passageway.

As illustrated in FIG. 13D, a control wire 1340 is also attached to the connecting structure 1341. Movement of the control wire 1340 causes corresponding movement of the connecting structure 1341 and the two barrier elements 1332 and 1334. The control wire 1340 may be attached to the connecting structure 1341 according to techniques, which include, but are not limited to, any combination of adhesive bonding, press fit, snap-fit, other types of mechanical interlocking, use of fasteners, or the like. In addition, spading of the end of the control wire 1340 may be employed to create a flatter surface on the control wire 1340 to facilitate attachment of the control wire 1340 to the connecting structure. Moreover, the control wire 1340 may pivot about the connecting structure 1341 to facilitate operation, especially if the catheter 1300 near the intermediate section 1313 attains a curved shape within the body passageway. As described previously, the longitudinal length of the guide structure 1317 may be approximately ½-inch. In an example embodiment, the valve mechanism 1330 may be approximately ¼-inch in length longitudinally. Accordingly, when the valve mechanism 1330 is in the completely open valve position shown in FIG. 13B, the valve mechanism 1330 is spaced from the chamber openings 1322 and 1324 by approximately ¼-inch.

The control wire 1340 extends through the elongate body 1310 from the proximal end 1312, where the control wire 1340 may be manipulated by an operator. Movement of the control wire 1340 at the proximal end 1312 translates through the elongate body 1310 to the connecting structure 1341 within the guide structure 1317. In particular, similar to other embodiments described herein, a channel for the control wire 1340 may be disposed within the interior dividing wall 1325, which divides the elongate body 1310 into the interior chambers 1321 and 1323. As shown in FIG. 13B, the guide structure 1317 is integral with and extends from the dividing wall 1325, so the channel for the control wire 1340 also extends through the guide structure 1317 until it coincides with the opening 1318 where the control wire 1340 is attached to the connecting structure 1341.

Similar to other embodiments described herein, a guide wire channel 1343 extends through the catheter 1300 from the proximal end 1312 and the distal end 1314. FIGS. 13A-B show the opening of the guide wire channel 1343 at the distal end 1314. As such, in order to facilitate catheter positioning, the implanting physician may extend a guide wire to a location in a body passageway. The guide wire is then positioned within the guide wire channel 1343, and the catheter body 1310 is guided along the guide wire to the location in the body passageway. Once the catheter 1300 is positioned in the body passageway, the guide wire can be extracted. Upon guide wire removal, a permanent plug may be inserted into the proximal end of the catheter 1300 to close the guide wire channel 1343 and prevent air embolism and/or blood loss, for example. To further facilitate proper positioning of the catheter body 1300 within the body passageway, the guide wire may include, near the distal end of the guide wire, a centering mechanism, such as a plurality of elongate legs defining an expanding centering basket. The guide wire channel 1343 may extend separately along the control wire channel or may coincide with the control wire channel. In some embodiments, the guide wire channel 1343 may extend through the control wire 1340, which in turn passes though the control wire channel.

Figure 14A:
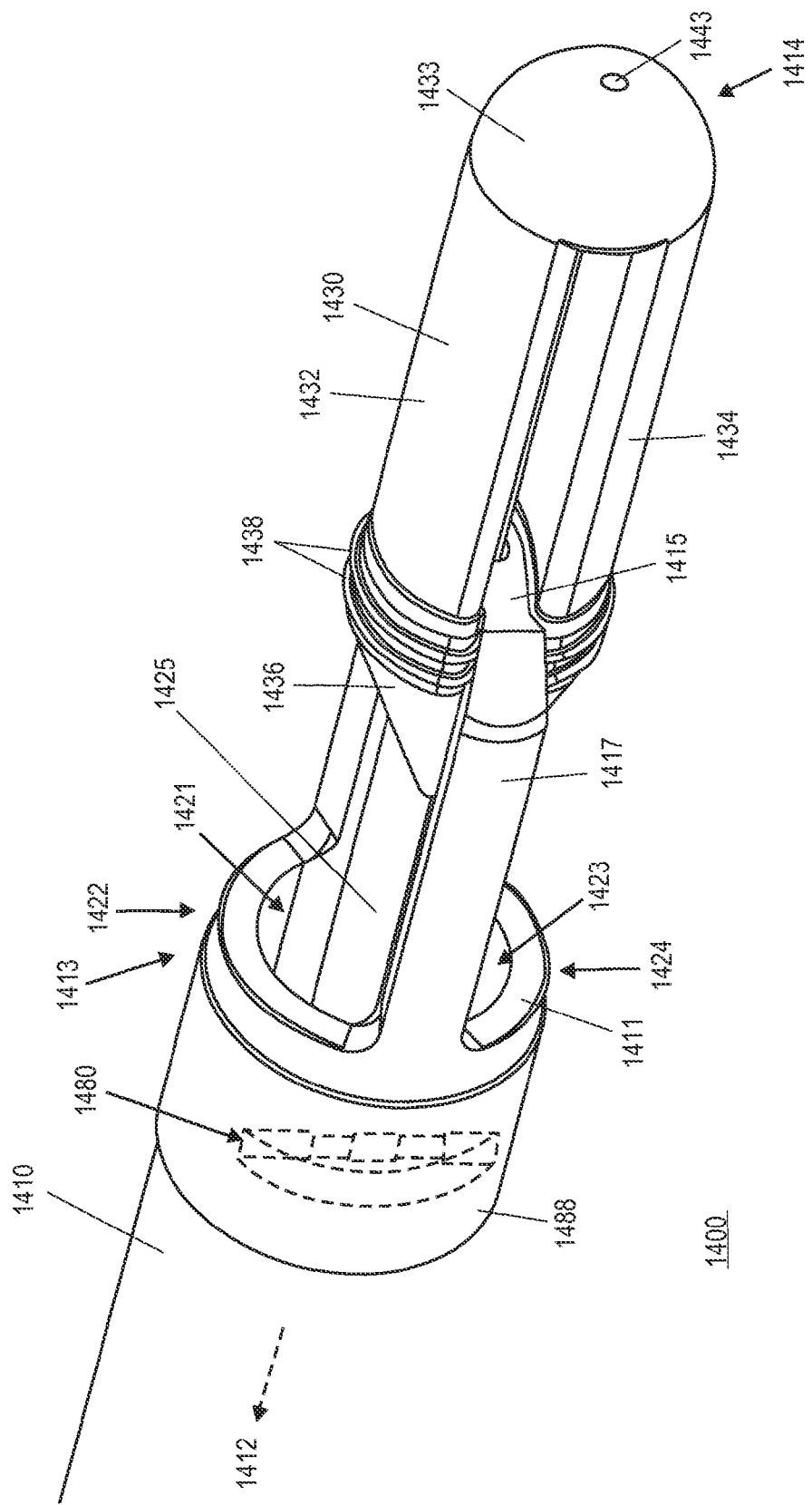
FIG. 14A illustrates an exemplary embodiment in an open valve position.
Figure 14B:
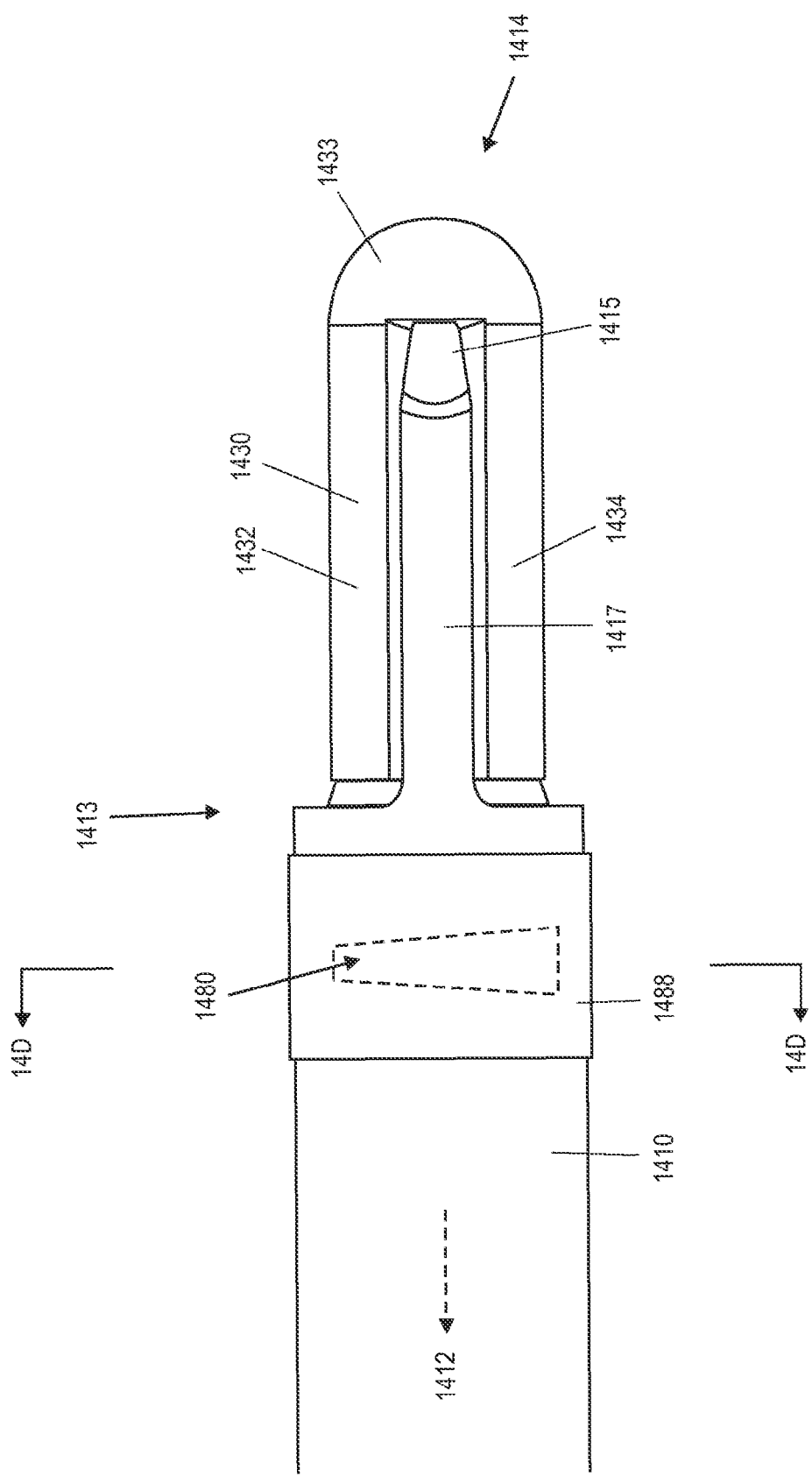
FIG. 14B illustrates the exemplary embodiment of FIG. 13A in a closed valve position.
Figure 14C:
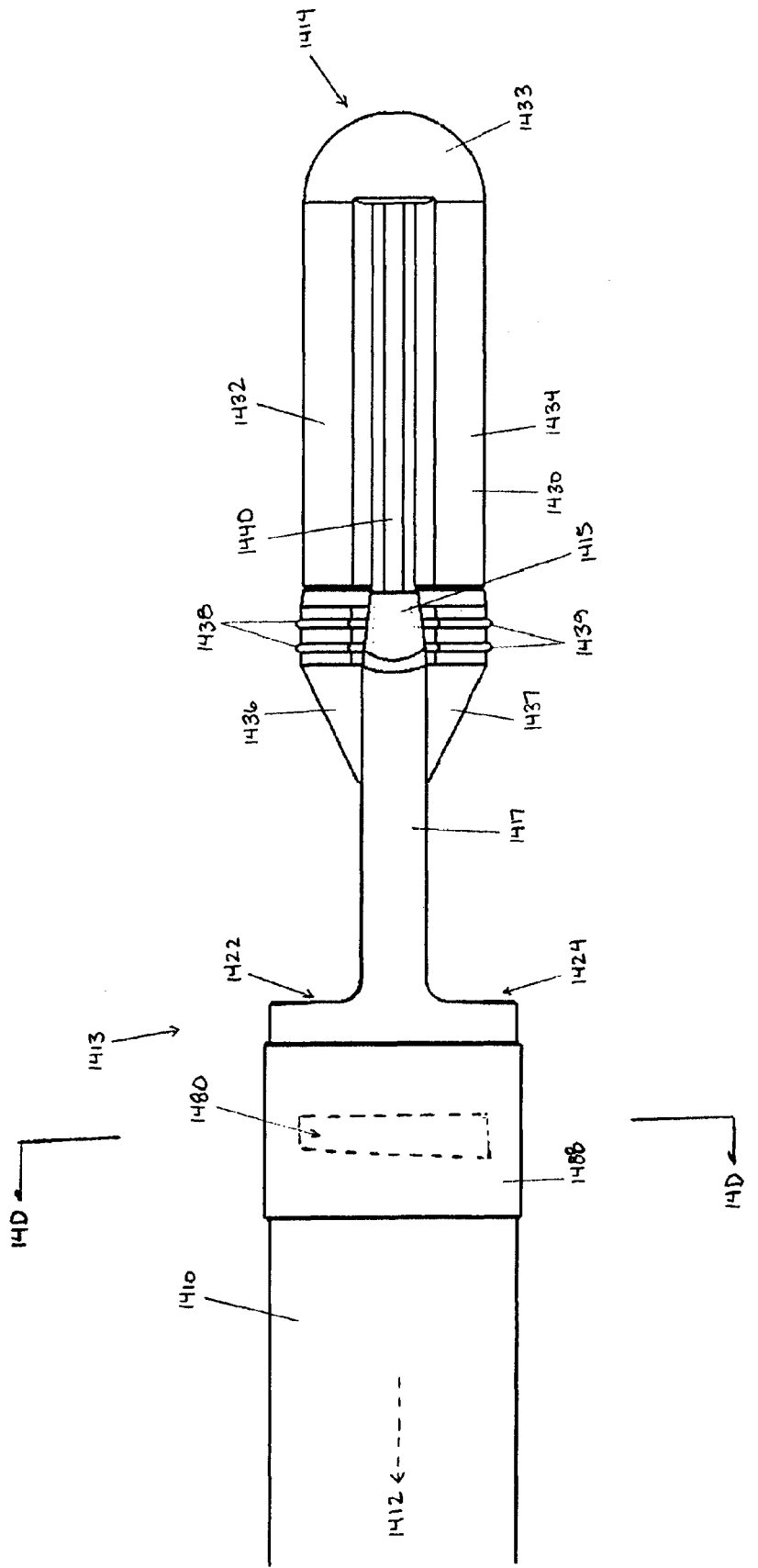
FIG. 14C illustrates another view of the exemplary embodiment of FIG. 14A.

Referring to FIGS. 14A-C, another catheter 1400, which may also be employed as a central venous catheter for hemodialysis, is illustrated. The catheter 1400 extends longitudinally from a proximal end 1412 to a distal end 1414. The catheter 1400 may be operated from the proximal end 1412 to guide the distal end 1414 to a position in a body passageway to conduct a hemodialysis procedure.

Similar to other embodiments described herein, the catheter 1400 is generally flexible to permit positioning within a body passageway, such as a blood vessel. In general, the catheter material is generally soft, kink-resistant, biocompatible, and compatible with alcohol, iodine, and most antiseptic solutions.

The catheter includes an elongate catheter body 1410. The elongate catheter body 1410 is defined in part by a wall 1411 which extends from a proximal end 1412 to an intermediate section 1413 disposed between the proximal end 1412 and the distal end 1414. As shown more clearly in FIG. 14A, the elongate catheter body 1410 has two interior chambers 1421 and 1423 that act to channel fluid between the proximal end 1412 and the intermediate section 1413. A dividing wall 1425 extends longitudinally within the catheter body 1410 to define the two interior chambers 1421 and 1423. The interior chambers 1421 and 1423 respectively have chamber openings, or ports, 1422 and 1424 positioned at the intermediate section 1413. The chamber openings 1422 and 1424 allow the interior chambers 1421 and 1423 to communicate with areas in the body passageway, outside the catheter body 1410. Although FIG. 14A shows that the chamber openings 1422 and 1424 may be positioned at substantially the same distance from the distal end 1414, other embodiments may have chamber openings positioned along the catheter body at different distances from the distal end. In other words, the chamber openings may be offset with respect to one another along the longitudinal direction.

As described previously, the use of the two separate interior chambers 1421 and 1423 within the elongate body 1410 is advantageous for applications such as hemodialysis. In such applications, a first interior chamber acts as an arterial lumen that draws blood to be filtered from the area around the intermediate section 1413 to a dialysis system connected at the proximal end 1412. Meanwhile, a second interior chamber acts as a venus lumen that directs filtered blood from the dialysis system to the area around the intermediate section 1413.

As illustrated in FIGS. 14A-B, the catheter 1400 also includes a guide structure 1417 that extends from the intermediate section 1413 to the distal end 1414. Like other aspects of the catheter 1400, the guide structure may be formed from a flexible material, such as an elastomer, to facilitate deployment of the catheter 1400 within the body passageway. On one end, the guide structure 1417 extends from the catheter body 1410. Meanwhile, on the other end, the guide structure 1417 includes an end structure 1415. As shown further in FIGS. 14A-C, the chamber openings 1422 and 1424 are disposed on opposite sides of the guide structure 1417. In particular, FIG. 14A shows that the guide structure 1417 may be formed as an extension of the dividing wall 1425 in the elongate body 1410. In some embodiments, the guide structure 1417 may be integrally formed with the dividing wall 1425, while in other embodiments, the guide structure 1417 may be an element that is separately attached to the dividing wall 1425.

As further illustrated in FIGS. 14A-C, a U-shaped valve mechanism 1430 may be employed to control the flow of fluid through the chamber openings 1422 and 1424. In particular, the valve mechanism 1430 includes two barrier elements 1432 and 1434 corresponding to the chamber openings 1422 and 1424, respectively. The barrier elements 1432 and 1434 act as barriers to the flow of fluid into, or from, the respective chamber openings 1422 and 1424 when the valve mechanism 1430 is positioned in a closed valve position, as shown in FIG. 14B. However, when the valve mechanism 1430 is in an open valve position as shown in FIG. 14A, the barrier elements 1432 and 1434 no longer block the flow of fluid through the respective chamber openings 1422 and 1424, and fluid flows between the interior chambers 1421 and 1423 and areas in the body passageway outside the catheter 1400. In addition, operation of the valve mechanism 1430 may also be employed to achieve disruption and removal of any thrombus or fibrin which has accumulated over the catheter 1400 at or near the intermediate section 1413.

As shown in FIGS. 14A-C, the valve mechanism 1430 moves longitudinally along the guide structure 1417 when it moves between the open valve position and the closed valve position. Because the chamber openings 1422 and 1424 are disposed on opposite sides of the guide structure 1417, the barrier elements 1432 and 1434 are also disposed on opposite sides of the guide structure 1417. Each barrier element 1432 and 1434 includes a substantially planar surface that moves correspondingly along a substantially planar surface of the guide structure 1417.

As illustrated in FIGS. 14A and C, tapered structures 1436 and 1437 define one end of the barrier elements 1432 and 1434, respectively. When the valve mechanism 1430 is in the closed valve position as shown in FIG. 14B, the tapered structures 1436 and 1437 are inserted into the interior chambers 1421 and 1423 through the chamber openings 1422 and 1424, respectively. The tapered structures 1436 and 1437 act as barriers to the flow of fluid into, or from, the respective chamber openings 1422 and 1424. The shape of the tapered structures 1436 and 1437 facilitates the movement of the valve mechanism 1430 into the closed valve position, especially against any pressure from the outflow of fluid through the chamber opening 1422 or 1424.

The tapered structures 1436 and 1437 may be formed from a soft elastomer. The soft elastomer may facilitate positioning of the tapered structures 1436 and 1437 within corresponding chamber openings 1422 and 1424. In addition, the soft elastomer may permit a snug fit between the tapered structures 1436 and 1437 and the corresponding inner walls of the interior chambers 1421 and 1423. To minimize the likelihood that gaps will exist between the tapered structures 1436 and 1437 and the inner walls of the chamber openings 1422 and 1424, the tapered structures 1436 and 1437 may include one or more sealing structures 1438 and 1439, respectively. In particular, the sealing structures 1438 and 1439 extend transversely outward from the periphery of the tapered structures 1436 and 1437 to provide sealing engagement with the inner walls of the interior chambers 1421 and 1423. The sealing structures 1438 and 1439 may be integrally formed with the tapered structures 1436 and 1437 from the same soft elastomer. In other embodiments, however, the sealing structures 1438 and 1439 may be formed from different materials and/or attached as separate components, for example with an adhesive or a mechanical fit, to the tapered structures 1436 and 1437.

As shown in FIGS. 14A-C, the barrier elements 1432 and 1434 extend to a domed structure 1433 that defines the other end of the valve mechanism 1430. The domed structure 1433 couples movement of the barrier elements 1432 and 1434. Because each barrier element 1432 and 1434 appears to form one-half of a plug, coupled movement of the barrier elements 1432 and 1434 appears as a single longitudinally translating plug.

The domed structure 1433 is positioned over the end structure 1415 of the guide structure 1417, so that the domed structure 1433 combines with the barrier elements 1432 and 1434 to give the valve mechanism 1430 a U-shape disposed over the guide structure 1417. In addition, the substantially semi-spherical domed structure 1433 minimizes trauma particularly during positioning of the catheter 1400 within the body passageway or during movement of the valve mechanism 1430 between open and closed valve positions. It is understood, however, the end of the valve structure 1430 is not limited to a semi-spherical shape, and any contoured shape may be employed to minimize trauma.

As FIGS. 14A-C illustrates, the domed structure 1433 defines the distal end 1414 of the catheter 1400. The domed structure 1433 moves relative to the guide structure 1417 when the valve mechanism 1430 is moved between the closed and open valve positions. As a result, unlike the catheter 1300 described previously, the distal end 1414 of the catheter 1400 moves further into the body passageway when the valve mechanism 1430 is moved along the guide structure 1417 to a fully open valve position.

While the tapered structures 1436 and 1437 may be formed from a soft elastomer, the remaining portions of the valve mechanism 1430, including the domed structure 1433, may be formed from a hard plastic. The soft elastomer may be silicone, polyurethane, or the like, while the hard plastic may be PEEK, nylon, polyester, Teflon®, or the like. The soft elastomer of the tapered structures 1436 and 1437 are securely attached to the hard plastic, so that the tapered structures 1436 and 1437 do not become detached from the rest of the barrier elements 1432 and 1434 within the body passageway during operation of the valve mechanism 1430. In particular, the technique for attaching the tapered structures 1436 and 1437 must be sufficient to withstand the tension that the barrier elements 1432 and 1434 may experience when the tapered structures 1436 and 1437 are moved from the closed valve position to the open valve position against the seal formed with the interior chambers 1421 and 1423. In addition, the domed structure 1433 may be formed integrally with the hard plastic portions of the barrier elements 1432 and 1434, or may be a separate element formed of the same or different material and securely attached to each of the barrier elements 1432 and 1434. In general, the valve mechanism 1430 is formed and assembled in a manner that prevents any part of the barrier elements 1432 and 1434 from becoming detached within the body passageway during operation of the valve mechanism 1430. Techniques for assembling the valve mechanism 1430 may include, but are not limited to, any combination of adhesive bonding, press fit, snap-fit, other types of mechanical interlocking, use of fasteners, or the like.

As illustrated in FIG. 14C, a control wire 1440 is attached to the domed structure 1433. Movement of the control wire 1440 causes corresponding movement of the domed structure 1433 and the two barrier elements 1432 and 1434. The control wire 1440 may be attached to the domed structure 1433 according to techniques, which include, but are not limited to, any combination of adhesive bonding, press fit, snap-fit, other types of mechanical interlocking, use of fasteners, or the like.

It is understood that the materials used to form the catheter 1400 are not limited to the configurations described previously. For example, rather than employing hard plastic elements, the valve mechanism 1430 may be formed substantially from an elastomer. As such, the barrier elements 1432 and 1434 and the domed structure 1433 may be integrally molded from the same elastomer. In one embodiment, the barrier elements 1432 and 1434 and the domed structure 1433 may be overmolded as an integral element over the control wire 1440.

The valve mechanism 1430 may be installed on the guide structure 1417 by assembling the barrier elements 1432 and 1434 together with the domed structure 1433 while the guide structure 1417 is disposed between them. Alternatively, the barrier elements 1432 and 1434 may be assembled together before the valve mechanism 1430 is installed on the guide structure 1417.

The control wire 1440 extends through the elongate body 1410 from the proximal end 1412, where the control wire 1440 may be manipulated by an operator. Movement of the control wire 1440 at the proximal end 1412 translates through the elongate body 1410 to the domed structure 1433. In particular, similar to other embodiments described herein, a channel for the control wire 1440 may be disposed within the interior dividing wall 1425, which divides the elongate body 1410 into the interior chambers 1421 and 1423. As shown in FIG. 14A, the guide structure 1417 is integral with and extends from the dividing wall 1425, so the channel for the control wire 1440 also extends through the guide structure 1417 until it reaches the domed structure 1433 on the other side of end structure 1415 of the guide structure 1417. As the valve mechanism 1430 moves from the closed valve position to the open valve position, the control wire 1440 extends correspondingly beyond the end structure 1415 as shown in FIG. 14C.

Similar to other embodiments described herein, a guide wire channel 1443 extends through the catheter 1400 from the proximal end 1412 and the distal end 1414. FIG. 14A shows the opening of the guide wire channel 1443 at the distal end 1414. As such, in order to facilitate catheter positioning, the implanting physician may extend a guide wire to a location in a body passageway. The guide wire is then positioned within the guide wire channel 1443, and the catheter body 1410 is guided along the guide wire to the location in the body passageway. Once the catheter 1400 is positioned in the body passageway, the guide wire can be extracted. Upon guide wire removal, a permanent plug may be inserted into the proximal end of the catheter 1400 to close the guide wire channel 1443 and prevent air embolism and/or blood loss, for example. To further facilitate proper positioning of the catheter body 1400 within the body passageway, the guide wire may include, near the distal end of the guide wire, a centering mechanism, such as a plurality of elongate legs defining an expanding centering basket. The guide wire channel 1443 may extend separately along the control wire channel or may coincide with the control wire channel. In some embodiments, the guide wire channel 1443 may extend through the control wire 1440, which in turn passes though the control wire channel.

The combination of the guide structure 1417 and the valve mechanism 1430 extends from the chamber openings 1422 and 1424 and separates fluid flowing into or out of the respective interior chambers 1421 and 1423. As a result, when employed for hemodialysis, the configuration of the catheter 1400 provides an efficient technique for drawing blood from one section of the blood vessel and delivering filtered blood to a separate section of the blood vessel. In other words, the amount of mixing, or recirculation, between the outflow of filtered blood and inflow non-filtered blood is minimized. It has been determined, for example, that when deploying the catheter 1400 in the superior vena cava proximate to the right atrium for hemodialysis, a longitudinal length of approximately ¼-inch for the guide structure 1417 combined with a longitudinal length of approximately ⅜-inch for the valve mechanism 1430 is sufficient to substantially prevent mixing of filtered and non-filtered blood, where the flow within the superior vena cava is approximately 2000 ml/min and the flow rate within the interior chambers 1421 and 1423 is approximately 450 ml/min. With this particular configuration, when the valve mechanism 1430 is moved completely to the open valve configuration as shown in FIG. 14A, the combination of the guide structure 1417 and the valve mechanism 1430 extends to approximately ½-inch from the chamber openings 1422 and 1424.

As described previously, it may be advantageous to fill and/or flush the interior chambers of a catheter. Antibiotic, antimicrobial, anticoagulant, lytics, or saline solutions, or the like, may be introduced into the interior chambers 1421 and 1423. In addition, old, stagnant lock solution that remains in the catheter 1400 between hemodialysis treatments may be removed by flushing. Accordingly, the catheter 1400 as shown in FIGS. 14A-D employs a connecting channel, or bridge, 1480 that connects the interior chambers 1421 and 1423 at or near the intermediate section 1413. The connecting channel 1480 allows flushing and/or filling of the interior chambers 1421 and 1423 when the valve mechanism 1430 is in the closed valve position. When the valve mechanism 1430 is in the closed valve position, fluid can be introduced from a source at the proximal end 1412 into one of the interior chambers 1421 and 1423 where it flows toward the distal end 1414 to the connecting channel 1480. The connecting channel 1480 then allows the fluid to flow to the other interior chamber and back to the proximal end 1412. In a flushing operation, the fluid may exit the catheter 1400 at the proximal end 1412. Without the connecting channel 1480, removing any fluid in the interior chambers 1421 and 1423 would generally require the valve mechanism 1430 to be moved into the open valve position to prevent a vacuum from forming within the interior chambers 1421 and 1423 as the fluid is extracted. When the valve mechanism 1430 is in the open valve position, there is a risk that any chemicals introduced into the chamber openings 1422 and 1424 may escape into the body passageway. However, because the connecting channel 1480 permits the valve mechanism 1430 to remain in the closed valve position, the catheter 1400 minimizes systemic spillage of chemicals introduced into the interior chambers 1421 and 1423. In other words, the catheter 1400 can be safely and effectively filled or flushed without introducing any unwanted fluids into the body passageway. The closed valve mechanism 1430 also prevents fluid from the body passageway, such as blood, from entering the interior chambers 1421 and 1423. Furthermore, because the valve mechanism 1430 remains in the closed position during filling and/or flushing operations, the risk of air emboli entering the body passageway is minimized.

Figure 14D:
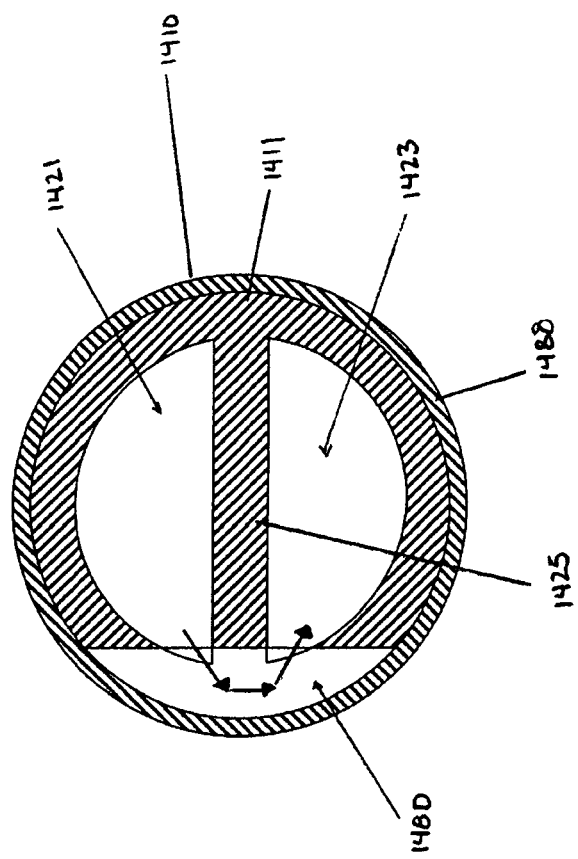
FIG. 14D illustrates a cross-sectional view of the connecting channel extending between the interior chambers of the exemplary embodiment of FIG. 14A.

Referring to FIGS. 14A-D, the connecting channel 1480 may be defined by cutting a slit-shaped opening, or notch, through the catheter wall 1411. In particular, FIG. 14D illustrates a cross-sectional view of the connecting channel 1480. The connecting channel 1480 extends along the periphery of the catheter body 1410 and is substantially perpendicular to the dividing wall 1425. The connecting channel 1480 extends transversely from the outer surface of the wall 1411 into a part of the dividing wall 1425. By cutting into a part of the dividing wall 1425, the connecting channel 1480 provides fluid communication between the interior chambers 1421 and 1423, as illustrated for example by the flow arrows in the cross-sectional view of FIG. 14D. The fluid communication occurs along the inner surface of the wall 1411. In some embodiments, more than one connecting channel may be employed by cutting into more than one section of the dividing wall 1425. In one embodiment, cuts are made into opposing sides of the wall 1411 to provide fluid communication on two sides of the dividing wall 1425.

The connecting channel 1480, which may be employed in any catheter, provides manufacturing advantages, because it is formed by efficiently cutting through the wall of the catheter. During manufacturing, a cover 1488 is employed to seal the wall after the opening is cut into the wall. The cover 1488, for example, may be a thin elastomer cover or a radiopaque band that is placed over the opening.

Additionally, rather than being substantially rectangular in profile, the cut in the wall 1411 may have a tapered shape along the peripheral direction, i.e., perpendicular to the dividing wall 1425. This tapered shape is illustrated by FIGS. 14B-C. For example, the catheter 1400 may be configured so that the fluid flows in the interior chamber 1421 from the proximal end 1412 toward the distal end 1414, and the fluid flows back to the proximal end 1412 in the interior chamber 1423. In this case, the fluid flows from the interior chamber 1421 to the other interior chamber 1423 via the connecting chamber 1480. The connecting channel 1480 may be tapered so that it becomes wider as it extends from the interior chamber 1421 to the other interior chamber 1423. In other words, the connecting chamber 1480 is narrower at the interior chamber 1421 and wider at the interior chamber 1423. This tapered shape help to keep the connecting channel free from clot formation that may cause a mechanical lock. Thus, employing a connecting channel 1480 with a narrower end at the higher-pressure chamber and a wider end at the lower-pressure chamber facilitates removal of any clot that may form in the connecting channel 1480.

Although catheters, as described previously, may employ a valve to control flow through a connecting channel between interior chambers, another valve is not required with the connecting channel 1480 in the catheter 1400. The connecting channel 1480 is sized appropriately and the flow rate through the interior chambers 1421 and 1423 is sufficiently high to substantially prevent flow through the connecting channel 1480 when the valve mechanism 1430 is in the open valve position. In general, flow through the connecting channel 1480 when the valve mechanism 1430 is in the open valve position is less likely when it has smaller dimensions.

Figure 15A:
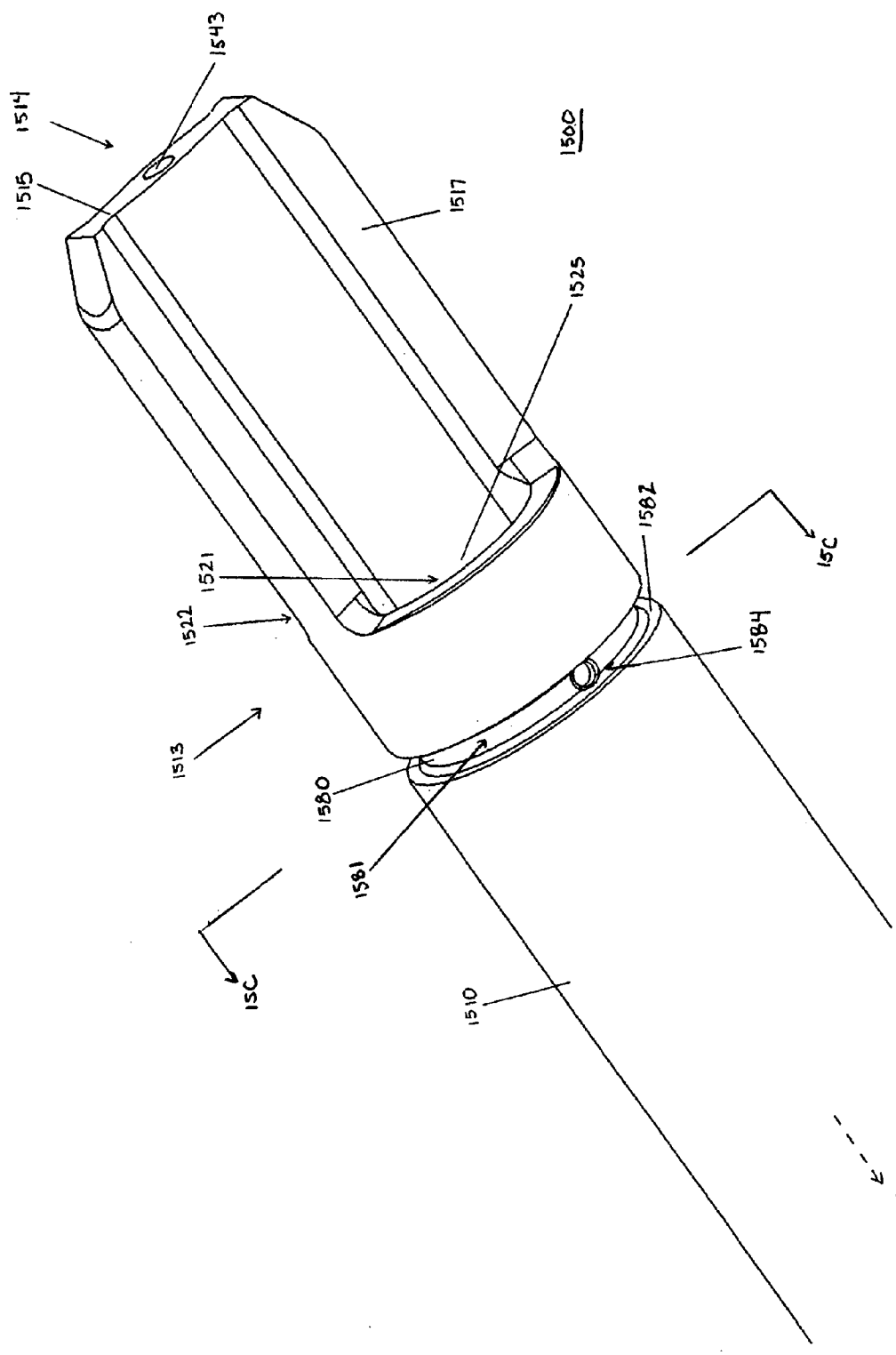
FIG. 15A illustrates an exemplary embodiment having a connecting channel connecting two interior chambers.
Figure 15B:
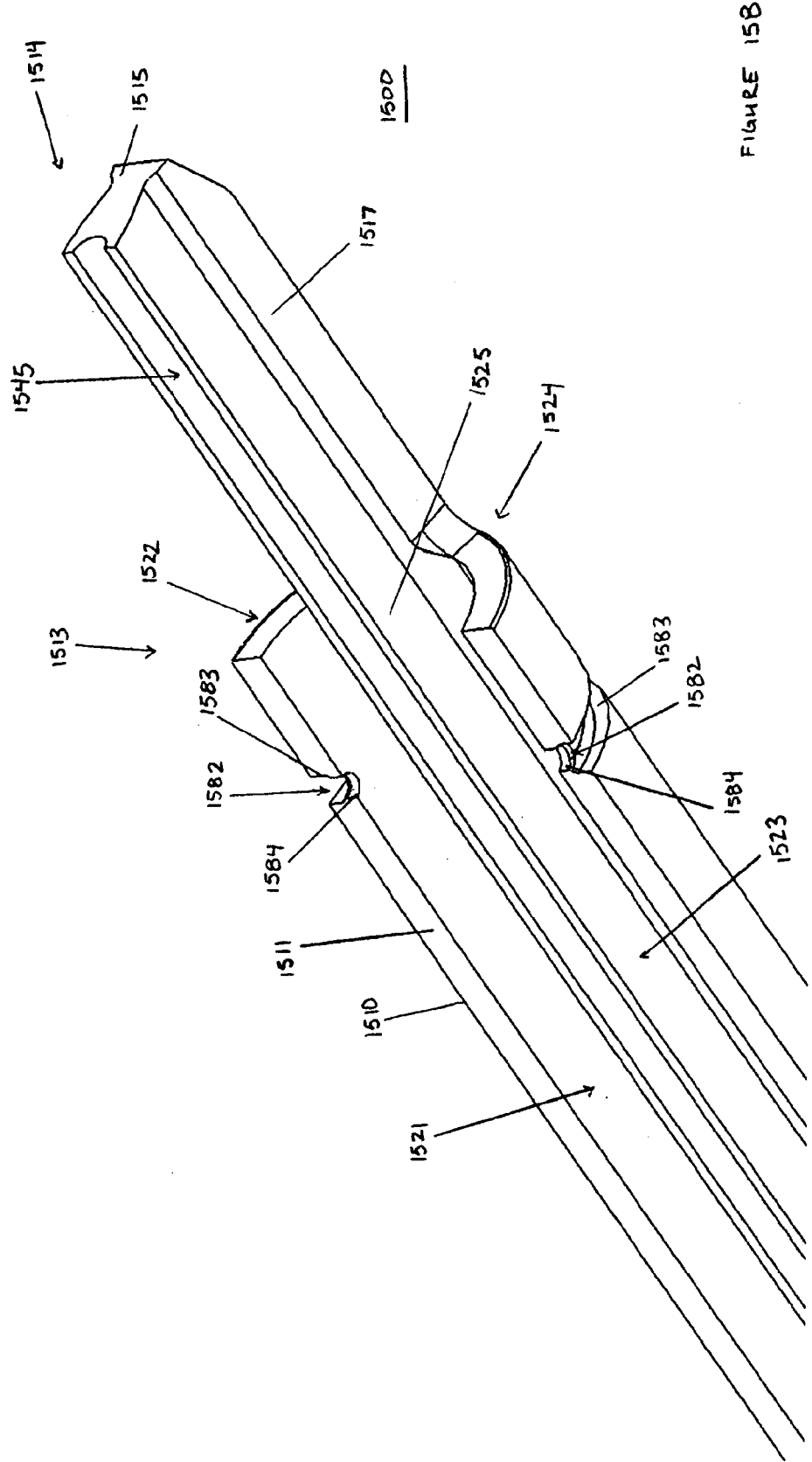
FIG. 15B illustrates a cut-out view of the embodiment of FIG. 15A.

Referring to FIGS. 15A-B, an alternative embodiment of a connecting channel is illustrated as a part of a catheter 1500, which is otherwise similar to the catheter 1400 described previously. As shown in FIG. 15A, the catheter 1500 extends longitudinally from a proximal end 1512 to a distal end 1514. In particular, the catheter 1500 includes a catheter body 1510 that extends from the proximal end 1512 to an intermediate section 1513. As shown in the cut-out view of FIG. 15B, a dividing wall 1525 defines two interior chambers 1521 and 1523 within the catheter body 1510. The interior chambers 1521 and 1523 have corresponding chamber openings 1522 and 1524 at the intermediate section 1513. In addition, the dividing wall 1517 extends from the chamber openings 1522 and 1524 toward the distal end 1514 to define a guide structure 1517. The guide structure 1517 provides similar advantages as the guide structure 1417 described previously and may accommodate a valve mechanism (not shown), such as the valve mechanism 1430, to control the flow of fluid through the chamber openings 1522 and 1524. FIG. 15B also shows a control wire channel 1545 passing through the dividing wall 1525 and the guide structure 1517. The control wire channel 1545 may accommodate a control wire, such as the control wire 1440, which may be coupled to the valve mechanism and operated from the proximal end 1512 to move the valve mechanism between a closed valve position to an open valve position.

Figure 15C:
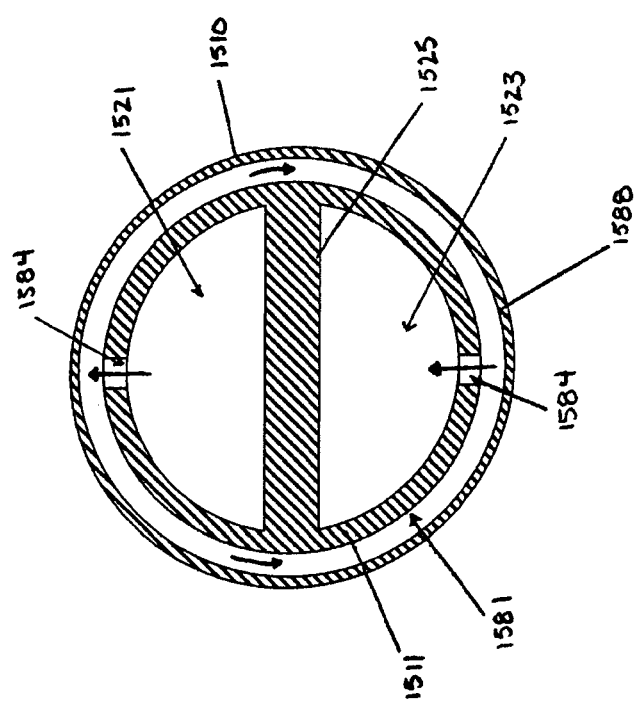
FIG. 15C illustrates a cross-sectional view of the connecting channel extending between the interior chambers of the exemplary embodiment of FIG. 15A.

Catheter 1500 includes a connecting channel 1580 that provides the advantages of the connecting channel 1480 described previously. However, the connecting channel 1580 differs from the connecting channel 1480. In particular, the connecting channel 1580 is defined in part by a groove 1581 that is cut into the catheter wall 1510 and extends along the entire periphery of the catheter body 1510, e.g., substantially 360°. As shown in FIGS. 15A-C, the groove 1581 may lie along an imaginary plane that cuts transversely through the catheter body 1510. As shown in the cross-sectional view of FIG. 15C, the groove 1581 extends inwardly from the outer surface of the catheter body 1510, but does not extend completely through the catheter wall 1511. In other words, the groove walls 1582 defining the groove 1581 have a thickness that is less than the thickness of the catheter wall 1511. For example, the groove 1581 has a thickness that is approximately 50% of the catheter wall 1511. In one embodiment, the groove 1581 may approximately 10 to 15 mils in thickness where the catheter wall is approximately 20 to 30 mils.

Apertures, or weep holes, 1584 extend between the groove 1581 and the interior chambers 1521 and 1523 and provide fluid communication therebetween. A cover 1588 is applied over the groove 1581 along the outer surface of the catheter body 1510 to seal the catheter wall 1511 after the groove 1581 is cut into the catheter wall 1511. The cover 1588, for example, may be a thin elastomer cover or a radiopaque band that is placed over the opening. As shown by the example flow arrows in FIG. 15C, fluid may flow from one of the interior chambers 1521 and 1523, through the corresponding aperture 1584, and into the other interior chamber without escaping out of the catheter 1500. Accordingly, the connecting channel 1580 permits the interior chambers 1521 and 1523 to be filled and/or flushed when the chamber openings 1522 and 1523 are closed by a valve mechanism.

In one embodiment, the apertures may be approximately 20 mils where the groove 1581 may approximately 10 to 15 mils in thickness. The flow between the interior chambers 1521 and 1523 is determined by the size and shape of the apertures 1584 as well as the size of the groove 1581. Thus, although FIGS. 15A-C illustrate two opposing apertures 1584 that extend into the interior chambers 1521 and 1523, respectively, additional apertures may be employed to improve flow rate between the connecting channel 1580 and the interior chambers 1521 and 1523. In general, the connecting channel 1580 is dimensioned appropriately and the flow rate through the interior chambers 1521 and 1523 is sufficiently high to substantially prevent flow through the connecting channel 1580 when the valve mechanism is in the open valve position. However, the connecting channel 1580 is also dimensioned to achieve sufficient flow through between the interior chambers 1521 and 1523 when the valve mechanism is closed.

The connecting channel 1580, which may be employed in any catheter, provides manufacturing advantages, because it is formed by efficiently cutting a groove 1581 into the wall 1511 of the catheter and drilling apertures 1584 from the groove 1581 into the interior chambers 1521 and 1523. A cover 1588 is then applied over the groove 1581 to seal the wall after the opening is cut into the wall.

Figure 12A:
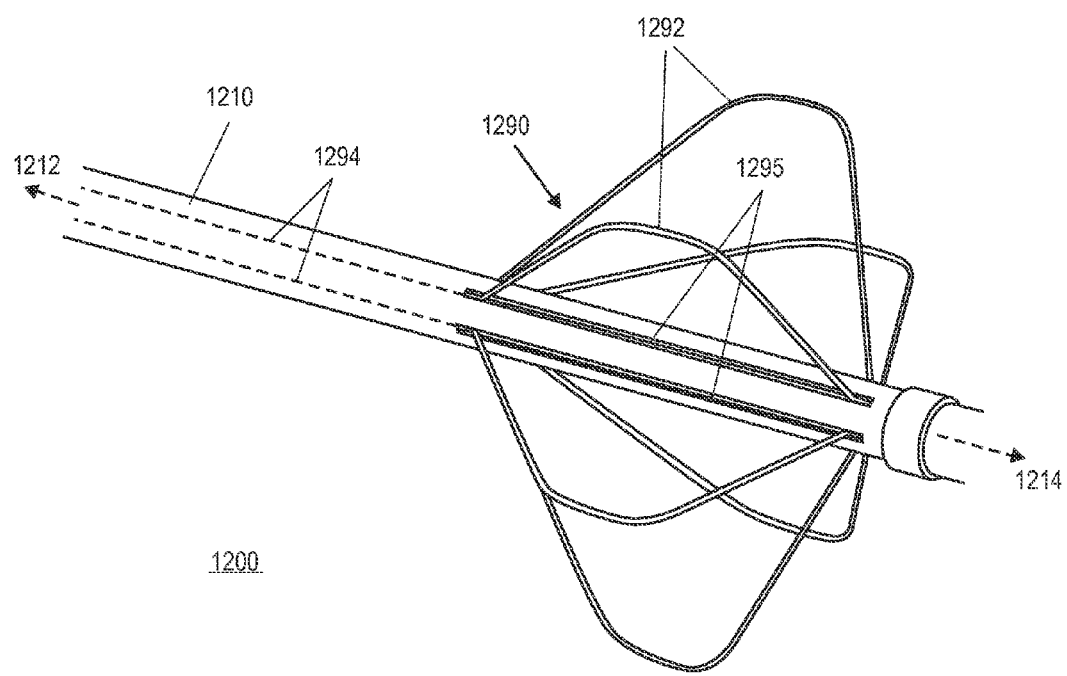
FIG. 12A illustrates a distal end of an exemplary embodiment employing elongate wires for a manually operated centering mechanism.
Figure 12B:
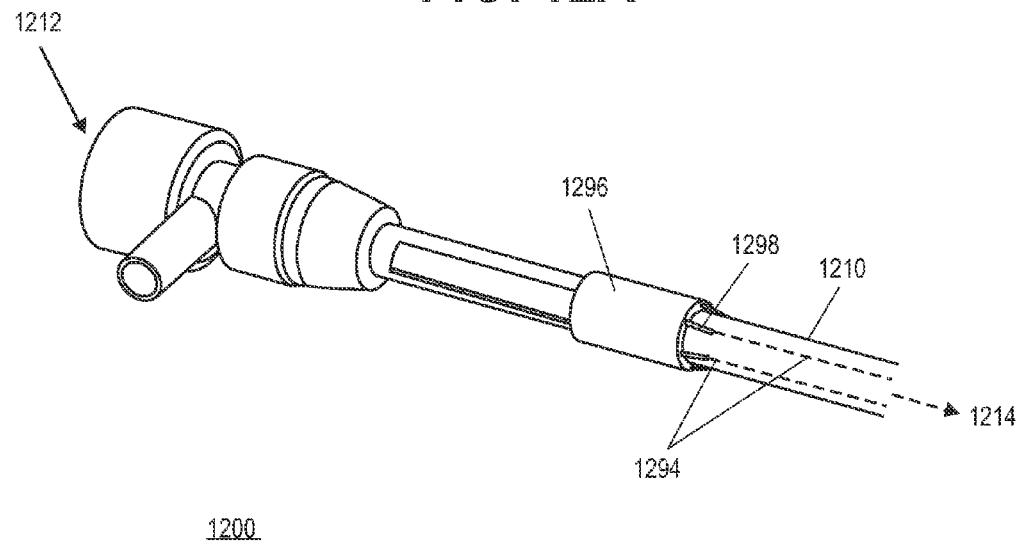
FIG. 12B illustrates a proximal end of the exemplary embodiment of FIG. 12A.

As also discussed previously, it is believed that poor catheter position or catheter kinking may also be partially responsible for the low patency rates. As such, exemplary embodiments of the present invention may employ a centering mechanism to position the catheter away from the wall of the vessel. The centering mechanism spaces the catheter from the vessel wall and substantially prevents the chamber opening of an intake chamber from being auctioned to the wall. In the embodiment of FIGS. 12A-B, the catheter 1200 employs a manually operated centering mechanism 1290 that may be expanded or contracted. Expansion of the centering mechanism 1290 occurs radially outwardly from the longitudinal line of the catheter. As shown in FIG. 12A, the centering mechanism 1290 has a plurality of elongate wires 1292, each of which has a first end secured to the catheter body 1210 adjacent to the distal end 1214. Each wire passes through an enclosed channel 1294 formed in the wall of the catheter body 1210 and extends toward the proximal end 1212 of the catheter 1200. The centering mechanism 1290 may be formed from a biocompatible material, such as NiTI, polymers, elastomers, super-alloys, and stainless steel.

As shown in FIG. 12B, near the proximal end 1212, each wire 1292 exits the respective enclosed channel 1294 and extends further to a control slide 1296 mounted for movement along the catheter body 1210. The end of each wire 1292 is secured at 1298 to the control slide 1296. When the control slide 1296 is drawn back to a position closest to the proximal end 1212, the wires 1292 at the distal end 1214 of the catheter body are drawn flat into slots 1295 in the catheter body 1210 at the distal end of each enclosed channels 1294. With the control slide 1296 at its most proximal position, each wire 1292 neatly fits into an underlying slot 1295 to maintain a smooth external catheter surface. On the other hand, movement of the control slide 1296 toward the distal end 1214 of the catheter body 1210 pushes the wires 1292 out of the slots 1295 to form the centering basket shown in FIG. 12B. The size of this centering basket is dependant upon how far the control slide 1296 is moved in the distal direction. After a dialysis session is completed, the centering basket is easily collapsed by moving the control slide back 1296 to its most proximal position. The collapsed centering basket also facilitates positioning and removal of the catheter 1200.

Figure 12C:
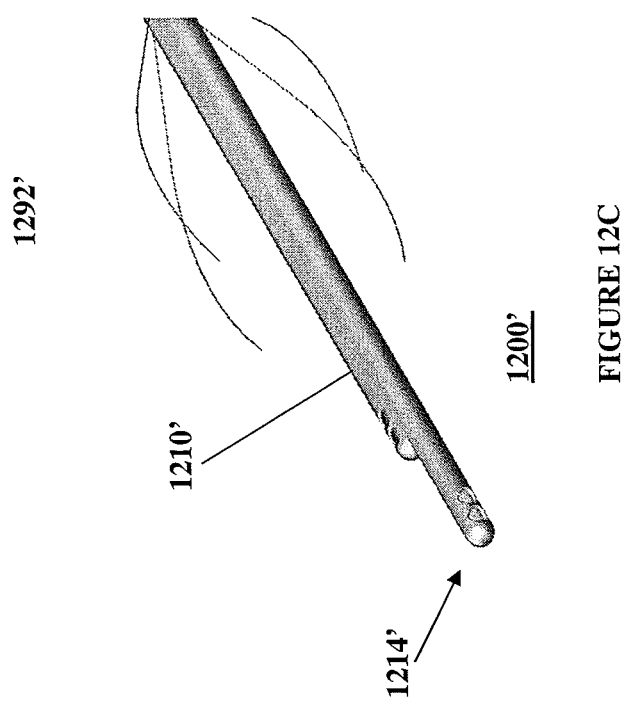
FIG. 12C illustrates the distal end of another exemplary embodiment employing elongate wires for a manually operated centering mechanism.

Although each of the plurality of elongate wires 1292 shown in FIG. 12A has a first end secured to the catheter body 1210 adjacent to the distal end 1214, the centering basket may be formed without connecting the first end to the catheter body. For instance, as shown in FIG. 12C, the wires 1292' for catheter 1200' may be formed from a flexibly resilient material that is biased to form a self-expanding centering basket when they are not drawn into, and collapsed within, the slots.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

What is claimed is:

1. A method for flushing a catheter, the method comprising: providing a catheter, the catheter comprising: an elongate body having a proximal end and a distal end; a first chamber extending within the elongate body from the proximal end to a first chamber opening at the distal end; a second chamber extending within the elongate body from the proximal end to a second chamber opening at the distal end; a valve structure at the distal end of the elongate body that is configured to move relative to the elongate body between a closed position in which the first and second chamber openings are covered by the valve structure and an open position in which the first and second chamber openings are uncovered by the valve structure; and a channel located between the proximal and the distal ends of the elongate body that extends between the first chamber and the second chamber and provides fluid communication between the first chamber and the second chamber when the valve structure is in the closed position; positioning the valve structure to close off the distal end of the first chamber lumen and the e distal end of the e second chamber lumen of the catheter; while the distal ends are closed off by the valve structure, introducing a flushing fluid into the proximal end of the first chamber lumen; passing the flushing fluid through the channel that extends between connecting the first chamber and lumen to the second chamber lumen; and withdrawing the flushing fluid from the proximal end of the second chamber lumen, wherein the catheter further comprises a dividing wall within the elongate body separating the first and second chambers, the dividing wall extending from the proximal end of the elongate body to the first and second chamber openings, wherein the channel extends through the dividing wall.

2. The method according to claim 1 wherein the valve structure further comprises a gate extending along the dividing wall, the gate configured to cover the channel when the valve structure is in the open position.

3. The method according to claim 1 wherein the channel comprises a micro-hole that extends through the dividing wall.

4. The method according to claim 3 further comprising at least one additional micro-hole extending through the dividing wall.

5. The method according to claim 1, wherein the channel between the first chamber and the second chamber comprises an opening cut through the outer wall of the elongate body.

6. The method according to claim 1 wherein the channel extends substantially perpendicular to the dividing wall.

7. A method according to claim 1 wherein the channel extends from an outer surface of the wall of the elongate body into part of the dividing wall.

8. The method according to claim 1 wherein the channel has a tapered shape that is wider in the first chamber than in the second chamber.

9. The method according to claim 1 wherein the catheter further comprises a cover along a portion of the elongate body positioned over the channel so as to at least partially seal the channel.

10. The method according to claim 1 wherein the valve structure at the distal end of the elongate body is configured to move relative to the elongate body along a guide structure that extends from the distal openings of the first and second chambers to the distal end of the elongate body.

11. The method according to claim 10 wherein the valve structure moves along the guide structure to an open position wherein the valve structure remains proximal to the distal most end of the guide structure.

12. The method according to claim 10 wherein the valve structure moves along the guide structure to an open position wherein the valve structure extends beyond the distal most end of the guide structure.

* * * * *